United States Patent [19]

Bare et al.

[11] Patent Number: 5,739,133
[45] Date of Patent: *Apr. 14, 1998

[54] PYRIDAZINEDIONE COMPOUNDS USEFUL IN TREATING NEUROLOGICAL DISORDERS

[75] Inventors: Thomas Michael Bare, West Chester; Richard Bruce Sparks, Linwood, both of Pa.

[73] Assignee: Zeneca Limited, London, England

[*] Notice: The term of this patent shall not extend beyond the expiration date of Pat. Nos. 5,604,227 and 5,599,814.

[21] Appl. No.: 700,654

[22] Filed: Aug. 15, 1996

Related U.S. Application Data

[63] Continuation of Ser. No. 421,133, Apr. 13, 1995, Pat. No. 5,604,227, which is a continuation of Ser. No. 156,659, Nov. 22, 1993, abandoned, which is a continuation of Ser. No. 880,965, May 8, 1992, abandoned.

[30] Foreign Application Priority Data

| May 9, 1991 | [GB] | United Kingdom | 9109973 |
| Feb. 13, 1992 | [GB] | United Kingdom | 9202991 |

[51] Int. Cl.$^6$ .................... A61K 31/50; C07D 471/14
[52] U.S. Cl. .................................. 514/248; 544/234
[58] Field of Search .......................... 544/234; 514/248

[56] References Cited

U.S. PATENT DOCUMENTS

| 5,599,814 | 2/1997 | Bare et al. | 544/234 |
| 5,604,227 | 2/1997 | Bare et al. | 544/234 |

OTHER PUBLICATIONS

Luo et al., J. Heterocyclic Chem. 28, 205–208 (1991).
Kurasawa et al., Chem. Pharm.Bull. 28(12) 3457–3465 (1980).
Godard et al., Bull. Soc. Chim. Fr. 1588–1592 (1972).
Ried et al., Chem. Ber. 85, 204–216 (1952).
Choi, Neuron, 1, p. 623–634 (1988).
Koh et al, Brain Research, 533, p. 315–320 (1990).
Perry et al, Neurology, 40, p. 20–24 (1990).
Albin et al, New England Journal of Medicine, 322 p. 1293–1298 (1990).
Cotton, Journal of American Medical Association, 264, p. 305–306 (1990).
Trujillo et al, Science 251, p. 85–87 (1991).
Turski et al., Nature 349, p. 414–420 (1991).
Sinkula in Annual Reports in Medicinal Chemistry, vol. 10, p. 306–315 (1975).

Primary Examiner—Emily Bernhardt
Attorney, Agent, or Firm—Michael D. Alexander; Richard A. Elder

[57] ABSTRACT

The present invention relates to pyridazino[4,5-b] quinolines, and pharmaceutically useful salts thereof, which are excitatory amino acid antagonists and which are useful when such antagonism is desired such as in the treatment of neurological disorders. The invention further provides pharmaceutical compositions containing pyridazino[4,5-b] quinolines as active ingredient, and methods for the treatment of neurological disorders.

6 Claims, No Drawings

PYRIDAZINEDIONE COMPOUNDS USEFUL IN TREATING NEUROLOGICAL DISORDERS

This application is a continuation of prior application Ser. No. 08/421,133, filed Apr. 13, 1995, U.S. Pat. No. 5,604,227, which in turn is a continuation of our prior application Ser. No. 08/156,659, filed Nov. 22, 1993, now abandoned, which in turn is a continuation of our prior application Ser. No. 07/880,965, filed May 8, 1992, now abandoned.

This invention relates to pyridazinedione compounds useful in the treatment of neurological disorders generally in mammals such as man. More specifically, the compounds are useful in the treatment of strokes and/or other neurodegenerative disorders such as hypoglycemia, cerebral palsy, transient cerebral ischemic attack, perinatal asphyxia, epilepsy, psychosis, Huntington's chorea, amyotrophic lateral sclerosis, Alzheimer's disease, Parkinson's disease, Olivo-pontocerebellar atrophy, vital-induced neurodegeneration such as in acquired immunodeficiency syndrome and its associated dementia, anoxia such as from drowning, spinal cord and brain trauma, and chronic pain, for the prevention of drug and alcohol withdrawal symptoms, and for the inhibition of tolerance and dependence to opiate analgesics. The invention particularly relates to novel pyridazinedione compounds useful in reducing neurological degeneration such as can be induced by a stroke and the associated functional impairment which can result. Treatment using a compound of the invention can be remedial or therapeutic as by administering a compound following an ischemic event to mitigate the effects of that event. Treatment can also be prophylactic or prospective by administering a compound in anticipation that an ischemic event may occur, for example in a patient who is prone to stroke.

It is known that ischemic events can trigger a dramatic increase in extracellular concentrations of the excitatory amino acids glutamate and aspartate which can, in turn, cause prolonged neuronal excitation leading to a massive influx of calcium from extracellular to intracellular sites in brain neural cells. A calcium overload can thereby be created which leads to a cascade of events leading to cell catabolism and eventually resulting in cell death. The N-methyl-D-aspartate (NMDA) receptor complex is believed to play a significant role in the cascade of events leading to cell necrosis following an ischemic event.

The compounds provided by this invention may be useful in a variety of neurodegenerative disorders because they function as excitatory amino acid antagonists. They may do so indirectly, via allosteric modulation of the glutamate binding site, specifically by acting as antagonists of the strychnine-insensitive glycine receptor on the NMDA receptor complex. They may also do so directly, by binding to the glutamate site itself on the NMDA receptor complex.

According to the invention there is provided a pharmaceutical composition suitable for the treatment of neurological disorders, comprising a compound of formula I (formula set out, together with other formulae referred to by Roman Numerals, on pages following the Examples), wherein $R^3$ is selected from hydrogen, amino, hydrazino, hydroxy and thiohydroxy;

Ring A is selected from the members shown as formulae Ia–Ih, wherein $R^4$, $R^5$, $R^6$, and $R^7$ are independently selected from the group consisting of hydrogen, halo, (1–4C)alkyl which may contain a double or triple bond, (1–3C)perfluoroalkyl, (1–3C)alkyl substituted with trifluoromethyl, nitro, $OR^d$, $CO_2R^d$, $CONR^d_2$, CN, $NR^d_2$, and cyclopropyl, wherein each $R^d$ is independently selected from hydrogen and (1–4C)alkyl;

or a compound obtained by mono-, di-, or tri-acylating a compound of formula I with an acylating agent having the formula $R^8COX'$, wherein X' is a conventional leaving group, and wherein $R^8$ is selected from (1) hydrogen,
(2) (1–12C)alkyl which may contain a double or triple bond, and which may bear a group selected from
   (a) CN, $OR^e$, and $CO_2R^e$, wherein $R^e$ is selected from hydrogen, (1–4C)alkyl, and phenyl and phenyl(1–4C)alkyl the phenyl rings of which can be substituted with from 0–3 substituents selected from halo, amino, hydroxy, cyano, nitro, (1–4C)alkyl, and (1–4C)alkoxy;
   (b) $NR^f_2$ and $CONR^f_2$ wherein each $R^f$ is independently selected (1) from $R^h$, $COR^h$, and $COOR^h$ when the said group is $NR^f_2$ and (2) from the values of $R^h$ when the said group is $CONR^f_2$, wherein $R^h$ can have any of the values stated above for $R^e$, or wherein, for either of the said groups, the two $R^f$ values, together with the nitrogen to which they are attached, form a saturated 4- to 7-membered ring,
(3) $NR^g_2$ wherein each $R^g$ can independently have any of the values stated above for $R^e$, or wherein the two $R^g$ groups together with the nitrogen to which they are attached form a saturated 4- to 7-membered ring,
(4) pyridyl, pyridyl(1–12C)alkyl,
(5) phenyl, and phenyl(1–4C)alkyl wherein the phenyl rings can be substituted with from 0–3 substituents selected from halo, amino, hydroxy, cyano, nitro, (1–4C)alkyl, and (1–4C)alkoxy;

or a product obtained by mono-, di-, or tri-alkylating a compound of formula I with an alkylating agent having the formula $R^{12}X$, wherein X is a conventional leaving group, and wherein $R^{12}$ is selected from (1–4C)alkyl which may contain a double or triple bond provided that, if a double or triple bond is present, a methylene group intervenes between said double or triple bond and the group to which said alkyl is attached, phenyl(1–4C)alkyl wherein the phenyl ring can be substituted with from 0–3 substituents selected from halo, amino, hydroxy, cyano, nitro, (1–4C)alkyl, and (1–4C)alkoxy, and $(CH_2)_m COOR^a$ wherein $R^a$ is hydrogen or (1–4C)alkyl and m is 1–6;

or a pharmaceutically acceptable salt thereof, and a pharmaceutically acceptable diluent or carrier.

The compounds (1) thieno[2',3':5,6]pyrido[2,3-d]pyridazine-5,8,9(4H,6H,7H)-trione and (2) thieno[3',2':5,6]pyrido[2,3-d]pyridazine-4,5,8(6H,7H,9H)-trione are known, for example from J. Heterocyclic Chem., 28, 205, (1991). These compounds, as named, are tautomeric forms of compounds within the scope of formula I as defined above, i.e. see, respectively, (1) formula IIh with $R^3$=hydroxy, and $R^1$, $R^2$, $R^4$ and $R^5$=H and (2) formula IIf with $R^3$=hydroxy, and $R^1$, $R^2$, $R^5$ and $R^6$=H.

Other compounds within the scope of formula I are also known from, for example, Beilstein's Handbuch der Organischen Chemie; Godard et. al., Bull. Soc. Chim. Fr., 1588, (1972); and Reid et. al., Chem. Ber., 85, 204, (1952), including the following compounds having the formulae:

(a) formula I, with ring A having formula Ia, $R^3$–$R^7$=H;
(b) formula I, with ring A having formula IA, $R^3$=H, $R^4$–$R^5$=OCH$_3$, and $R^6$–$R^7$=H; and (c) certain mono- and diacetylated and diethylated derivatives of formula I, with ring A having formula Ia.

The remaining compounds within the scope of formula I, alkylated derivatives thereof, and acylated derivatives thereof, are believed to be novel (regardless of any particular tautomeric or positional isomeric form in which they can be drawn), and are provided as an additional feature of the invention. The novel compounds thus include those of formula I as defined above, including alkylated and acylated derivatives thereof, but excluding compounds wherein:

(a) said compound is of formula I, ring A has formula If or Ih, $R^4$, $R^5$, and $R^6$ are hydrogen and $R^3$ is hydroxy (or the tautomerically equivalent oxo);

(b) said compound is of formula I, ring A has formula Ia, and $R^3$–$R^7$ are each hydrogen;

(c) said compound is a product made by monoacetylating, diacetylating, or diethylating a compound of formula I wherein ring A has formula Ia and $R^3$–$R^7$ are each hydrogen; and (d) said compound is of formula I, Ring A has formula Ia, $R^4$ and $R^5$ are each OCH3, $R^3$ is hydrogen and $R^6$–$R^7$ are hydrogen.

Particular subgroups within the above broadly defined group of compounds include those compounds having the specific positional isomeric formulae I' or I", wherein:

$R^1$ and $R^2$ are independently selected from:
hydrogen,
(1–4C)alkyl which may contain a double or triple bond provided that, if a double or triple bond is present, a methylene group intervenes between said double or triple bond and the atom to which said alkyl is attached, and
$COR^8$ wherein $R^8$ is selected from
(1) (1–12C)alkyl which may contain a double or triple bond, or which may bear a group selected from
(a) CN, $OR^e$, and $CO_2R^e$, wherein $R^e$ is selected from hydrogen, (1–4C)alkyl, and phenyl and phenyl(1–4C)alkyl the phenyl rings of which can be substituted with from 0–3 substituents selected from halo, amino, hydroxy, cyano, nitro, (1–4C)alkyl, and (1–4C)alkoxy;
(b) $NR^f_2$ and $CONR^f_2$ wherein each $R^f$ is independently selected (1) from $R^h$, $COR^h$, and $COOR^h$ when the said group is $NR^f_2$ and (2) from the values of $R^h$ when the said group is $CONR^f_2$, wherein $R^h$ can have any of the values stated above for $R^e$, or wherein, for either of the said groups, the two $R^f$ values, together with the nitrogen to which they are attached, form a saturated 4- to 7-membered ring,
(2) $NR^g$ wherein each $R^g$ can independently have any of the values stated above for $R^e$, or wherein the two $R^g$ groups together with the nitrogen to which they are attached form a 4- to 7-membered ring,
(3) pyridyl, pyridyl(1–12C)alkyl,
(4) phenyl, and phenyl(1–4C)alkyl wherein the phenyl rings can be substituted with from 0–3 substituents selected from halo, amino, hydroxy, cyano, nitro, (1–4C)alkyl, and (1–4C)alkoxy;

$R^3$ is selected from hydrogen, hydrazino, $OR^9$, $NHR^{10}$, and $SR^9$, wherein
$R^9$ is selected from
(i) hydrogen, (ii) (1–4C)alkyl which may contain a double or triple bond, provided that, if a double or triple bond is present, a methylene group intervenes between said double or triple bond and the oxygen, nitrogen, or sulfur to which said alkyl is attached and (iii) $(CH_2)_pCOOR^c$ wherein $R^c$ is hydrogen or (1–4C)alkyl and p is 1–6;

$R^{10}$ is selected from hydrogen and $(CH_2)_nCOOR^b$ wherein $R^b$ is hydrogen or (1–4C)alkyl and n is 1–6;

Ring A is selected from the members shown as formulae Ia–Ih, wherein $R^4$, $R^5$, $R^6$, and $R^7$ are independently selected from the group consisting of hydrogen, halo, (1–4C)alkyl which may contain a double or triple bond, (1–3C)perfluoroalkyl, (1–3C)alkyl substituted with trifluoromethyl, nitro, $OR^d$, $CO_2R^d$, $CONR^d_2$, CN, $NR^d_2$, and cyclopropyl, wherein $R^d$ is selected from hydrogen and (1–4C)alkyl; and pharmaceutically acceptable salts thereof.

More particular subgroups include those compounds having the specific positional isomeric formulae I' and I", wherein $R^1$ and $R^2$ are independently selected from the values of $COR^8$ given immediately above, and pharmaceutically acceptable salts thereof.

An additional subgroup includes compounds of formula I wherein $R^3$ is selected from hydrogen, hydrazino, amino, hydroxy, and thiohydroxy, and ring A is as previously defined, and pharmaceutically acceptable salts thereof.

An additional subgroup includes the compounds obtained by mono- and di-acylating any of the compounds in the additional subgroup immediately above.

It will be appreciated that within the above definitions there are included a number of additional subgroups of compounds of formula I, alkylated derivatives thereof, and acylated derivatives thereof, for example:

(a) compounds of formula IIa;
(b) compounds of formula IIb;
(c) compounds of formula IIc;
(d) compounds of formula IId;
(e) compounds of formula IIe;
(f) compounds of formula IIf;
(g) compounds of formula IIg; and
(h) compounds of formula IIh.

In the formulae IIa–IIh, $R^1$–$R^7$ are as previously defined, except, for the sake of convenience in discussing these particular formulae, the values corrresponding to $R^1$ and $R^2$ additionally include hydrogen. It will be appreciated that formulae IIa–IIh can be drawn in various tautomeric and positional isomeric forms, as discussed below. These particular are intended to include such alternate forms unless otherwise indicated, and also to include salts thereof, especially the pharmaceutically acceptable addition salts.

It will be appreciated by those skilled in the art that many of the compounds disclosed herein can exist and be drawn in various true tautomeric forms (i.e., for compounds corresponding to a compound of formula I) and positional isomeric forms (i.e., for compounds corresponding to an acylated or alkylated derivative of a compound of formula I), such as the generic formulae shown as formula III and formulae IIIa–IIIc which are tautomeric/positional isomeric forms of formulae I, I', and I" involving the pyridazino ring. For the sake of convenience, the term "tautomer", "tautomeric form", etc. is used hereinafter to refer to positional isomers as well as true tautomers. It is noted that tautomeric forms of these compounds can also exist when $R^3$ is hydroxy, thiohydroxy, amino, or alkylamino, and examples are shown as formulae IIId and IIIe. It will be appreciated that any positional isomer corresponding to a compound of formulae IIIa–IIIe can exist depending on which true tautomeric form is alkylated or acylated. It is to be understood that all references to any particular structure are understood to include the various tautomeric and positional isomeric forms thereof unless otherwise stated.

It will further be appreciated by those skilled in the art that certain compounds of formula I contain an asymmetrically substituted carbon atom, and accordingly may exist in, and be isolated in, optically-active and racemic forms. In addition, it will be appreciated that certain compounds of formula I, for example, those containing a double bond, may exist in, and be isolated in, separate stereoisomeric forms ('E' and 'Z') about that group. Some compounds may exhibit polymorphism. It is to be understood that the present invention encompasses any racemic, optically-active, polymorphic or stereoisomeric form, or mixtures thereof, which form possesses properties useful in the treatment of neurodegenerative disorders, it being well known in the art how to prepare optically-active forms (for example, by resolution of the racemic form or by synthesis from optically-active starting materials) and individual 'E' and 'Z' stereoisomers (for example, by chromatographic separation of a mixture thereof) and how to determine neuroprotective properties by the standard tests described hereinafter.

The invention further provides a method for the treatment of neurological disorders, comprising administering to a mammal in need of such treatment an effective amount of a compound according to the invention as defined below, or a pharmaceutically acceptable salt thereof, or a composition as defined above.

While not wishing to be bound by theory, it is believed that for compounds according to the invention where $R^1$ and/or $R^2$ are acyl moieties, or for a compound which is otherwise an acylated derivative of a compound of formula I (including any of the various positional isomeric forms, as discussed further below), such compounds may not only be active on their own, but may also be active even though an acyl moiety (or two acyl moieties in the case of diacyl compounds) are cleaved in vivo. Alternatively, it may be possible that some acylated species are inactive per se, but that they become active after one or two acyl moieties are cleaved in vivo, and are thus acting as prodrugs.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

Particular values of (1–4C)alkyl include methyl, ethyl, propyl, isopropyl, butyl, isobutyl, sec-butyl, and tert-butyl.

Particular values of (1–4C)alkyl containing a double or triple bond include vinyl, 2-propenyl (i.e. allyl), 2-propynyl, (i.e. propargyl), 2-butenyl, and 3-butenyl.

Particular values of (1–4C)alkoxy include methoxy, ethoxy, propoxy, isopropoxy, butoxy, isobutoxy, and t-butocy.

Particular values of (1–12C)alkyl include methyl, ethyl, propyl, isopropyl, butyl, isobutyl, sec-butyl, tert-butyl, pentyl, isopentyl, neopentyl, hexyl, isohexyl, heptyl, isoheptyl, octyl, 2,2,4-trimethylpentyl, nonyl, isononyl, decyl, isodecyl, undecyl, isoundecyl, dodecyl, and isododecyl.

Particular values of (1–12C)alkyl containing a double or triple bond include vinyl, 2-propenyl (i.e. allyl), 2-propynyl, (i.e. propargyl), but-2-enyl, 2-pentenyl, 3-pentenyl, 4-pentenyl, 4-pentynyl, 5-hexenyl, 5-hexynyl, 6-heptenyl, 6-heptynyl, 7-octenyl, 7-octynyl, 11-dodecenyl, and 11-dodecynyl.

Particular values of phenyl substituted with from 0–3 substituents include phenyl; 2-, 3-, and 4-halophenyl; 2-, 3-, and 4-aminophenyl; 2-, 3-, and 4-hydroxyphenyl; 2-, 3-, and 4-cyanophenyl; 2-, 3-, and 4-nitrophenyl; 2-, 3-, and 4-methylphenyl; 2-, 3-, and 4-ethylphenyl; 2-, 3-, and 4-propylphenyl; 2-, 3-, and 4-methoxyphenyl; 2-, 3-, and 4-ethoxyphenyl; 2-, 3-, and 4-propoxyphenyl; and 3,5-dihalophenyl, 3-halo-4-hydroxyphenyl, and 3,5-dihalo-4-hydroxyphenyl.

Particular values of phenyl(1–4C)alkyl substituted with from 0–3 substituents include benzyl, phenylethyl, phenylpropyl, phenylbutyl; 2-, 3-, and 4-halobenzyl; 2-, 3-, and 4-aminobenzyl; 2-, 3-, and 4-cyanobenzyl, 2-, 3-, and 4-nitrobenzyl, 2-, 3-, and 4-methylbenzyl; 2-, 3-, and 4-ethylbenzyl; 2-, 3-, and 4-propylbenzyl; 2-, 3-, and 4-hydroxybenzyl; 2-, 3-, and 4-methoxybenzyl; 2-, 3-, and 4-ethoxybenzyl; 2-, 3-, and 4-propoxybenzyl; and 3,5-dihalobenzyl, 3-halo-4-hydroxybenzyl, and 3,5-dihalo-4-hydroxybenzyl.

Particular values of pyridyl include 2-, 3-, and 4-pyridyl.

Particular values of pyridyl(1–12C)alkyl include 2-, 3-, and 4-pyridylmethyl, 2-, 3-, and 4-pyridylethyl, 2-, 3-, and 4-pyridylpropyl, 2-, 3-, and 4-pyridylbutyl, 2-, 3-, and 4-pyridyloctyl, and 2-, 3-, and 4-pyridylnonyl.

Particular values of (1–3C)perfluoroalkyl include trifluoromethyl, pentafluoroethyl, and heptafluoropropyl.

Particular values of (1–3C)alkyl substituted with a trifluoromethyl group include trifluoromethylmethyl, 2-trifluoromethylethyl, 1-trifluoromethylethyl, and 3-trifluoromethylpropyl.

Particular values of 4- to 7-membered rings containing nitrogen include piperidino, pyrrolidinyl, and azetidinyl.

More particular values of (1–4C)alkyl include methyl, ethyl, propyl, isopropyl, butyl, isobutyl, sec-butyl, and tert-butyl.

More particular values of (1–4C)alkyl which can contain a double or triple bond include methyl, ethyl, allyl, ethynyl, and propargyl.

More particular values of (1–12C)alkyl include methyl, ethyl, propyl, isopropyl, butyl, isobutyl, sec-butyl, tert-butyl, pentyl, isopentyl, neopentyl, hexyl, isohexyl, heptyl, isoheptyl, octyl, 2,2,4-trimethylpentyl, nonyl, isononyl, decyl, and isodecyl.

More particular values of (1–12C)alkyl containing a double or triple bond include 2-propenyl (i.e. allyl), 2-propynyl, (i.e. propargyl), but-2-enyl, 2-pentenyl, 3-pentenyl, 4-pentenyl, 4-pentynyl, 5-hexenyl, 5-hexynyl, 6-heptenyl, and 6-heptynyl.

More particular values of phenyl substituted with from 0–3 substituents include phenyl; 2- and 4-halophenyl; 2- and 4-aminophenyl; 2- and 4-hydroxyphenyl; 2- and 4-cyanophenyl; 2- and 4-nitrophenyl; 2- and 4-methylphenyl; 2-, 3-, and 4-methoxyphenyl; and 3,5-dihalophenyl and 3,5-dihalo-4-hydroxyphenyl.

More particular values of phenyl(1–4C)alkyl substituted with from 0–3 substituents include benzyl, phenylethyl, 2- and 4-halobenzyl; 2- and 4-cyanobenzyl, 2- and 4-nitrobenzyl, 2- and 4-methylbenzyl; 2- and 4-hydroxybenzyl; 2- and 4-methoxybenzyl; and 3,5-dihalobenzyl, and 3,5-dihalo-4-hydroxybenzyl.

More particular values of pyridyl(1–12C)alkyl include 2-, 3-, and 4-pyridylmethyl, and 2-, 3-, and 4-pyridylethyl.

More particular values of halo include chloro, bromo, and iodo.

More particular values of (1–3C)perfluoroalkyl include trifluoromethyl and pentafluoroethyl.

More particular values of 4- to 7-membered rings containing nitrogen include piperidino and pyrrolidinyl.

More particular values of (1–3C)alkyl substituted with a trifluoromethyl group include trifluoromethylmethyl and 2-trifluoromethylethyl.

More particular values of m include 1–4.

More particular values of n include 1–4.

More particular values of p include 1–4.

Preferred acylating agents of formula $R^8COX'$ include organic carboxylic acid anhydrides (i.e. of formula $R^8CO$—$OOCOR^8$), carboxylic acid halides, especially chlorides, i.e., of formula $R^8COCl$, and carbamoyl halides, especially chlorides, of formula $R^s{}_2NCOCl$ (i.e., where the value for $R^8$ is $NR^s{}_2$).

Preferred values of $R^1$ and $R^2$ include hydrogen, methyl, ethyl, propyl, allyl, propargyl, carboxymethyl, carboxyethyl, carboxypropyl, methoxycarbonylmethyl, methoxycarbonylethyl, ethoxycarbonylmethyl, ethoxycarbonylethyl, aminocarbonylmethyl, aminocarbonylethyl, acetyl, propionyl, phenylacetyl, phenylpropionyl, pyridyl, pyridylacetyl, pivaloyl, isobutyryl, isovaleryl, benzoyl, 2-aminopropionyl, and 2-(1-piperazino)propionyl.

More preferred values of $R^1$ and $R^2$ include hydrogen, methyl, ethyl, carboxymethyl, carboxyethyl, aminocarbonylmethyl, acetyl, phenylacetyl, phenylpropionyl, pivaloyl, isobutyryl, isovaleryl, and benzoyl.

Preferred values of $R^3$ include hydrogen, hydroxy, methoxy, ethoxy, propoxy, thiohydroxy, methylthio, ethylthio, propylthio, amino, carboxymethoxy, carboxyethoxy, carboxypropoxy, methoxycarbonylmethoxy, ethoxycarbonylmethoxy, propoxycarbonylmethoxy, methoxycarbonylethoxy, ethoxycarbonylethoxy, carboxymethylamino, carboxyethylamino, carboxypropylamino, methoxycarbonylmethylamino, ethoxycarbonylmethylamino, propoxycarbonylmethylamino, methoxycarbonylethylamino, ethoxycarbonylethylamino, propoxycarbonylethylamino, methoxycarbonylpropylamino, ethoxycarbonylpropylamino, propoxycarbonylpropylamino, carboxymethylthio, carboxyethylthio, carboxypropylthio, methoxycarbonylmethylthio, ethoxycarbonylmethylthio, propoxycarbonylmethylthio, and methoxycarbonylethylthio, ethoxycarbonylethylthio.

More preferred values of $R^3$ include hydrogen, hydroxy, methoxy, ethoxy, thiohydroxy, methylthio, ethylthio, amino, carboxymethoxy, carboxyethoxy, methoxycarbonylmethoxy, ethoxycarbonylmethoxy, methoxycarbonylethoxy, ethoxycarbonylethoxy, carboxymethylamino, carboxyethylamino, methoxycarbonylmethylamino, ethoxycarbonylmethylamino, methoxycarbonylethylamino, ethoxycarbonylethylamino, carboxymethylthio, carboxyethylthio, methoxycarbonylmethylthio, ethoxycarbonylmethylthio, methoxycarbonylethylthio, and ethoxycarbonylethylthio.

Most preferred values of $R^3$ include hydrogen and those values stated above as more preferred values which have oxygen, nitrogen, or sulfur as the atom through which the remainder of $R^3$ connects to the the ring system, including hydroxy, thiohydroxy, amino, carboxymethoxy, carboxyethoxy, methoxycarbonylmethoxy, ethoxycarbonylmethoxy, carboxymethylamino, carboxyethylamino, methoxycarbonylmethylamino, ethoxycarbonylmethylamino, carboxymethylthio, carboxyethylthio, methoxycarbonylmethylthio, and ethoxycarbonylmethylthio.

Preferred values of $R^4$–$R^7$ include hydrogen, fluoro, chloro, bromo, iodo, amino, methyl, ethyl, propyl, allyl, propargyl, trifluoromethyl, pentafluoroethyl, trifluoromethylmethyl, nitro, methoxy, ethoxy, propoxy, and cyano.

More preferred values of $R^4$–$R^7$ include hydrogen, fluoro, chloro, bromo, iodo, methyl, ethyl, trifluoromethyl, nitro, methoxy, amino, and cyano.

Preferred compounds having formula I include:

(a) 7-chloro-2,3-dihydro-10-hydroxypyridazino[4,5-b]quinoline-1,4-dione;

(b) 7,9-dichloro-2,3-dihydro-10-hydroxypyridazino[4,5-b]-quinoline-1,4-dione;

(c) 7-bromo-2,3-dihydro-10-hydroxypyridazino[4,5-b]quinoline-1,4-dione;

(d) 7,9-dibromo-2,3-dihydro-10-hydroxypyridazino[4,5-b]-quinoline-1,4-dione;

(e) 7-chloro-9-methyl-2,3-dihydro-10-hydroxypyridazino-[4,5-b]quinoline-1,4-dione;

(f) 7-bromo-9-methyl-2,3-dihydro-10-hydroxypyridazino-[4,5-b]quinoline-1,4-dione;

(g) 7-chloro-9-iodo-2,3-dihydro-10-hydroxypyridazino-[4,5-b]quinoline-1,4-dione;

(h) 7-bromo-9-ethyl-2,3-dihydro-10-hydroxypyridazino-[4,5-b]quinoline-1,4-dione;

(i) 2,3-dihydro-10-hydroxypyridazino[4,5-b]quinoline-1,4-dione;

(j) 7-chloro-2,3-dihydropyridazino[4,5-b]quinoline-1,4-dione;

(k) 10-amino-2,3-dihydropyridazino[4,5-b]quinoline-1,4-dione;

(l) 9-ethyl-2,3-dihydro-10-hydroxypyridazino[4,5-b]quinoline-1,4-dione;

(m) 9-chloro-7-methyl-2,3-dihydro-10-hydroxypyridazino-[4,5-b]quinoline-1,4-dione;

(n) 3-acetyl-1-(acetyloxy)-7-chloro-10-hydroxypyridazino-[4,5-b]quinoline-4(3H)-one;

(o) 7-chloro-10-hydroxy-1-(3-phenylpropionyloxy) pyridazino[4,5-b]quinoline-4(3H)-one; and (p) 3-acetyl-1-(acetyloxy)-7,9-dichloro-10-hydroxypyridazino[4,5-b]quinoline-4(3H)-one.

Pyridazinediones of formula I, alkylated and acylated derivatives thereof, can be made by processes which include processes known in the chemical arts for the production of structurally analogous compounds. Such processes for the manufacture of a pyridazinedione of formula I as defined above are provided as further features of the invention and are illustrated by the following procedures in which the meanings of generic radicals are as given above unless otherwise qualified. Such a process can be effected, generally, (a) to obtain an alkylated compound of formula I, by treating a corresponding compound of formula I with a corresponding alkylating agent, such as a halide of formula $R^{12}X$ wherein $R^{12}$ has the value desired for $R^1$ or $R^2$ and X is a conventional leaving group such as chloro, bromo, or iodo. The reaction can be conducted in an appropriate solvent such as dimethylformamide and in the presence of a base such as an alkali metal (for example lithium, potassium, or sodium) carbonate, an alkali metal hydride, or an alkali metal alkoxide such as sodium methoxide or ethoxide;

(b) to obtain an acylated compound of formula I, by treating a corresponding compound of formula I with a corresponding acylating agent of formula $R^8COX'$ wherein $X'$ is a conventional leaving group such as halo (e.g., chloro), a group of formula $OCOR^8$ (i.e., the acylating agent is a (symmetrical) anhydride) or 1-imidazolyl, for example. The reaction can be conducted in an appropriate solvent such as dimethylformamide, pyridine, acetic acid (especially if the acylating agent is an anhydride such as acetic anhydride) or tetrahydrofuran and in the presence of a base such as pyridine (if a different solvent is used) or triethylamine. The reaction can generally be conducted at a temperature of about room temperature to about 100° C. In general, an excess of acylating agent is employed to obtain a monoacylated product (for example a threefold excess) and a larger excess (for example a tenfold excess) is employed to obtain a diacylated or triacylated product. When preparing di- and triacylated products, mixtures can be obtained. The various components can be separated by conventional separation techniques such as chromatography and recrystallization.

(c) to obtain a compound of formula I, by treating a corresponding diester of formula IV, wherein $R^{13}$ is (C1–C3)alkyl, with hydrazine.

(d) to obtain a compound of formula I, by effecting ring closure of a corresponding 2,3-bishydrazinocarbonylquinoline of formula IVa.

(e) to obtain a compound of formula I wherein $R^3$ is amino, by treating a compound of formula IVb with hydrazine.

(f) to obtain an alkylated compound of formula I, by treating a corresponding compound of formula IV with a corresponding substituted hydrazine of formula $R^1HNNHR^2$ wherein $R^1$ and/or $R^2$ correspond to alkyl groups or hydrogen, provided at least one of $R^1$ and $R^2$ is an alkyl group. It is noted that, in general, when unsymmetrical hydrazines are employed, for example where $R^1$ and $R^2$ are different alkyl groups or where a monoalkyl hydrazine is employed, a mixture of alkylated products will be obtained. Such mixtures are separable by standard (for example chromatographic or recrystallization) techniques known to the art and used for the purpose.

(g) to obtain a monoacyl compound of formula I', by hydrolyzing a corresponding diacyl compound of formula I".

(h) to obtain a compound of formula I wherein $R^3$ is carboxyalkylamino, by hydrolyzing a corresponding ester wherein the value of $R^3$ is (1–3C)alkylcarboxyalkylamino.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

A suitable compound of formula I for use in a process as described in (a), (b) or (e) above, can be obtained by reacting a corresponding diester of formula IV with (unsubstituted) hydrazine.

A compound prepared by acylating a compound of formula I with an acylating agent having a value for $R^8$ of $NR^g{}_2$ can be made by treating a compound of formula I wherein $R^3$ is amino with a carbamoyl halide having the formula $XCONR^g{}_2$, wherein X is halogen. Carbamoyl chlorides are preferred. Alternatively, a desired compound wherein one of the values of $R^g$ is hydrogen and the other value is non-hydrogen can be made by treating a compound of formula I, wherein $R^3$ is amino, with an isocyanate having the formula $R^gNCO$. Reaction to make the desired compound of formula I can be conducted in a suitable solvent such as dimethylformamide and at a temperature generally in the range of 85°–115° C.

Certain diesters of formula IV for use in a process as described in (b) above, or for use in reacting with unsubstituted hydrazine to make a compound of formula I for use in (a), can be made by treating a compound of formula V with a suitable base, such as an alkali metal alkoxide (e.g., potassium t-butoxide) in a suitable solvent such as t-butanol to effect ring closure and thereby yield the desired diester. In said compound of formula V the value of Y corresponds to the following to yield a corresponding value for $R^3$ as noted:

a. CHO if a value for $R^3$ of hydrogen is desired;
b. $COOR^{15}$ wherein $R^{15}$ is (C1–C3)alkyl if a value for $R^3$ of hydroxy (or the tautomerically equivalent oxo) is desired; (It is noted that higher alkyl esters can be employed, but they do not provide any synthetic advantage.)
c. $CSOR^{15}$ or $CSSR^{15}$ if a value for $R^3$ of thiohydroxy (SH) is desired; and
d. CN if a value for $R^3$ of amino is desired. The compound of formula V need not be isolated to make the corresponding compound of formula IV. Rather the diester of formula IV can be made in a one-pot process without separating the compound of formula V from the reaction mixture.

A diester of formula IV wherein $R^3$ is hydroxy (or oxo) can also be made by treating an isatoic anhydride of formula VII directly with a sodium or potassium salt of a (C1–C3) dialkyl (e.g. diethyl) ester of 2-oxosuccinic acid in a suitable solvent such as dimethylformamide.

A diester of formula IV wherein $R^3$ is thiohydroxy can be made by treating a corresponding diester of formula IV wherein $R^3$ is hydroxy with Lawesson's reagent, 2,4-bis(4-methoxyphenyl)-1,3-dithia-2,4-diphosphetane-2,4-disulfide, in a suitable solvent such as toluene or dimethoxyethane and at a temperature in the range of 50°–110° C.

A diester of formula IV wherein $R^3$ is alkoxy, thioalkoxy, or alkylamino can be made by alkylating a corresponding diester of formula IV wherein $R^3$ is, respectively, hydroxy, thiohydroxy, or amino. The reaction can be conducted with a suitable corresponding alkylating agent such as an alkyl halide and in a suitable solvent such as dimethylformamide and in the presence of a base such as an alkali metal carbonate. Analogous diesters having values of $R^3$ other than alkoxy can be made using corresponding alkylating agents to conduct analogous reactions. For example, if a compound having a value for $R^3$ of ethoxycarbonylmethoxy is desired, it can be made by alkylating a corresponding compound of formula IV wherein $R^3$ is hydroxy with an alkylating agent having the formula $CH_3CH_2OOCCH_2X$, wherein X is halogen.

A 2,3-bishydrazinocarbonylquinoline of formula IVa can be obtained by reacting an excess of hydrazine with a corresponding diester of formula IV under mild conditions in a suitable solvent (for example, a lower alcohol such as ethanol) and at a temperature of about 20° to about 50° C.

An imide of formula IVb can be made by treating a diester of formula IV, wherein the value corresponding to $R^3$ is a halo group such as chloro or bromo, with ammonia.

A compound of formula V, wherein Y is CN, CHO, COOR[15], CSOR[15] or CSSR[15] can be made by treating a corresponding ortho amine of formula VI with a dialkyl acetylenedicarboxylate, such as dimethyl acetylenedicarboxylate, in a suitable solvent such as a (C1–C4)alcohol. As solvent, t-butanol is preferred.

An ortho amine of formula VI, wherein Y is COOR[15], can be made by esterifying a corresponding acid of formula VIa by conventional methods. An acid of formula VIa can in turn be made by a deprotecting a corresponding compound of formula VIb wherein the amino group has been protected with a conventional protecting group Pr (such as tert-butoxycarbonyl, t-BOC). A compound of formula VIb can in turn be made by sequentially reacting an amide of formula VIc first with two equivalents of an organolithium compound (for example t-butyllithium) to form a dilithiated species which can be carboxylated by reacting with carbon dioxide. An amine of formula VIc can be prepared by protecting a corresponding (unprotected) amine by conventional methods.

An ortho amine of formula VI, wherein Y is COOR[15], can also be made by a process which differs from that described immediately above in that the esterification step is effected by using a base (for example, sodium hydride) followed by an alkylating agent R[15]X on the protected acid of formula VIb rather than on the acid of formula VIa.

An ortho amine of formula VI, wherein Y is COOR[15], can also be made by treating a corresponding isatoic anhydride of formula VII with base (such as an alkali metal hydroxide) in alcoholic solvent of formula R[15]OH.

An isatoic anhydride of formula VII can be made by treating an isatin of formula VIII with chromium trioxide in the presence of acetic anhydride, or with a peroxycarboxylic acid such as the magnesium salt of monoperoxyphthalic acid, and in a suitable solvent such as acetic acid.

An isatin of formula VIII can be made by cyclizing a hydroxyimino acetamide of formula IX in concentrated sulfuric acid at a temperature of 60°–80° C.

A hydroxyimino acetamide of formula IX can be made by treating an amine of formula X with chloral hydrate in the presence of sodium sulfate and hydroxylamine hydrochloride and in a suitable solvent such as water.

It is noted that many of the starting materials for synthetic methods as described above are commercially available and/or widely reported in the scientific literature.

Examples of suitable pharmaceutically acceptable salts are salts formed with bases which form a physiologically acceptable cation, such as alkali metal (especially lithium, sodium and potassium), alkaline earth metal (especially calcium and magnesium), aluminum and ammonium salts, as well as salts made with appropriate organic bases such as choline hydroxide, triethylamine, morpholine, piperidine, ethylenediamine, lysine, ethanolamine, diethanolamine, triethanolamine, N-methyl-D-glucamine (meglumine), arginine, and tris(hydroxymethyl)aminomethane. Choline and meglumine salts are preferred. Choline salts are especially preferred.

When used to intervene therapeutically following a stroke, a pyridazinedione of formula I or an alkylated or acylated derivative thereof generally is administered as an appropriate pharmaceutical composition which comprises a compound according to the invention as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; and in the form of powders together with pharmaceutically acceptable inert solid diluents such as lactose for administration by insufflation.

The dose of a compound according to the invention which is administered will necessarily be varied according to principles well known in the art taking account of the route of administration, the severity of the postischemic disorder, and the size and age of the patient. In general, a compound of according to the invention will be administered to a warm blooded animal (such as man) so that an effective dose is received, generally a dose in the range of about 0.01 to about 100 mg/kg body weight. For example, if the compound is administered intravenously, it is administered in the range of about 0.01 to about 10 mg/kg body weight. If it is administered orally, it is administered in the range of about 0.5 to about 100 mg/kg body weight.

It will be apparent to those skilled in the art that a compound according to the invention can be co-administered with other therapeutic or prophylactic agents and/or medicaments that are not medically incompatible therewith. Compounds within the scope of the invention do not show any indication of untoward side-effects in laboratory test animals at several multiples of the minimum effective dose.

The actions of compounds according to the invention as antagonists at the glycine receptor of the NMDA receptor complex can be shown by one or more standard tests such as the [$^3$H]-glycine binding assay (Test A), by functional assays in vitro such as tests for measuring glutamate-evoked contractions of the guinea pig ileum (Test B) and/or tests for measuring antagonism of of NMDA-induced evoked response in hippocampal slices (Test C), and by tests in vivo such as ischemia induced by carotid occlusion in the gerbil model (Test D).

Test A

In the [$^3$H]-glycine binding assay, neuronal synaptic membranes are prepared from adult (about 250 g) male Sprague-Dawley rats. Freshly dissected cortices and hippocampi are homogenized in 0.32M sucrose (110 mg/mL). Synaptosomes are isolated by centrifugation (1000×g, 10 min), the supernatant is pelleted (20,000×g, 20 min) and resuspended in double-distilled water. The suspension was centrifuged for 20 minutes at 8,000×g. The resulting supernatant and buffy coat are washed twice (48,000×g, 10 mins, resuspension in double-deionized water). The final pellet is quickly frozen (dry ice/ethanol bath) under double-deionized water and stored at −70° C.

On the day of the experiment, thawed synaptic membranes are homogenized with a Brinkmann Polytron (tm, Brinkmann Instruments, Westbury, N.Y.) tissue homogenizer in 50 millimolar tris(hydroxymethyl)aminomethane citrate, pH 7.1. The membranes are incubated with 0.04% Sufact-AMPS X100 (tm, Pierce, Rockford, Ill.) in buffer for 20 minutes at 37° C. and washed six times by centrifugation (48,000×g, 10 min) and resuspended in buffer. The final pellet is homogenized at 200 mg wet weight/mL of the buffer for the binding assay.

For [$^3$H]-glycine binding at the N-methyl-D-aspartate receptor, 20 nanomolar [$^3$H]-glycine (40–60 Ci/mmol, New England Nuclear, Boston, Mass.) is incubated with the membranes suspended in 50 millimolar tris (hydroxymethyl)aminomethane titrate, pH 7.1 for 30 minutes at 4° C. Glycine, 1 millimolar, is used to define the nonspecific binding. Bound [$^3$H]-glycine is isolated from free using a Brandel (Biomedical Research and Development Laboratories, Gaithersburg, Md.) cell harvester for vacuum filtration over glass fiber filters (Whatman GF/B from Brandel, Gaithersburg, Md.) presoaked in 0.025% polyethylenimine. The samples retained on the glass fiber filters are rinsed 3 times with a total of 2.5 mL ice cold buffer. Radioactivity is estimated by liquid scintillation counting. $IC_{50}$ values are obtained from a least-squares regression of a logit-log transformation of the data. Typical $IC_{50}$ values for compounds of the invention are usually less than 100 µM (micromolar) and are illustrated by the compound of Example 2 ($IC_{50}$=0.24 µM), Example 4 ($IC_{50}$=0.08 µM), and Example 11 ($IC_{50}$=8.5 µM)

Test B

For glutamate-evoked contractions of the guinea pig ileum, the methodology is as described previously (Luzzi et. al., Br. J. Pharmacol., 95, 1271–1277 (1989)). The longitudinal muscle and associated myenteric plexus are removed and placed in oxygenated modified Krebs-Henseleit solution (118 millimolar NaCl, 4.7 millimolar KCl, 2.5 millimolar $CaCl_2$, 1.2 millimolar $KH_2PO_4$, 25 millimolar $NaHCO_3$, and 11 millimolar glucose). Tissues are suspended on glass rods in organ baths under a resting tension of 0.5 g. After an initial depolarization with 80 millimolar potassium ion to remove possible blockade of the NMDA receptor channel complex with magnesium, twitch responses are evoked with 100 micromolar glutamate. Isometric mechanical responses are recorded. Tissues are equilibrated for at least 2 hours prior to addition of compounds.

A dose response curve for the effect of the unknown on the magnitude of the glutamate-evoked contractions is generated. Glutamate-evoked contractions are generated at 20 minute intervals, with the test compound added 5 minutes before the glutamate. The magnitude of the contraction with each dose of the unknown is expressed relative to the control, the third contraction evoked by 100 micromolar glutamate alone in the same tissue bath. The $IC_{50}$ is obtained from a least-squares regression of a logit-log transformation of the data.

After the last contraction for the dose-response curve, 100 micromolar glycine is added to the bath 10 minutes after the previous addition of glutamate. Ten minutes later the estimated $IC_{50}$ to $IC_{70}$ dose of the test compound is added and 10 minutes later glutamate is used to evoke the contraction. The "glycine reversal" is the ability of glycine to compete with the unknown and to prevent the inhibition previously seen by the dose of the unknown. Typical $IC_{50}$ values are usually less than 1000 µM and are illustrated by the compound of Example 2 ($IC_{50}$=2.1 µM), Example 4 ($IC_{50}$=2.3 µM), and Example 11 ($IC_{50}$=86 µM).

Test C

The characterization of a compound as a glycine antagonist in the hippocampal slice test (HST) is dependent on (1) the ability of the compound to inhibit NMDA receptor-mediated synaptic transmission in hippocampal slices and (2) the subsequent reversal of these inhibitory effects by D-serine. All the experiments are carried out under conditions of low magnesium ion (Mg++) in order to unmask the NMDA receptor, which at normal Mg++ levels is blocked and therefore does not participate in synaptic transmission.

The procedure for the HST is as follows. Transverse hippocampal slices are obtained from male Sprague-Dawley rats weighting 80–150 gm. The rats are decapitated and the brains quickly removed and placed in cold Krebs-Ringer solution which contains (in millimolar) NaCl (122.6), $NaHCO_3$ (26.2), KCl (5.4), $MgSO_4$ (2.0), $NaH_2PO_4$ (1.2), $CaCl_2$ (2.0), and D-glucose (10.0). The hippocampus is dissected free from surrounding tissues, and 495 micron thick slices are cut and immediately transferred to a humidified static interface chamber with a 95% $O_2$:5% $CO_2$ atmosphere at room temperature. Following a 1-hour equilibration period, slices are placed one at a time into a small perfusion chamber where they are completely submerged in continuously flowing oxygenated 2 millimolar Mg++ perfusate (4 mL/min) at 33° C. and allowed to equilibrate for 10 to 15 min.

For the electrophysiology part of the experiments, bipolar tungsten stimulating electrodes are positioned in the stratum radiatum of the CA3 cell body region of the hippocampus and a single-barrel glass microelectrode filled with Krebs-Ringer solution is positioned in the CA1 cell body region. Low frequency stimulation is then applied to area CA3 which evokes a primary population spike (PS) recorded from CA1. The primary PS represents the summation of a multiple of synaptic potentials mediated via the quisqualate receptor. The stimulus intensity is adjusted to evoke a PS of 1–4 mV amplitude and is maintained at this intensity throughout the experiment.

When the perfusion medium is then changed from 1 millimolar Mg++ to one containing 0 Mg++, the primary PS is followed by the appearance of many secondary PSs. The appearance of the secondary PSs are attributed to the unmasking of NMDA-mediated synaptic events in 0 Mg++. By bathing hippocampal slices in 0 Mg++, drug effects can be qualitatively assessed by measuring the ability of a compound to inhibit the secondary PSs. The effects of directly acting NMDA and indirectly acting NMDA (ie, glycine) receptor antagonists can also be differentiated by the ability of D-serine to reverse this inhibition. Thus, glycine antagonists, such as 7-chlorokynurenic acid and HA-966, will inhibit the secondary PSs and this inhibition is reversed by D-serine, a glycine agonist. In contrast, the inhibition produced by selective competitive NMDA receptor antagonists, such as CPP and APV, or non-competive NMDA receptor antagonists, such as PCP and MK-801, is not reversed by D-serine.

For a particular test compound the HST typically is evaluated at a multiple, for example a multiple of 5, of the $IC_{50}$ concentration obtained in Test B, it being ascertained that the test compound exhibits glycine antagonism at the concentration employed. The HST is accordingly confirmatory of Test B. Typical concentration results are illustrated by the compound of Example 2 (5 µM, antagonist, reversed by D-serine).

Test D

When testing in vivo using the gerbil ischemic model, adult female Mongolian gerbils (50–70 g) are anesthetized with 2 to 3% halothane. The bilateral common carotid arteries at the neck are exposed and occluded with microaneurysm clips. After 10 min (unless specified), the clips are removed and the blood flow through the carotid arteries is restored and the skin is sutured. Test compounds are administered intraperitoneally both pre- and post-occlusion, for example 45 minutes before and 5 minutes after occlusion of the carotid arteries. Sham-operated animals are treated in the same manner except that the arteries are not clamped. Gross behavioral observations along with motor activity are recorded for 2 hr on the first (24 hr) day following the occlusion. After 4 days, subjects are sacrificed (decapitation), brains are removed, fixed, sectioned and stained with hematoxylin/eosin and cresyl violet.

The brain sections are rated for neuronal damage in the hippocampus using the following rating scale:

0=undamaged, normal

1=slight damage (up to 25%)—restricted to CA1/subiculum border

2=moderate damage (up to 50%)—obvious damage, restricted to less than half of CA1 field 3=marked damage (up to 75%)—involving greater than half of CA1 field 4=damage extending beyond CA1 field Sections (7 micron) are evaluated from each brain. Occasionally, asymmetrical damage may be noted and the rating assigned is the average score of the two sides. The average brain damage rating score for each group is recorded, and the damage scores of the drug treated group are compared to the vehicle-treated group using Wilcoxon-Rank Sum test.

Typical values in this test for compounds according to the invention are illustrated by the following results: Over 70% neuroprotection (relative to sham-operated control) for the compounds of Example 2 and Example 4, and over 60% neuroprotection for the compound of Example 11, when each compound was administered intraperitoneally (ip) at a level of 10 mg/Kg body weight according to the above regimen.

The invention will now be illustrated by the following non-limiting examples. It is noted that some of the compound assignments given in the Examples are tentative, and potential alternative structures have been named where applicable; Complete methodology, together with supporting physical and spectroscopic data have been given in such cases. In the Examples, unless stated otherwise:

(i) temperatures are given in degrees Celsius (°C.); operations were carried out at room or ambient temperature, that is, at a temperature in the range of 18°–25° C.;

(ii) evaporation of solvent was carried out using a rotary evaporator under reduced pressure (600–4000 Pascals; 4.5–30 mm Hg) with a bath temperature of up to 60° C.

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, Del., USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) reduced pressures are given as absolute pressures in Pascals (Pa); other pressures are given as gauge pressures in bars;

(ix) chemical symbols have their usual meanings; the following abbreviations have also been used: v (volume), w (weight); mp (melting point), L [liter(s)], mL (milliliters), mM (millimoles), g [gram(s)], mg [milligram(s)], min (minutes), h (hour); and (x) solvent ratios are given in volume: volume (v/v) terms.

(xi) for the Examples which disclose diacylated products, the products are believed to conform to formula I".

EXAMPLE 1

2,3-Dihydro-10-hydroxypyridazino[4,5-b]quinoline-1,4-dione

To a stirred suspension of dimethyl 4-hydroxyquinoline-2,3dicarboxylate (1.00 g, 3.83 mM, prepared as described by H. Biere and W. Seelen, Liebigs Ann. Chem. 1976, 1972) in ethanol (15 mL) was added hydrazine hydrate (9.64 g, 193 mM) whereupon the solids dissolved. The resulting solution was refluxed for 3 hr during which time a thick precipitate formed. The cooled reaction mixture was filtered and the collected yellow solids were washed with ethanol and then ether. Air drying provided 0.99 g of the hydrazine salt of 2,3-dihydro-10-hydroxypyridazino[4,5-b]quinoline-1,4-dione. This material was boiled in glacial acetic acid (40 mL) and, after cooling to room temperature, the mixture was filtered. The collected solids were washed with several portions of ethyl acetate and then ether. Air drying provided the title pyridazinodione (0.72 g, 82%) as a yellow solid, mp >400° C.; Mass Spectrum (Chemical Ionization): 230 (M+H).

Analysis for $C_{11}H_7N_3O_3$: Calculated: C, 57.65; H, 3.08; N, 18.33 Found: C, 57.54; H, 3.26; N, 18.64 250-MHz $^1$H NMR (DMSO-$d_6$): 13.23 (s, 1H, exchangeable), 12.57 (s, 1H, exchangeable), 12.39 (s, 1H, exchangeable), 8.28 (d, J=7.9 Hz, 1H), 8.15 (d, J=8.4 Hz, 1H), 7.94 (t, J=7.5 Hz, 1H), 7.57 (t, J=7.6 Hz, 1H).

EXAMPLE 2

7-Chloro-2,3-dihydro-10-hydroxypyridazino[4,5-b]quinoline-1,4-dione

To a stirred mixture of dimethyl 7-chloro-4-hydroxyquinoline-2,3-dicarboxylate (1.50 g, 5.07 mM) in ethanol (15 mL) was added hydrazine hydrate (12.7 g, 254 mM). The resulting solution was refluxed for 3 hr during which time a thick precipitate formed. The cooled reaction mixture was filtered and the collected yellow solids were washed with ethanol and dried to provide the hydrazine salt of 7-chloro-2,3-dihydro-10-hydroxypyridazino[4,5-b] quinoline-1,4-dione. This material was gently refluxed for 1 hr in acetic acid (40 mL) and, after cooling to room temperature, the mixture was filtered to collect the solids. Drying of the solids under vacuum (50° C.) provided the title pyridazinodione (1.20 g, 90%) as a yellow solid, mp >400° C.: MS(CI): 264 (M+H).

Analysis for $C_{11}H_6ClN_3O_3 \cdot 0.15$ $H_2O$: Calculated: C, 49.61; H, 2.38; N, 15.78 Found: C, 49.57; H, 2.35; N, 15.59 250-MHz $^1$H NMR (DMSO-$d_6$): 13.23 (s, 1H, exchangeable), 12.45 (s, 1H, exchangeable), 12.29 (s, 1H, exchangeable), 8.28 (d, J=9.6 Hz, 1H), 8.18 (s, 1H), 7.59 (d, J=9.6 Hz, 1H).

The starting dimethyl 7-chloro-4-hydroxyquinoline-2,3-dicarboxylate was prepared as follows:

a. Dimethyl 7-chloro-4-hydroxyquinoline-2,3-dicarboxylate

A stirred mixture of methyl 2-amino-4-chlorobenzoate (2.50 g, 13.5 mM) and dimethyl acetylenedicarboxylate (2.05 g, 14.4 mM) in t-butanol (22 mL) was refluxed for 7 hr under a nitrogen atmosphere. After adding additional dimethyl acetylenedicarboxylate (1.16 g, 8.13 mM) and refluxing another 2.5 hr, the reaction mixture was allowed to cool to room temperature and potassium t-butoxide (1.56 g, 13.9 mM) was added in one portion. A precipitate formed and the resulting mixture was refluxed for 1.5 hr. The mixture was cooled to room temperature and filtered to separate the solids, which were washed with t-butanol and ether. The solids were dissolved in water and acidified with 1N sulfuric acid to form a precipitate. The resulting mixture was extracted with methylene chloride and the combined extracts were washed with brine and water, dried (MgSO$_4$), filtered and concentrated to give a green solid. Recrystallization of this material from methanol provided dimethyl 7-chloro-4-hydroxyquinoline-2,3-dicarboxylate (1.15 g, 28.9%) as an off-white solid, mp 232°–233° C.; MS(CI): 296 (M+H).

Analysis for $C_{13}H_{10}ClNO_5$: Calculated: C, 52.81; H, 3.41; N, 4.74 Found: C, 52.75; H, 3.47; N, 4.69

EXAMPLE 3

9-Chloro-2,3-dihydro-10-hydroxypyridazino[4,5-b]quinoline-1,4-dione

To a stirred suspension of dimethyl 5-chloro-4-hydroxyquinoline-2,3-dicarboxylate (0.500 g, 1.69 mM) in ethanol (5 mL) was added hydrazine hydrate (4.2 g, 84.5 mM) whereupon the solids dissolved. The resulting solution was refluxed for 4 hr during which time a precipitate formed. The cooled reaction mixture was filtered and the collected yellow solids were washed with ethanol and dried to give the hydrazine salt of 9-chloro-2,3-dihydro-10-hydroxypyridazino[4,5-b]quinoline-1,4-dione (0.43 g). This material was gently refluxed in acetic acid (15 mL) and, after cooling to room temperature, the mixture was filtered. The collected solids were washed with acetic acid and dried to provide the title pyridazinodione (0.270 g, 60.0%) as a yellow solid, mp >400° C.; MS(CI): 264 (M+H).

Analysis for $C_{11}H_6ClN_3O_3$: Calculated: C, 50.12; H, 2.29; N, 15.94 Found: C, 50.09; H, 2.53; N, 16.13 250-MHz $^1$H NMR (DMSO-d$_6$): 13.18 (s, 1H, exchangeable), 12.58 (s, 1H, exchangeable), 12.42 (s, 1H, exchangeable), 8.12 (d, J=8.4 Hz, 1H), 7.82 (t, J=8.2 Hz, 1H), 7.55 (d, J=7.7 Hz, 1H).

The starting dimethyl 5-chloro-4-hydroxyquinoline-2,3-dicarboxylate was prepared as follows:

a. 5-Chloro-2H-3,1-benzoxazine-2,4(1H)-dione.

To a stirred warm (50° C.) solution of 2-amino-6-chlorobenzoic acid (2.00 g, 11.7 mM) in tetrahydrofuran (20 mL) was added bis(trichloromethyl)carbonate (1.20 g, 4.10 mM). A vigorous gas evolution ensued along with the formation of a precipitate. The reaction mixture was allowed to cool to room temperature and the precipitate was collected by filtration and washed with ether. Air drying gave the title compound as a tan solid (2.0 g, 87%); MS(CI): 198 (M+H).

b. Methyl 2-amino-6-chlorobenzoate.

To a stirred solution of sodium hydroxide (0.14 g, 3.5 mM) in methanol (21 mL) was added 5-chloro-2H-3,1-benzoxazine-2,4(1H)dione (8.5 g, 43.0 mM). The reaction mixture was refluxed for 11.5 hr; an additonal quantity of sodium hydroxide (0.10 g, 2.5 mM) was added and refluxing continued for an additional 4 hr. The resulting solution was, after cooling to room temperature, poured into water which was extracted with ethyl acetate. The combined ethyl acetate extracts were dried (MgSO$_4$), filtered and concentrated to leave methyl 2-amino-6-chloro benzoate as a brown oil (6.50 g, 81.5%); MS(CI): 186 (M+H).

c. Dimethyl 5-chloro-4-hydroxyquinoline-2,3-dicarboxylate.

A solution of methyl 2-amino-6-chlorobenzoate (3.00 g, 16.2 mM) and dimethyl acetylenedicarboxylate (2.64 g, 18.6 mM) in t-butanol (25 mL) was refluxed under a nitrogen atmosphere for 18 hr. The reaction mixture was cooled to room temperature and potassium t-butoxide (2.09 g, 18.6 mM) was added in one portion whereupon a precipitate formed. After refluxing this mixture for 1.5 hr, it was cooled to room temperature and filtered to separate the solids. The solids were dissolved in water and the resulting solution acidified with 1N H$_2$SO$_4$ to form a precipitate. The mixture was filtered and the collected solids were washed with water and air dried to give dimethyl 5-chloro-4-hydroxyquinoline-2,3-dicarboxylate (3.84 g, 80.2%) as a tan solid. An 0.25 g portion of this material was recrystallized from ethyl acetate to provide an analytical sample (0.152 g) of the title compound as an off-white solid, mp 174°–176° C.; MS(CI): 296 (M+H).

Analysis for $C_{13}H_{10}ClNO_5 \cdot 0.01\ H_2O$: Calculated: C, 52.78; H, 3.41; N, 4.73 Found: C, 52.39; H, 3.38; N, 4.67

EXAMPLE 4

7,9-Dichloro-2,3-dihydro-10-hydroxypyridazino[4,5-b]quinoline-1,4dione

A stirred mixture of dimethyl 5,7-dichloro-4-hydroxyquinoline-2,3-dicarboxylate (0.900 g, 2.73 mM) and hydrazine hydrate (6.82 g, 136 mM) in ethanol (10 mL) was refluxed for 3 hr. The resulting mixture was cooled to room temperature and filtered to separate an orange-yellow solid which was washed with ethanol and air dried to give the hydrazine salt of 7,9-dichloro-2,3-dihydro-10-hydroxypyridazino[4,5-b]quinoline-1,4-dione. This material was refluxed in acetic acid (15 mL) for 1 hr and, after cooling to room temperature, the mixture was filtered to collect the solids. These solids were recrystallized from dimethylsulfoxide to provide the title pyridazinedione (0.42 g, 52%) as a yellow solid, mp >395° C.; MS(CI): 298 (M+H).

Analysis for $C_{11}H_5Cl_2N_3O_3 \cdot 0.75\ (CH_3)_2SO$: Calculated: C, 42.09; H, 2.68; N, 11.78 Found: C, 42.42; H, 2.49; N, 11.49 250-MHz $^1$H NMR (DMSO-d$_6$): 13.19 (s, 1H, exchangeable), 12.49 (s, 1H, exchangeable), 12.34 (s, 1H, exchangeable), 8.15 (s, 1H), 7.67 (s, 1H).

The starting dimethyl 5,7-dichloro-4-hydroxyquinoline-2,3-dicarboxylate was prepared as follows:

a. 5,7-Dichloro-2H-3,1-benzoxazine-2,4(1H)-dione.

To a stirred solution of 4,6-dichloro-1H-indole-2,3-dione (5.00 g, 23.2 mM) in acetic acid (21 mL) and acetic anhydride (21 mL) at 80° C. was added in small portions chromium trioxide (4.12 g, 41.3 mM). The temperature of the reaction mixture was maintained between 80°–90° C. during the addition of the chromium trioxide. After the addition was complete, the reaction mixture was diluted with water (100 mL) and then filtered to separate the precipitated solids. The solids were washed thoroughly with water and then dried to obtain the title compound as a yellow solid (4.13 g, 72%); MS(CI): 232 (M+H).

b. Methyl 2-amino-4,6-dichlorobenzoate.

To a stirred solution of sodium hydroxide (0.070 g, 1.8 mM) in methanol (8.5 mL) was added 5,7-dichloro-2H-3,1-benzoxazine-2,4(1H)-dione (4.13 g, 17.8 mM). The reaction mixture was stirred at 55° C. for 2 hr, allowed to cool to room temperature and concentrated. The residue was diluted with water and the resulting mixture extracted with ethyl acetate. The combined extracts were dried (MgSO$_4$), filtered and concentrated to leave the methyl 2-amino-4,6-dichlorobenzoate (3.61 g, 92.1%) as a brown solid; MS(CI): 220 (M+H).

c. Dimethyl 5,7-dichloro-4-hydroxyquinoline-2,3-dicarboxylate.

A solution of methyl 2-amino-4,6-dichlorobenzoate (1.30 g, 5.91 mM) and dimethyl acetylenedicarboxylate (0.96 g, 6.78 mM) in t-butanol (14 mL) was refluxed for 18 hr under a nitrogen atmosphere. The reaction mixture was cooled to room temperature and potassium t-butoxide (0.76 g, 6.8 mM) was added to the stirred mixture whereupon a precipitate formed. After refluxing for 1.5 hr, the reaction mixture was cooled to room temperature and filtered to separate the precipitated solids. The solids were washed with t-butanol and then dissolved in water. The resulting solution was acidified with 1N $H_2SO_4$ and the resulting precipitate was collected, washed thoroughly with water and dried to give the title compound as a light green solid (1.15 g, 59%). An analytical sample was obtained by recrystallization of a portion from toluene to provide the title compound as a light tan solid, mp 109.5°–111° C. (d); MS(CI): 330 (M+H).

Analysis for $C_{13}H_9Cl_2NO_5 \cdot H_2O$: Calculated: C, 44.85; H, 3.18; N, 4.02 Found: C, 44.95; H, 3.23; N, 3.93

EXAMPLE 5

7-Chloro-2,3-dihydro-10-hydroxy-2-methylpyridazino[4,5-b]quinoline-1,4-dione and 7-chloro-2,3-dihydro-10-hydroxy-3-methylpyridazino[4,5-b]quinoline-1,4-dione To a stirred mixture of dimethyl 7-chloro-4-hydroxyquinoline-2,3-dicarboxylate (1.20 g, 4.06 mM) in ethanol (16 mL) was added monomethylhydrazine (1.31 g, 28.4 mM). The resulting solution was refluxed for 6 hr and then cooled to room temperature and filtered to separate a yellow precipitate (1.07 g) which consisted of a mixture of the title compounds in a 4:1 ratio. The major isomer was isolated (0.580 g, 51.8%) by recrystallization of the mixture from acetic acid (630 mL) as light yellow crystals, mp 380°–385° C. (dec); MS(CI): 278 (M+H).

Analysis for $C_{12}H_8ClN_3O_3$: Calculated: C, 51.90; H, 2.90; N, 15.13 Found: C, 51.86; H, 3.07, N, 15.21 250-MHz $^1H$ NMR (DMSO-$d_6$): 13.21 (s, 1H, exchangeable), 12.37 (s, 1H, exchangeable), 8.27 (d, J=8.7 Hz, 1H), 8.20 (s, 1H), 7.58 (d, J=8.7 Hz, 1H), 3.64 (s, 3H).

EXAMPLE 6

2,3-Dihydro-10-hydroxy-9-methylpyridazino[4,5-b]quinoline-1,4-dione

A mixture of dimethyl 4-hydroxy-5-methylquinoline-2,3-dicarboxylate (1.00 g, 3.63 mM) and hydrazine hydrate (9.10 g, 182 mM) in ethanol (15 mL) was refluxed for 3 hr whereupon a yellow precipitate formed. After cooling to room temperature, the reaction mixture was filtered and the collected solids were heated in acetic acid (15 mL) for 1 hr. The resulting mixture was cooled to room temperature and filtered to collect the solids. The solids were washed with acetic acid and then dried at 70° C. under vacuum to give the title pyridazinedione (0.660 g, 75%) as a light yellow crystalline solid, mp >395° C.; MS(CI): 244 (M+H).

Analysis for $C_{12}H_9N_3O_3$: Calculated: C, 59.26; H, 3.73; N, 17.28 Found: C, 59.09; H, 3.92; N, 17.44 250-MHz $^1H$ NMR (DMSO-$d_6$): 12.98 (s, 2H, exchangeable), 12.34 (2, 1H, exchangeable), 7.98 (d, J=8.3 Hz, 1H), 7.73 (t, J=7.9 Hz, 1H), 7.27 (d, J=7.1Hz, 1H), 2.86 (s, 3H).

The starting dimethyl 4-hydroxy-5-methylquinoline-2,3-dicarboxylate was prepared as follows:
a. Dimethyl 4-hydroxy-5-methylquinoline-2,3-dicarboxylate.

A stirred mixture of methyl 2-amino-6-methylbenzoate (1.50 g, 9.08 mM) and dimethyl acetylenedicarboxylate (1.40 g, 9.82 mM) in t-butanol (20 mL) was refluxed fpr 18 hr under a nitrogen atmosphere. The reaction mixture was cooled to room temperature and potassium t-butoxide (1.10 g, 9.82 mM) was added in one portion whereupon a precipitate formed. After refluxing this mixture for 1.5 hr, it was cooled to room temperature and filtered to separate the solids. The solids were dissolved in water and the resulting solution acidified with 1N H2SO4 to form a precipitate. The mixture was filtered and the collected solids were washed with water and dried to give the title compound (1.66 g, 66.4%) as a tan solid. An analytical sample of this material was obtained by recrystallization of a portion from ethyl acetate/hexane to give off white crystals, mp 167°–168° C.; MS(CI): 276 (M+H).

Analysis for $C_{14}H_{13}NO_5 \cdot 0.15\ H_2O$: Calculated: C, 60.50; H, 4.83; N, 5.04 Found: C, 60.45; H, 4.82; N, 4.95

EXAMPLE 7

2,3-Dihydro-10-hydroxy-7-methylpyridazino[4,5-b]quinoline-1,4-dione

Using a procedure similar to that described in Example 6 except starting with dimethyl 4-hydroxy-7-methylquinoline-2,3-dicarboxylate, the title compound was obtained (71%) as light yellow solids, mp >395° C.; MS(CI): 244 (M+H).

Analysis for $C_{12}H_9N_3O_3$: Calculated: C, 59.26; H, 3.73; N, 17.28 Found: C, 59.21; H, 3.86; N, 17.08 250-MHz $^1H$ NMR (DMSO-$d_6$): 13.20 (s, 1H, exchangeable), 12.68 (s, exchangeable), 12.31 (s, 1H, exchangeable), 8.07 (s, 1H), 8.05 (d, J=8.6 Hz, 1H), 7.77 (d, J=8.6 Hz, 1H), 2.49 (s, 3H).

The starting dimethyl 4-hydroxy-7-methylquinoline-2,3-dicarboxylate was prepared as follows:
a. 2-Amino-4-methylbenzoic acid.

To a cold (–78° C.) stirred solution of 2-bromo-5-methylaniline (10.0 g, 53.7 mM) in anhydrous ethyl ether (500 mL) under a nitrogen atmosphere was added t-butyllithium (127 mL of 1.7M solution, 214.8 mM) in pentane over a 15 min period during which time the temperature of the reaction was not allowed to exceed –65° C. After stirring at –78° C. for an additional 1.5 hr, the reaction mixture was quenched with an excess of crushed Dry Ice (solid $CO_2$). After the Dry Ice had evaporated, water was added to the reaction mixture and the organic layer was separated and discarded. The aqueous layer was acidified with 1N hydrochloric acid and then extracted with two portions of ethyl acetate. The combined extracts were dried ($MgSO_4$), filtered and concentrated to provide the title amino acid (4.8 g, 59%) as a tan crystalline solid; MS(CI): 152 (M+H).

b. Methyl 2-amino-4-methylbenzoate.

A solution of 2-amino-4-methylbenzoic acid (5.20 g, 34.3 mM) in methanol (70 mL) was cooled in an ice bath and saturated with hydrogen chloride gas. The resulting solution was refluxed for 3 hr and the cooled and poured into an excess of saturated aqueous sodium bicarbonate. The resulting mixture was extracted with ethyl acetate and the combined extracts were washed with saturated aqueous sodium bicarbonate and then dried ($MgSO_4$), filtered and concentrated to leave the title amino ester (5.66 g, 85.7%) as a brown oil; MS(CI): 166 (M+H).

c. Dimethyl 4-hydroxy-7-methylquinoline-2,3-dicarboxylate.

Using a procedure similar to that described in Example 3c, except starting with methyl 2-amino-4-methylbenzoate, the title diester was obtained (81%) as a tan crystalline solid. An analytical sample was obtained by recrystallization from ethyl acetate to give tan crystals, mp 209°–211°C.; MS(CI): 276 (M+H).

Analysis for $C_{14}H_{13}NO_5$: Calculated: C, 61.09; H, 4.76; N, 5.09 Found: C, 61.19; H, 4.91; N, 5.11

EXAMPLE 8

2,3-Dihydro-7,9-dimethyl-10-hydroxypyridazino[4,5-b]quinoline-1,4dione

To a stirred solution of dimethyl 5,7-dimethyl-4-hydroxyquinoline-2,3-dicarboxylate (0.450 g, 1.56 mM) in ethanol (7 mL) was added hydrazine hydrate (3.90 g, 77.9 mM). The solution was heated with stirring to a temperature of 90° C. for 3 hr during which time a light orange to tan precipitate formed. The cooled reaction mixture was filtered and the collected solids were washed with ethanol and air dried to give 0.32 g of the hydrazine salt of 7,9-Dimethyl-2,3-dihydro-10-hydroxypyridazino[4,5-b]quinoline-1,4-dione. This material was heated in 7–8 mL of acetic acid at 90° C. for 1 hr and the resulting mixture was cooled and filtered to collect the solids which were vacuum dried at 70° C. to provide the title compound (0.260 g, 65%), mp >395° C.; MS(CI): 258 (M+H).

Analysis for $C_{13}H_{11}N_3O_3 \cdot 0.4\ CH_3CO_2H \cdot 0.1H_2O$ Calculated: C, 58.56; H, 4.56; N, 14.84 Found: C, 58.53; H, 4.62; N, 14.96 300-MHz $^1H$ NMR (DMSO-$d_6$): 13.06 (s, 1H, exchangeable), 12.89 (s, 1H, exchangeable), 12.31 (s, 1H, exchangeable), 7.76 (s, 1H), 7.10 (s, 1H), 2.82 (s, 3H), 2.41 (s, 3H).

The starting dimethyl 5,7-dimethyl-4-hydroxyquinoline-2,3-dicarboxylate was prepared as follows:

a. N-(3,5-dimethylphenyl)-2-(hydroxyimino)acetamide.

To a solution of chloral hydrate (14.1 g, 85.24 mM) and sodium sulfate (88.2 g, 7.53 eq.) in 270 mL of water was added a solution of 3,5-dimethylaniline in a solution of concentrated HCl (16 mL) and water (51 mL), whereupon an off-white precipitate formed. The mixture was stirred for 10 min prior to adding an aqueous solution of hydroxylamine hydrochloride (17.4 g, 250 mM) in water (50 mL) and then heated at reflux for 10 min during which time the solids dissolved and a tan precipitate formed. The mixture was cooled and filtered, and the collected solids were air dried to yield the title compound (15.0 g, 95%).

b. 4,6-Dimethyl-1H-indole-2,3-dione.

To a stirred warm (60°–70° C.) solution of concentrated $H_2SO_4$ (60 mL) and water (6 mL) was added in small portions N-(3,5-dimethylphenyl)-2-(hydroxyimino) acetamide (15.0 g, 78 mM) so that the temperature of the reaction mixture did not exceed 70° C. After the addition was completed, the reaction mixture was heated at 80° C. for 10 min and then cooled and poured onto ice. The resulting mixture was filtered and the collected solids were washed with water and dried to provide the title compound (9.93 g, 72.6%); MS(CI): 176.

c. 5,7-Dimethyl-2H-3,1-benzoxazine-2,4(1H)-dione.

To a stirred warm (60° C.) solution of 4,6-dimethyl-1H-indole-2,3-dione (2.0 g, 11.4 mM) in acetic acid (20 mL) was added in small portions chromium trioxide (6.6 g, 66 mM) while maintaining the temperature of the reaction mixture at 65°–70° C. The reaction mixture was then heated at 80° C. for one hour, cooled, poured into water (150 mL) and filtered to obtain the the title compound (0.67 g, 31%) as a light yellow solid; MS(CI): 192 (M+H).

d. Methyl 2-amino-4,6-dimethylbenzoate.

To a stirred solution of sodium hydroxide (0.013 g, 0.33 mM) in methanol (1.7 mL) was added 5,7-dimethyl-2H-3,1-benzoxazine-2,4(1H)-dione (0.67 g, 3.5 mM). The mixture was heated to 60° C. and maintained at that temperature for 45 min during which vigorous gas evolution ensued and all solids dissolved completely. The solution was cooled and concentrated using a rotary evaporator. The residue was dissolved in ethyl acetate, and the ethyl acetate solution was washed with water, dried ($Na_2SO_4$), filtered and concentrated to provide the title compound (0.54 g, 86%) as a tan solid; MS(CI); 180 (M+H).

e. Dimethyl 5,7-dimethylquinoline-4-hydroxy-2,3-dicarboxylate.

A solution of methyl 2-amino-4,6-dimethylbenzoate (0.540 g, 3.0 mM) and dimethyl acetylenedicarboxylate (0.51 g, 3.6 mM) in t-butanol (7 mL) was refluxed under nitrogen for 1.5 hr. The reaction mixture was cooled to room temperature, potassium t-butoxide (0.41 g, 3.61 mM) was added, and the resulting mixture was heated to 90° C. for 1.5 hr during which time solids precipitated out of solution. The mixture was cooled to room temperature, filtered and the collected solids were dissolved in water. The resulting solution was acidified with 1N $H_2SO_4$ whereupon a precipitate formed. The solids were collected and dried to provide the title compound as a tan solid (0.640 g, 73.5%). A 0.140 g portion of this material was recrystallized from hexane/ethyl acetate to provide an analytical sample (0.08 g) of the title compound as a dark tan solid, mp 159°–163° C. (d).

Analysis for $C_{15}H_{15}NO_5 \cdot 0.2\ H_2O$: Calculated: C, 61.51; H, 5.30; N, 4.78; Found: C, 61.45; H, 5.31; N, 4.55;

EXAMPLE 9

2,3-Dihydro-10-hydroxy-7-methoxypyridazino[4,5-b]quinoline-1,4-dione

Using a procedure similar to that described in Example 6 except starting with dimethyl 4-hydroxy-7-methoxyquinoline-2,3-dicarboxylate, the title compound was obtained (87%) as a light yellow crystalline solid, mp 376°–379° C. (d); MS(CI): 260 (M+H).

Analysis for $C_{12}H_9N_3O_4 \cdot 0.01H_2O$: Calculated: C, 55.56; H, 3.50; N, 16.20 Found: C, 55.18; H, 3.60; N, 16.58 300-MHz $^1H$ NMR (DMSO-$d_6$): 12.95 (s, 1H, exchangeable), 12.74 (s, 1H, exchangeable), 12.36 (s, 1H, exchangeable), 8.18 (d, J=9.0 Hz, 1H), 7.60 (d, J=2.4 Hz, 1H), 7.16 (dd, J=9.0, 2.4 Hz, 1H), 3.91 (s, 3H).

The starting dimethyl 4-hydroxy-7-methoxyquinoline-2,3-dicarboxylate was obtained as follows:

a. 2-Nitro-4-methoxybenzoic acid.

A mixture of 2-nitro-4-methoxybenzonitrile (14.0 g, 78.6 mM) in a solution of acetic acid (28 mL), sulfuric acid (28 mL) and water (28 mL) was refluxed for 11 hr, allowed to cool and diluted with water (200 mL). The resulting precipitate which formed was collected, washed with water and dried to give the title benzoic acid (14.2 g, 91.8%) as a yellow crystalline solid; MS(CI): 198 (M+H).

b. 2-Amino-4-methoxybenzoic acid.

A solution of 2-nitro-4-methoxybenzoic acid (14.0 g, 71.0 mM) in 300 mL of ethanol was hydrogenated in the presence of 10% palladium on charcoal using a Parr apparatus. After reduction was completed, the mixture was filtered and the filtrate concentrated to leave the title amino acid (11.7 g, 98.6%) as a lavender crystalline solid; MS(CI): 168 (M+H).

c. Methyl 2-amino-4-methoxybenzoate.

A solution of 2-amino-4-methoxybenzoic acid (11.7 g, 70.0 mM) in methanol (170 mL) was cooled in an ice bath and saturated with hydrogen chloride gas. The resulting solution was refluxed for 18 hr, cooled to room temperature and concentrated. The residue was diluted with saturated aqueous bicarbonate and the resulting mixture extracted with ethyl acetate. The combined extracts were dried ($MgSO_4$), filtered and concentrated to leave the title amino ester (9.2 g, 72.6%) as a tan crystalline solid; MS(CI): 182 (M+H).

d. Dimethyl 4-hydroxy-7-methoxyquinoline-2,3-dicarboxylate.

Using a procedure similar to that described in Example 3c. except starting with methyl 2-amino-4-methoxybenzoate, the title diester was obtained (62%) as a tan crystalline solid. An analytical sample was obtained by recrystallization from ethanol to give tan crystals, mp 202°–204° C.; MS(CI): 292 (M+H).

Analysis for $C_{14}H_{13}NO_6$: Calculated: C, 57.73; H, 4.50; N, 4.81 Found: C, 57.58; H, 4.52; N, 4.59

EXAMPLE 10

2,3-Dihydro-10-hydroxy-9-methoxypyridazino[4,5-b]quinoline-1,4-dione

To a stirred solution of dimethyl 4-hydroxy-5-methoxyquinoline-2,3-dicarboxylate (1.0 g, 3.58 mM) in ethanol (10 mL) was added hydrazine hydrate (8.96 g, 179 mM). The solution was heated with stirring to a temperature of 90°–100° C. for 3 hr during which time a yellow precipitate formed. The cooled reaction mixture was filtered and the collected yellow solids were washed with ethanol and dried to give 0.85 g of the hydrazine salt of 2,3-dihydro-10-hydroxy-9-methoxypyridazino[4,5-b]quinoline-1,4-dione. This material was boiled in acetic acid at for 1 hr and the resulting mixture, after cooling to room temperature, was filtered to separate the solids. These solids were dried and then recrystallized from twice from dimethylsulfoxide to provide the title compound (0.28 g, 30%) as a yellow solid, mp 380°–383° C. (d); MS(CI): 260 (M+H).

Analysis for $C_{12}H_9N_3O_4$: Calculated: C, 55.60; H, 3.50; N, 16.21 Found: C, 55.22; H, 3.50; N, 16.14 300-MHz $^1$H NMR (DMSO-$d_6$): 13.18 (s, 1H, exchangeable), 12.88 (s, 1H, exchangeable), 12.33 (s, 1H, exchangeable), 7.78 (t, J=8.2 Hz, 1H), 7.65 (d, J=8.4 Hz, 1H), 7.00 (d, J=8.2, 1H), 3.91 (s, 3H).

The starting dimethyl 4-hydroxy-5-methoxyquinoline-2,3-dicarboxylate was obtained as follows:

a. 2-amino-6-methoxybenzoic acid

A solution of 6-methoxy-2-nitrobenzoic acid (3.25 g, 16.5 mM) in ethanol (180 mL) containing 10% palladium-on-carbon catalyst (0.30 g) was hydrogenated using a Parr apparatus. When hydrogen consumption ceased, the resulting mixture was filtered through diatomaceous earth and the filtrate concentrated to provide the title benzoic acid (2.76 g, 100%) as a tan solid; MS(CI): 168 (M+H).

b. 5-methoxy-2H-3,1-benzoxazine-2,4(1H)-dione

To a stirred warm (50° C.) solution of 2-amino-6-methoxybenzoic acid (2.70 g, 16.2 mM) in tetrahydrofuran (25 mL) under a nitrogen atmosphere was added bis (trichloromethyl)carbonate (1.60 g, 5.38 mM), whereupon a tan precipitate formed. The reaction mixture was maintained at 50° C. for 30 min, cooled, rewarmed to 50° C. for 30 min, filtered cool and dried to provide the title compound (2.95 g, 94.6%) as an off-white solid; MS(CI): 194 (M+H).

c. Methyl 2-amino-6-methoxybenzoate

To a stirred solution of sodium hydroxide (0.06 g, 1.5 mM) in methanol (7 mL) under a nitrogen atmosphere was added 5-methoxy-2H-3,1-benzoxazine-2,4(1H)-dione (2.90 g, 15.0 mM). The reaction mixture was stirred at 65° C. for 14.5 hr, cooled to room temperature and poured into water. The resulting solution was extracted with ethyl acetate and the combined extracts were dried ($Na_2SO_4$), filtered and concentrated to provide the title compound (2.55 g, 94%) as a tan oil; MS(CI): 182 (M+H).

d. Dimethyl 4-hydroxy-5-methoxyquinoline-2,3-dicarboxylate

A solution of methyl 2-amino-6-methoxybenzoate ((1.30 g, 7.17 mM) and dimethyl acetylenedicarboxylate (1.17 g, 8.23 mM) in t-butanol (11 mL) was refluxed under a nitrogen atmosphere for 4 hr. The reaction mixture was cooled to room temperature, potassium t-butoxide (0.92 g, 8.23 mM) was added, and the resulting mixture was heated to 90° C. for 1.5 hr during which solids precipitated out of solution. The mixture was cooled to room temperature, filtered and the collected solids were dissolved in water. The resulting solution was acidified with 1N $H_2SO_4$ to form a light tan precipitate. The solids were collected, filtered, washed with water and air dried to provide the desired compound (1.35 g, 65%) as a tan solid. A 0.28 g portion of this material was recrystallized from ethyl acetate to provide an analytical sample (0.24 g) of the title compound as a white solid, mp 184°–186° C.; MS(CI): 292 (M+H).

Analysis for $C_{14}H_{13}NO_6 \cdot 0.2\ H_2O$: Calculated: C, 57.03; H, 4.58; N, 4.75 Found: C, 56.99; H, 4.40; N, 4.70

EXAMPLE 11

2,3-Dihydro-10-hydroxy-7-nitropyridazino[4,5-b]quinoline-1,4-dione

Using a procedure similar to that described in Example 6 except starting with dimethyl 4-hydroxy-7-nitroquinoline-2,3-dicarboxylate, the title compound was obtained (56%) as a yellow crystalline solid, mp >400° C., after recrystallization from dimethylsulfoxide; MS(CI): 275 (M+H).

Analysis for $C_{11}H_6N_4O_5 \cdot 1.0\ (CH_3)_2SO$: Calculated: C, 44.32; H, 3.43; N, 15.90 Found: C, 46.32; H, 3.53; N, 15.98 300-MHz $^1$H NMR (DMSO-$d_6$): 13.57 (s, 1H, exchangeable), 12.53 (s, 1H, exchangeable), 12.04 (s, 1H, exchangeable), 9.00 (d, J=2.1 Hz, 1H), 8.50 (d, J=9.0 Hz, 1H), 8.25 (dd, J=9.0, 2.1 Hz, 1H).

The starting dimethyl 4-hydroxy-7-nitroquinoline-2,3-dicarboxylate was obtained as follows:

a. Methyl 2-amino-4-nitrobenzoate.

Using a procedure similar to that described in Example 7b except starting with 2-amino-4-nitrobenzoic acid, the title methyl ester was obtained (89.2%) as an orange crystalline solid; MS(CI): 197 (M+H).

b. Dimethyl 4-hydroxy-7-nitroquinoline-2,3-dicarboxylate.

A stirred mixture of methyl 2-amino-4-nitrobenzoate (6.00 g, 30.6 mM) and dimethyl acetylenedicarboxylate (4.99 g, 35.10 mM) in t-butanol (70 mL) was refluxed for 24 hr under a nitrogen atmosphere. An additonal quantity of dimethyl acetylenedicarboxylate (0.50 g, 3.5 mM) was added to the reaction mixture and refluxing was continued for another 18 hr. After cooling the reaction mixture to room temperature, potassium t-butoxide (3.94 g, 35.1 mM) was added whereupon a precipitate formed. The reaction mixture was refluxed for 1.5 hr, cooled to room temperature and filtered to separate the solids. The solids were added to water and the resulting mixture acidified with 1N $H_2SO_4$. The solids which formed were collected, washed with water and dried to give the title diester (5.41 g, 58%). Recrystallization of a portion of this material from ethanol gave an analytical sample of the d/ester as a green crystalline solid, mp 234.5°–235.5° C.; MS(CI): 307 (M+H).

Analysis for $C_{13}H_{10}N_2O_7$: Calculated: C, 50.99; H, 3.29; N, 9.15 Found: C, 50.83; H, 3.24; N, 9.07

EXAMPLE 12

7-Chloro-2,3-dihydropyridazino[4,5-b]quinoline-1,4-dione

Using a procedure similar to that described in Example 6 except starting with dimethyl 7-chloroquinoline-2,3- dicarboxylate, the title compound was obtained (68%) as a yellow solid, mp 353°–355° C.; MS(CI): 248 (M+H).

Analysis for $C_{11}H_6ClN_3O_2$: Calculated: C, 53.36; H, 2.44; N, 16.97 Found: C, 53.03; H, 2.47; N, 17.16 300-MHz $^1$H NMR (DMSO-d$_6$): 11.65 (br s, 2H, exchangeable), 9.35 (s, 1H), 8.43 (d, J=8.9 Hz, 1H), 8.34 (d, J=1.7 Hz, 1H), 7.87 (dd, J=8.9, 1.7 Hz, 1H).

The starting dimethyl 7-chloroquinoline-2,3-dicarboxylate was prepared as follows:

a. Dimethyl 4,7-dichloroquinoline-2,3-dicarboxylate.

A mixture of dimethyl 7-chloro-4-hydroxyquinoline-2,3-dicarboxylate (5.0 g, 16.9 mM) and phosphorous oxychloride (18 g, 117.4 mM) was heated briefly to 90° C. After cooling to room temperature, the reaction mixture was quenched with ice water and the extracted with ethyl acetate. The combined extracts were dried (MgSO$_4$), filtered and concentrated to leave the title dichloro compound as a crystalline solid. An analytical sample was obtained by recrystallization of a portion from ethyl acetate/hexane to give a tan crystalline solid, mp 113°–114° C.; MS(CI): 314 (M+H).

Analysis for $C_{13}H_9C_{12}NO_4 \cdot 0.5\ H_2O$: Calculated: C, 48.39; H, 3.12; N, 4.53 Found: C, 48.21; H, 2.89; N, 4.34 b. Dimethyl 7-chloroquinoline-2,3-dicarboxylate.

A stirred mixture of dimethyl 4,7-dichloroquinoline-2,3-dicarboxylate (5.00 g, 15.9 mM), sodium formate (1.63 g, 23.9 mM) and tetrakis(triphenylphosphine)palladium(0) (0.92 g, 0.80 mM) in anhydrous dimethylformamide (75 mL) under a nitrogen atmosphere was heated at 90°–95° C. for 7 hr. No reaction occurred so the reaction mixture was degassed and an additional quantity of tetrakis (triphenylphosphine)palladium(0) (0.92 g, 0.80 mM) was added and the reaction mixture again heated at 90°–95° C. for 6 hr. The cooled reaction mixture was poured into water and the resulting mixture extracted with ethyl acetate. The combined extracts were dried (MgSO$_4$), filtered and concentrated to leave an gummy solid (6.0 g). Trituration of this residue with ethyl acetate and subsequent filtration separated a crystalline solid which was shown to be dimethyl 7-chloro-4-hydroxyquinoline-2,3-dicarboxylate. The filtrate was concentrated and the residue was flash chromatographed over silica gel (eluant: hexane/ethyl acetate, 3/2) to provide the title diester (1.13 g, 25.4%) as a light yellow crystalline solid; MS(CI): 280 (M+H). 300-MHz $^1$H NMR (DMSO d6), 9.15 (s, 1H), 8.33 (d, 1H, J=9 Hz), 8.25 (d, 1H, J=2 Hz), 7.86 (dd, 1H, J=9 Hz, 2 Hz), 3.93 (s, 3H), 3.92 (s, 3H).

EXAMPLE 13

10-Amino-2,3-dihydropyridazino[4,5-b]quinoline-1,4-dione

To a stirred solution of dimethyl 4-aminoquinoline-2,3-dicarboxylate (0.15 g, 0.58 mM) in ethanol (4 mL) was added hydrazine hydrate (1.46 g, 29.2 mM) and the resulting solution was refluxed for 3 hr. The reaction mixture was cooled to room temperature and filtered to separate the yellow precipitate (0.12 g). This material was stirred in refluxing acetic acid (4.5 mL) for 1 hr. After cooling to room temperature the react]ion mixture was filtered and the collected solids washed with acetic acid and ethyl acetate. Air drying provided the title compound (0.13 g, 68%) as an orange solid, mp >400° C.; MS(CI): 229 (M+H).

Analysis for $C_{11}H_8N_4O_2 \cdot 1.7\ CH_3CO_2H$: Calculated: C, 52.36; H, 4.52; N, 16.96 Found: C, 52.26; H, 4.55; N, 16.90 300-MHz $^1$H NMR (DMSO-d$_6$): 10.03 (s, 1H, exchangeable), 6.69 (s, 1H, exchangeable), 8.45 (d, J=7.9 Hz, 1H), 7.95 (d, J=8.0 Hz, 1H), 7.84 (t, J=7.7 Hz, 1H), 7.57 (t, J=8.0 Hz, 1H).

The starting dimethyl 4-aminoquinoline-2,3-dicarboxylate was prepared as follows:

a. Dimethyl 2-(2-cyanoanilino)fumarate.

A solution of 2-aminobenzonitrile (5.00 g, 42.3 mM) and dimethyl acetylenedicarboxylate (6.42 g, 45.2 mM) in t-butanol (70.5 mL) was refluxed under a nitrogen atmosphere for 12 hr. After cooling the reaction mixture to room temperature, a precipitate formed and was collected by filtration. The material was washed with cold methanol and air dried to give a yellow solid (4.88 g). Recrystallization of this solid from methanol provided the title compound (4.39 g, 39.9%) as yellow crystals, mp 116.5°–117.5° C.; MS(CI): 261 (M+H).

Analysis for $C_{13}H_{12}N_2O_4$: Calculated: C, 60.00; H, 4.65; N, 10.76 Found: C, 60.03; H, 4.67; N, 10.84 b. Dimethyl 4-aminoquinoline-2,3-dicarboxylate.

To a stirred suspension of dimethyl 2-(2-cyanoanilino)-fumarate (0.50 g, 1.92 mM) in t-butanol under a nitrogen atmosphere was added potassium t-butoxide (0.23 g, 1.92 mM) in one portion whereupon a thick yellow precipitate soon formed. The reaction mixture was heated at 60° C. for 0.5 hr and then at 75° C. for 20 min. After cooling to room temperature, the reaction mixture was poured into water and the reslulting mixture extracted with ethyl acetate. The combined extracts were dried (MgSO$_4$), filtered and concentrated to leave a light purple oil which crystallized to a purple solid. Recrystallization of this material from toluene provided the title diester as a pale purple crystalline solid (0.20 g, 40%), mp 167°–168° C.; MS(CI): 261 (M+H).

Analysis for $C_{13}H_{12}N_2O_4 \cdot 0.02\ C_6H_5CH_3$: Calculated: C, 60.22; H, 4.68; N, 10.69 Found: C, 60.58; H, 4.65; N, 10.55

EXAMPLE 14

2,3-Dihydro-10-hydroxy-7-iodopyridazino[4,5-b]quinoline-1,4-dione

Using a procedure similar to that described in Example 6 except starting with dimethyl 4-hydroxy-7-iodoquinoline-2,3-dicarboxylate, the title compound was obtained (64%) as a yellow solid, mp >395° C., after recrystallization from dimethylsulfoxide; MS(CI): 356 (M+H).

Analysis for $C_{11}H_6IN_3O_3 \cdot (CH_3)_2SO$: Calculated: C, 36.04; H, 2.79; N, 9.70 Found: C, 36.12; H, 2.76; N, 9.83 250-MHz $^1$H NMR (DMSO-d$_6$): 13.17 (s, 1H, exchangeable), 12.45 (s, 1H, exchangeable), 12.35 (s, 1H, exchangeable), 8.55 (d, J=1.2 Hz, 1H), 7.99 (d, J=8.4 Hz, 1H), 7.87 (dd, J=8.4, 1.2 Hz, 1H).

The starting dimethyl 4-hydroxy-7-iodoquinoline-2,3-dicarboxylate was obtained as follows:

a. N-(3-Iodophenyl)-2-(hydroxyimino)acetamide.

Using a procedure similar to that described in Example 8a, except starting with 3-iodoaniline, the title compound was obtained (93%) as a white solid; MS(CI): 291 (M+H).

b. 6-Iodo-1H-indole-2,3-dione.

To stirred warm (60°–65° C.) concentrated sulfuric acid (100 mL) was added in small portions N-(3-iodophenyl)-2-(hydroxyimino)-acetamide (61 g, 210 mM) so that the temperature of the reaction mixture did not exceed 75° C. After the addition was completed, the reaction mixture was heated at 80° C. for 5 min and then cooled and poured onto ice. The resulting mixture was filtered and the collected solids were washed with water and dried to give a mixture of 4-iodo-1H-indole-2,3-dione and 6-iodo-1H-indole-2,3-dione as an orange solid (52 g, 91%).

The desired 6-iodo isomer was separated from the 4-iodo isomer in the following manner:

The isomeric mixture obtained above was dissolved in 2N aqueous sodium hydroxide (750 mL). The resulting dark mixture was filtered to separate a small quantity of undissolved solids and the filtrate was acidified to pH 5.5 with 15% aqueous acetic acid whereupon an orange-red precipitate formed. The mixture was cooled in an ice bath for 1 hr and filtered to separate the resulting solids which consisted entirely of 4-iodo-1H-indole-2,3-dione (36.7 g, 63.6%) as an orange-red solid, mp 259°–260° C.; MS(CI): 274 (M+H). The filtrate was acidified to pH 4 with concentrated hydrochloric acid whereupon an orange precipitate formed. This precipitate was collected, washed with water and dried to give exclusively 6-iodo-1H-indole-2,3-dione (11.2 g, 19.5%) as a light orange solid, mp 272°–273° C.; MS(CI): 274 (M+H).

c. 7-Iodo-2H-3,1-benzoxazine-2,4(1H)-dione.

To a stirred warm (80° C.) solution of 6-iodo-1H-indole-2,3-dione (3.0 g, 11 mM) in acetic acid (10 mL) and acetic anhydride (10 mL) was added in small portions chromium trioxide (1.83 g, 18.3 mM) while maintaining the temperature of the reaction mixture at 80°–90° C. The reaction mixture was then heated at 80° C. for 10 min, cooled and poured into water. The resulting mixture was filtered and the collected solids dried to provide the title compound as a yellow solid (2.6 g, 81.8%); MS(CI): 290 (M+H).

d. Methyl 2-amino-4-iodobenzoate.

To a stirred solution of sodium hydroxide (0.048 g, 1.2 mM) in methanol (4.5 mL) was added 7-iodo-2H-3,1-benzoxazine-2,4(1H)-dione (2.6 g, 9.0 mM). The mixture was heated at 60° C. for 7 hr and the resulting solution was cooled, poured into water and extracted with ethyl acetate. The combined extracts were washed once with dilute sodium hydroxide, dried (MgSO$_4$), filtered and concentrated to leave the title compound (2.0 g, 80%) as a brown oil which slowly crystallized; MS(CI): 278 (M+H).

e. Dimethyl 7-iodo-4-hydroxyquinoline-2,3-dicarboxylate.

Using a procedure similar to that described in Example 3c. except starting with methyl 2-amino-4-iodobenzoate, the crude title diester was obtained as a green solid (2.6 g, 92%). This material was purified by chromatography over silica gel (eluant: methylene chloride/methanol; 9.5/0.5) to provide the title compound (0.85 g, 30%) as a tan solid, mp 243°–244° C.; MS(CI): 388 (M+H).

Analysis for C$_{13}$H$_{10}$INO$_5$: Calculated: C, 40.33; H, 2.60; N, 3.62 Found: C, 40.26; H, 2.77; N, 3.54

EXAMPLE 15

7-Bromo-2,3-dihydro-10-hydroxypyridazino[4,5-b]quinoline-1,4-dione

Using a procedure similar to that described in Example 6 except starting with diethyl 7-bromo-4-hydroxyquinoline-2,3-dicarboxylate, the title compound was obtained (91%) as a light yellow crystalline solid, mp >395° C.; MS(CI): 308 (M+H).

Analysis for C$_{11}$H$_6$BrN$_3$O$_3$.0.1CH$_3$CO$_2$H.0.35 H$_2$O: Calculated: C, 41.98; H, 2.23; N, 13.11 Found: C, 41.98; H, 2.14; N, 13.04 250-MHz $^1$H NMR (DMSO-d$_6$): 13.18 (s, 1H, exchangeable), 12.45 (s, 1H, exchangeable), 12.29 (s, 1H, exchangeable), 8.34 (s, 1H), 8.18 (s, J=8.7 Hz, 1H), 7.70 (d, J=8.7 Hz, 1H).

The starting diethyl 7-bromo-4-hydroxyquinoline-2,3dicarboxylate was prepared as follows:

a. N-(3-Bromophenyl)-2-(hydroxyimino)acetamide.

Using a procedure similar to that described in Example 8a. except starting with 3-bromoaniline, the title compound was obtained (93%) as a tan solid.

b. 6-Bromo-1H-indole-2,3-dione.

Using a procedure similar to that described in Example 14b. except starting with N-(3-bromophenyl)-2-(hydroxyimino)acetamide, The title compound was obtained (28.5%) as an orange solid, mp 278°–278.5° C.

Analysis for C$_8$H$_4$BrNO$_2$.0.57 H$_2$O: Calculated: C, 40.66; H, 2.19; N, 5.93 Found: C, 40.66; H, 2.14; N, 5.96

The isomeric 4-bromo-1H-indole-2,3-dione was also obtained (58.0%) from this reaction in a manner analogous to that described in Example 14b. This material was isolated as an orange-red solid, mp 274.5°–277° C.

Analysis for C$_8$H$_4$BrNO$_2$.0.05 H$_2$O Calculated: C, 42.34; H, 1.82; N, 6.17 Found: C, 42.31; H, 1.77; N, 6.31 c. 7-Bromo-2H-3,1-benzoxazine-2,4(1H)-dione.

Using a procedure similar to that described in Example 14c. except starting with 6-bromo-1H-indole-2,3-dione, the title compound was obtained (82%) as a yellow solid, mp 280°–281° C.; MS(CI): 242, 244 (M+H).

d. Diethyl 7-bromo-4-hydroxyquinoline-2,3-dicarboxylate.

To a stirred mixture of diethyl oxosuccinate sodium salt (1.31 g, 6.23 mM) in dimethylformamide (DMF, 15 mL) under a nitrogen atmosphere was added a solution of 7-bromo-2H-3,1-benzoxazine-2,4(1H)-dione (1.50 g, 6.20 mM) in DMF (15 mL). The resulting reaction mixture was heated to 130° C. over 2.5 hr and then refluxed for 5 hr. After cooling to room temperature, the reaction mixture was concentrated and the residue was chromatographed over silica gel (eluant: ethyl acetate/methylene chloride; 5/95). The fractions containing the desired material were combined and concentrated. The solid residue was recrystallized from ethanol/ether to provide (0.54 g, 24%) the title compound as a tan solid, mp 233.5°–234.5° C.; MS(CI): 368, 369 (M+H).

Analysis for C$_{15}$H$_{14}$BrNO$_5$.0.3 H$_2$O: Calculated: C, 48.22; H, 3.93; N, 3.74 Found: C, 48.13; H, 3.80; N, 3.68

EXAMPLE 16

The diacylated product obtained from the reaction of 7-chloro-2,3-dihydro-10-hydroxypyridazino[4,5-b]quinoline-1,4-dione with acetic anhydride in pyridine A mixture of 7-chloro-2,3-dihydro-10-hydroxypyridazino-[4,5-b]quinoline-1,4-dione (1.60 g, 6.07 mM), as prepared in Example 2, in pyridine (25 mL) and acetic anhydride (25 mL) was refluxed for 1 hr. The resulting mixture was cooled to room temperature, stirred for 3 hr and the filtered. The collected solids were washed successively with acetic anhydride and petroleum ether. The resulting solids were then dried under vacuum at 100° C. to provide (1.78 g, 84%) the title compound as an off-white solid, mp 273°–274° C.

Analysis for C$_{15}$H$_{10}$ClN$_3$O$_5$: Calculated: C, 51.8; H, 2.90; N, 12.08 Found: C, 51.8; H, 3.05; N, 12.14 300-MHz $^1$H NMR (DMSO-d$_6$): 12.99 (br s, 1H, exchangeable), 8.17 (d, J=8.7 Hz, 1H), 8.15 (d, J=2.0 Hz, 1H), 7.52 (dd, J=8.7, 2.0 Hz, 1H), 2.66 (s, 3H), 2.40 (s, 3H).

EXAMPLE 17

1-(Acetyloxy)-7-chloro-10-hydroxypyridazino[4,5-b]quinolin-4(3H)-one

The product obtained in Example 16 (3.0 g, 8.6 mM) was heated to reflux in a solution of 10% acetic anhydride/acetic acid (100 mL) to give a clear yellow solution. The resulting stirred solution was cooled rapidly using an ice bath whereupon a precipitate formed. The mixture was filtered and the collected solids were washed with 10% acetic anhydride/ acetic acid (10 mL). After three days, an additional quantity of solids were obtained from the filtrate by filtration. All solids were combined and recrystallized from 10% acetic anhydride/acetic acid (125 mL) to provide (1.4 g, 53%), after drying in vacuo at 100° C. for 24 hr, the title compound as a light yellow powder (1.4 g, 53%), mp >300° C.

Analysis for $C_{13}H_8ClN_3O_4$: Calculated: C, 51.1; H, 2.64; N, 13.75 Found: C, 50.6; H, 2.80; N, 13.70 300-MHz $^1$H NMR (DMSO-$d_6$): 13.13 (s, 1H, exchangeable), 12.78 (br s, 1H, exchangeable), 8.18 (d, J=8.8 Hz, 1H), 8.12 (d, J=2.0 Hz, 1H), 7.50 (dd, J=8.8, 2.0 Hz, 1H), 2.38 (s, 3H).

EXAMPLE 18

The diacylated product obtained from the reaction of 7-chloro-2,3-dihydro-10-hydroxypyridazino[4,5-b]quinoline-1,4-dione and hydrocinnamoyl chloride in pyridine A mixture of 7-chloro-2,3-dihydro-10-hydroxypyridazino-[4,5-b]quinoline-1,4-dione (0.50 g, 1.9 mM), as prepared in Example 2, and hydrocinnamoyl chloride (1.28 g, 7.6 mM) in pyridine (7.5 mL) was refluxed for 1 hr and then allowed to cool to room temperature whereupon solidification of the reaction mixture occurred. After 2 hr at room temperature, the cooled (methanol/ice bath) mixture was diluted with ice water (25 mL) and the solid mass broken up using a glass rod to provide a free-flowing aqueous suspension. After 5 minutes of stirring, the suspension was filtered and the collected solids were immediately resuspended in 50% aqueous methanol (25 mL, ice cold), stirred rapidly for 5 minutes and filtered. The collected solids were washed with 50% aqueous methanol (10 mL, ice cold) followed by methanol (5 mL, ice cold). The solid was sucked dry on the filter under a stream of nitrogen to give (0.93 g, 93%), after drying in vacuo at 100° C. for 2.5 days, the title compound as a tan solid, mp 277°–279° C.

Analysis for $C_{29}H_{22}ClN_3O_5 \cdot 0.3\ H_2O$:

Calculated: C, 65.3; H, 4.27; N, 7.88 Found: C, 65.3; H, 4.29; N, 7.89 300-MHz $^1$H NMR (DMSO-$d_6$): 13.00 (br s, 1H, exchangeable), 8.19 (d, J=8.7 Hz, 1H), 8.15 (d, J=2.0 Hz, 1H), 7.53 (dd, J=8.7, 2.0 Hz, 1H), 7.35–7.19 (m, 10H), 3.37–3.33 (m, 2H), 3.06–2.95 (m, 6H).

EXAMPLE 19

7-Chloro-10-hydroxy-1-(3-phenylpropionyloxy) pyridazino[4,5-b]quinolin-4(3H)-one A mixture of 7-chloro-2,3-dihydro-10-hydroxypyridazino-[4,5-b]quinoline-1,4-dione (0.60 g, 2.3 mM), as prepared in Example 2, and hydrocinnamoyl chloride (1.15 g, 6.84 mM) in pyridine (9 mL) was refluxed for 1 hr. Upon cooling to room temperature, the solution solidified. After 2 hr at room temperature, the mixture was diluted with water (60 mL) and the solids broken up with a glass rod to provide a free-flowing aqueous suspension which was stirred for 1 hr. The solids were collected, washed with water (10 mL), and resuspended in 50% aqueous methanol (60 mL). After stirring for 15 minutes, this suspension was filtered and the collected solids were washed with 50% aqueous methanol (10 mL) and then sucked dry under a stream of nitrogen to provide a tan solid. This material was dried for 2.5 days in vacuo (50 mTorr) at 100° C. and then was recrystallized from dimethylsulfoxide/methanol. The title compound was obtained (0.40 g, 44%), after drying 24 hr in vacuo (50 mTorr) at 100° C, as an off-white powder, mp >300° C.

Analysis for $C_{20}H_{14}ClN_3O_4 \cdot 0.3\ H_2O$: Calculated: C, 60.0; H, 3.65; N, 10.50 Found: C, 60.1; H, 3.69; N, 10.56 300-MHz $^1$H NMR (DMSO-$d_6$): 13.12 (s, 1H, exchangeable), 12.81 (br s, 1H, exchangeable), 8.19 (d, J=8.7 Hz, 1H), 8.12 (d, J=2.0 Hz, 1H), 7.49 (dd, J=2.0, 8.7 Hz, 1H), 7.36–7.20 (m, 5H), 3.04 (s, 4H).

EXAMPLE 20

6-Chloro-2,3-dihydro-10-hydroxypyridazino[4,5-b] quinoline-1,4-dione

Using a procedure similar to that described in Example 6 except starting with diethyl 8-chloro-4-hydroxyquinoline-2, 3-dicarboxylate, the title compound was obtained (86%) as light yellow solids, mp >390° C.; MS(CI): 264 (M+H).

Analysis for $C_{11}H_6ClN_3O_3$: Calculated: C, 50.12; H, 2.29; N, 15.94 Found: C, 50.05; H, 2.28; N, 16.09 250-MHz $^1$H NMR (DMSO-$d_6$): 12.67 (s, 2H, exchangeable), 11.87 (br s, 1H, exchangeable), 8.25 (d, J=8.3 Hz, 1H), 8.15 (d, J=7.5 Hz, 1H), 7.57 (t, J=8.0 Hz, 1H).

The starting diethyl 8-chloro-4-hydroxyquinoline-2,3-dicarboxylate was prepared as follows:

a. 8-Chloro-2H-3,1-benzoxazine-2,4(1H)-dione.

Using a procedure similar to that described in Example 14c except starting with 7-chloro-1H-indole-2,3-dione, the title compound was obtained (56.4%) as a light yellow solid; MS(CI): 198 (M+H).

b. Diethyl 8-chloro-4-hydroxyquinoline-2,3-dicarboxylate

To a stirred mixture of diethyl oxosuccinate sodium salt (2.31 g, 11.0 mM) in dimethylformamide (20 mL) under a nitrogen atmosphere was added 8-chloro-2H-3,1-benzoxazine-2,4(1H)-dione (2.17 g, 11.0 mM). The resulting mixture was heated slowly to 130° C. and maintained at this temperature for 2.5 hr. After cooling, the reaction mixture was poured into water and the resulting mixture was then extracted with ethyl acetate. The combined organic extracts were washed with water and brine, dried (MgSO$_4$), filtered and concentrated to obtain an oily solid (1.55 g). This material was chromatographed (eluant: $CH_2Cl_2$/ $CH_3OH$; 98/2) over silica gel to provide the title compound as an oil which slowly crystallized to a tan solid (0.700 g, 19.7%). A 0.150 g portion of this material was recrystallized from toluene/hexane to provide an analytical sample (0.050 g) of the title compound as a tan solid, mp 98°–99° C.; MS(CI): 324 (M+H).

Analysis for $C_{15}H_{14}NO_5Cl \cdot 0.1\ C_6H_{14}$ Calculated: C, 56.38; H, 4.67; N, 4.21 Found: C, 56.38; H, 4.83; N, 4.19

EXAMPLE 21

8-Chloro-2,3-dihydro-10-hydroxypyridazino[4,5-b] quinoline-1,4-dione

Using a procedure similar to that described in Example 6 except starting with dimethyl 6-chloro-4-hydroxyquinoline-2,3-dicarboxylate, the title compound was obtained (75%) as a yellow solid, mp >400° C.; MS(CI): 264 (M+H).

Analysis for $C_{11}H_6ClN_3O_3 \cdot 0.15\ H_2O$ Calculated: C, 49.61; H, 2.38; N, 15.78 Found: C, 49.63; H, 2.33; N, 15.63 250-MHz $^1$H NMR (DMSO-$d_6$): 13.35 (s, 1H, exchangeable), 12.44 (s, 1H, exchangeable), 12.26 (s, 1H, exchangeable), 8.19 (d, J=2.0 Hz, 1H), 8.16 (D, J=9.0 Hz, 1H), 7.99 (dd, J=9.0, 2.0 Hz, 1H).

The starting dimethyl 6-chloro-4-hydroxyquinoline-2,3-dicarboxylate was obtained as follows:

a. Methyl 2-amino-5-chlorobenzoate.

Using a procedure similar to that described in Example 9c except starting with 2-amino-5-chlorobenzoic acid, the title compound was obtained (88.9%) as a light tan solid; MS(CI): 186 (M+H).

b. Dimethyl 6-chloro-4-hydroxyquinoline-2,3-dicarboxylate.

Using a procedure similar to that described in Example 11b except starting with methyl 2-amino-5-chlorobenzoate, the title compound was obtained (71.6%) as a tan solid. A 0.25 g portion of this material was recrystallized from methanol to provide 0.16 g of an analytical sample of the diester as a pale yellow crystalline solid, mp 228°–230° C.; MS(CI): 296 (M+H).

Analysis for $C_{13}H_{10}ClNO_5 \cdot 0.2\ H_2O$: Calculated: C, 52.17; H, 3.50; N, 4.68 Found: C, 52.20; H, 3.61; N, 4.50

EXAMPLE 22

2,3-Dihydro-9-ethyl-10-hydroxypyridazino[4,5-b]quinoline-1,4-dione

Using a procedure similar to that described in Example 6 except starting with dimethyl 5-ethyl-4-hydroxyquinoline-2,3-dicarboxylate, the title compound was obtained (76%) as a light yellow solid, mp >400° C.; MS(CI): 258 (M+H).

Analysis for $C_{13}H_{11}N_3O_3$: Calculated: C, 60.70; H, 4.31; N, 16.33 Found: C, 60.47; H, 4.42; N, 16.29 250-MHz $^1$H NMR (DMSO-$d_6$): 13.03 (s, 2H, exchangeable), 12.33 (s, 1H, exchangeable), 8.04 (d, J=8.1 Hz, 1H), 7.79 (t, J=7.6 Hz, 1H), 7.31 (d, J=7.1 Hz, 1m), 3.32 (q, J=7.4 Hz, 2H), 1.23 (t, J=7.4 Hz, 3H).

The starting dimethyl 5-ethyl-4-hydroxyquinoline-2,3-dicarboxylate was prepared as follows:

a. 5-Iodo-2H-3,1-benzoxazine-2,4(1H)-dione.

Using a procedure similar to that described in Example 14c except starting with 4-iodo-1H-indole-2,3-dione (prepared and separated as a byproduct in Example 14b), the title compound was obtained (69.8%) as a yellow solid; MS(CI): 290 (M+H).

b. Methyl 2-amino-6-iodobenzoate.

To a stirred solution of sodium hydroxide (0.35 g, 8.8 mM) in methanol (31 mL) was added 5-iodo-2H-3,1-benzoxazine-2,4(1H)-dione (18.5 g, 64.0 mM). The mixture was heated at 60° C. for 1.5 hr. An additional quantitiy of sodium hydroxide (0.10 g, 2.5 mM) was added to the reaction mixture and stirring at 60° C. was continued for an additonal 1 hr. After cooling to room temperature, the reaction mixture was concentrated and the residue was taken up in ethyl acetate. The ethyl acetate was washed successively with water, brine, dilute aqueous sodium hydroxide, and water. After drying over MgSO4, the ethyl acetate was filtered and concentrated to leave (13.9 g, 78.4%) of the title ester as a brown oil; MS(CI): 278 (M+H).

c. Methyl 2-amino-6-ethylbenzoate.

To a stirred mixture of zinc chloride (8.6 g, 63 mM, previously dried at 200° C. for 2 hr under high vacuum) in tetrahydrofuran (105 mL) under a nitrogen atmosphere was added dropwise a solution of ethyl magnesium chloride (63 mM) in diethyl ether (31.5 mL). After the addition was completed, dichloro[1,1'-bis(diphenylphosphino)ferrocene]palladium(II) (0.107 g, 0.126 mM) was added to the resulting stirred thick white mixture followed by the dropwise addition of methyl 2-amino-4-iodobenzoate (3.5 g, 12.6 mM) in tetrahydrofuran (15 mL). The resulting reaction mixture was stirred at room temperature for 2.5 hr and then poured slowly into water (300 mL). The water mixture was extracted with ethyl acetate and the combined extracts were dried (MgSO4), filtered and concentrated. The residue was chromatographed over silical gel (eluant: Hexanes/diethyl ether; 8.5/1.5) to provide the title ester (1.0 g, 43.5%) as a pale yellow oil; MS(CI): 180 (M+H).

250-MHz $^1$H NMR (DMSO-$d_6$); 7.04 (t, J=7.8, 1H), 6.53 (d, J=8.2, 1H), 6.42 (d, J=7.1, 1H), 5.55 (s, 2H, exchangeable), 3.80 (s, 3H), 2.59 (q, J=7.5, 1H), 1.08 (t, J=7.5, 3H).

d. Dimethyl 5-ethyl-4-hydroxyquinoline-2,3-dicarboxylate.

Using a procedure similar to that described in Example 3c except starting with methyl 2-amino-6-ethylbenzoate, the title diester was obtained (81%) as a brown solid. A 0.20 g portion of this material was recrystallized from ethanol/diethyl ether to provide 0.07 g of an analytical sample as an off-white solid, mp 111°–114° C.; MS(CI): 290 (M+H).

Analysis for $C_{15}H_{15}NO_5 \cdot 1.0\ H_2O$: Calculated: C, 58.63; H, 5.58; N, 4.56 Found: C, 58.43; H, 5.60; N, 4.61

EXAMPLE 23

2,3-Dihydro-10-hydroxy-9-propylpyridazino[4,5-b]quinoline-1,4-dione

Using a procedure similar to that described in Example 6 except starting with dimethyl 4-hydroxy-5-propylquinoline-2,3-dicarboxylate, the title compound was obtained (73%) as a yellow solid, mp >400° C.; MS(CI): 272 (M+H).

Analysis for $C_{14}H_{13}N_3O_3$: Calculated: C, 61.99; H, 4.83; N, 15.49 Found: C, 61.69; H, 4.87; N, 15.40 300-MHz $^1$H NMR (DMSO-$d_6$): 13.03 (s, 2H, exchangeable), 12.34 (s, 1H, exchangeable), 8.03 (d, J=8.3, 1H), 7.76 (t, J=8.0, 1H), 7.27 (d, J=7.2, 1H), 3.25 (t, J=7.4, 2H), 1.60 (m, 2H), 0.96 (t, J=7.4, 3H).

The starting dimethyl 4-hydroxy-5-propylquinoline-2,3-dicarboxylate was prepared as follows:

a. Methyl 2-amino-6-propylbenzoate.

Using a procedure similar to that described in Example 22c except employing n-propyl magnesium chloride, the title compound was obtained (50.6%) as a pale yellow oil; MS(CI): 194 (M+H).

250-MHz $^1$H NMR (DMSO-$d_6$): 7.03 (t, J=8.0, 1H), 6.57 (d, J=8.0, 1H), 6.39 (d, J=8.0, 1H), 5.55 (s, 2H, exchangeable), 3.78 (s, 3H), 2.53 (t, 2H, partially obscured by DMSO peak), 1.45 (m, 2H), 0.86 (t, J=7.5, 3H).

b. Dimethyl 4-hydroxy-5-propylquinoline-2,3-dicarboxylate.

Using a procedure similar to that described in Example 3c except starting with methyl 2-amino-6-propylbenzoate, the title compound was obtained (80%) as a tan solid. A 0.40 g portion of this material was recrystallized from ethanol/diethyl ether to provide an 0.29 g of white crystals as an analytical sample, mp 151°–153° C.; MS(CI): 304.

Analysis for $C_{16}H_{17}NO_5$: Calculated: C, 63.36; H, 5.65; N, 4.62 Found: C, 63.27; H, 5.65; N, 4.58

EXAMPLE 24

7,9-Dichloro-2,3-dihydro-10-hydroxy-8-methoxypyridazino[4,5-b]quinoline-1,4-dione Using a procedure similar to that described in Example 6 except starting with dimethyl 5,7-dichloro-4-hydroxy-6-methoxyquinoline-2,3-dicarboxylate, the title compound was obtained (62%) as an orange-brown solid, after recrystallization from dimethylsulfoxide/water, mp >395° C.; MS(CI): 328 (M+H).

Analysis for $C_{12}H_7Cl_2N_3O_4 \cdot 0.03\ (CH_3)_2SO$: Calculated: C, 43.83; H, 2.19; N, 12.72 Found: C, 43.45; H, 2.28; N, 13.11 250-MHz $^1$H NMR (DMSO-$d_6$): 12.47 (s, 2H, exchangeable), 12.43 (s, 1H, exchangeable), 8.25 (s, 1H), 3.89 (s, 3H).

The starting dimethyl 5,7-dichloro-4-hydroxy-6-methoxyquinoline-2,3-dicarboxylate was prepared as follows:

a. 3,5-Dichloro-4-methoxyaniline.

A stirred mixture of 2,6-dichloro-4-nitroanisole (4.6 g, 21 mM) and tin(II) dichloride dihydrate (23.4 g, 104 mM) in ethanol (72 mL) was refluxed for 3 hr. After cooling to room temperature, the reaction mixture was poured into ice water which was then treated with 2N sodium hydroxide until the solution became basic. The resulting mixture was filtered through diatomaceous earth and the filtrate was extracted with ethyl acetate. The combined ethyl acetate extracts were dried (MgSO$_4$), filtered and concentrated to obtain (3.33 g, 83.7%) the title compound as a yellow-brown solid, mp 80°–81° C.; MS(CI): 192 (M+H).

b. N-(tert-Butoxycarbonyl)-3,5-dichloro-4-methoxyaniline.

A solution of 3,5-dichloro-4-methoxyaniline (7.76 g, 40.4 mM) and di-tert-butyldicarbonate (17.6 g, 80.8 mM) in tetrahydrofuran (38 mL) was stirred under nitrogen at room temperature for 66 hr. The reaction mixture was concentrated and the residue was dissolved in ethyl acetate which was washed successively with 1N sodium hydroxide, brine, and water and then dried (MgSO$_4$), filtered and concentrated to obtain a brown oil (21 g) which slowly crystallized. This material was slurried in hexane and then filtered to separate the desired product as white crystals (7.5 g). An additional quantity of product (2.3 g, total yield=83%) was obtained by chromatography of the residue obtained by concentration of the slurry filtrate over silica gel (eluant: hexane/diethyl ether, 85/15). Recrystallization of a portion of this material from diethyl ether/hexane provided an analytical sample as white crystals, mp 115°–116° C.; MS(CI): 292 (M+H).

Analysis for C$_{12}$H$_{15}$Cl$_2$NO$_3$ Calculated: C, 49.33; H, 5.17; N, 4.79 Found: C, 49.38; H, 5.18; N, 4.74 c. 2-(tert-Butoxycarbonylamino)-4,6-dichloro-5-methoxybenzoic acid.

To a cold (−110° C.) stirred solution of N-(tert-butoxycarbonyl)-3,5-dichloro-4-methoxyaniline (5.0 g, 17.1 mM) in anhydrous tetrahydrofuran (50 mL) under a nitrogen atmosphere was added dropwise a solution of t-butyllithium in pentane [21.1 mL (35.9 mM) of 1.7M solution]. The temperature of the reaction mixture was maintained at −102° to −103° C. during the addition and at −110° to −102° C. for 3.5 after the addition was completed. Crushed Dry Ice was then added to the cold reaction mixture which, after being allowed to warm to −75° C., was poured into water. The resulting mixture was extracted with ethyl acetate and the combined extracts were dried (MgSO$_4$), filtered and concentrated to give a yellow oil (3.5 g). The aqueous layer was saved.

The above yellow oil was redissolved in ethyl acetate which was then extracted five times with 1N sodium hydroxide solution. The combined basic extracts were then acidified with hydrochloric acid and the resulting mixture was extracted with ethyl acetate. The combined extracts were dried (MgSO$_4$), filtered and concentrated to provide a solid which was triturated with hexane and filtered to separate the desired carboxylic acid as white crystals (0.43 g). Since washing with sodium hydroxide did not remove all of the desired carboxylic acid from the ethyl acetate solution, the ethyl acetate was concentrated and the residue chromatographed over silica gel (eluant: methylene chloride/methanol: 9/1) to provide an additional portion (0.63 g) of the desired carboxylic acid as white crystals.

The original aqueous layer which was saved was acidified with hydrochloric acid and the resulting mixture extracted with ethyl acetate. The combined ethyl acetate extracts were dried (MgSO$_4$), filtered and concentrated to leave a white oily solid. Trituration of this material with diethyl ether/hexane provided an additional quantity (2.16 g, total yield=3.2 g, 56%) of the title carboxylic acid as white crystals. Recrystalization of a portion of this material from diethyl ether/hexane provided an analytical sample of the title carboxylic acid as white crystals, mp 135°–136° C.; MS(CI); 336 (M+H).

Analysis for C$_{13}$H$_{25}$Cl$_2$NO$_5$ Calculated: C, 46.45; H, 4.50; N, 4.17 Found: C, 46.73; H, 4.62; N, 4.22 d. Methyl 2-(tert-butoxycarbonylamino)-4,6-dichloro-5-methoxybenzoate.

To a cold (ice bath) stirred solution of 2-(tert-butoxycarbonylamino)-4,6-dichloro-5-methoxybenzoic acid (2.0 g, 5.9 mM) in 20 mL of dry dimethylformamide under a nitrogen atmosphere was added sodium hydride (0.24 g, 5.9 mM); a precipitate formed which slowly redissolved on stirring. To the resulting stirred solution was added iodomethane (8.4 g, 59 mM). After stirring at room temperature for 1.5 hr, the reaction mixture was poured into water and the resulting mixture extracted with ether. The combined ether extracts were washed with brine, dried (MgSO$_4$), filtered and concentrated to leave the title compound as a yellow oil (2.0 g, 96%); MS(CI): 350 (M+H).

300-MHz $^1$H NMR (DMSO-d$_6$): 9.33 (s, 1H), 7.52 (s, 1H), 3.81 (s, 6H), 1.44 (s, 9H)

e. Methyl 2-amino-4,6-dichloro-5-methoxybenzoate.

A solution of methyl 2-(tert-butoxycarbonylamino)-4,6-dichloro-5-methoxybenzoate (2.3 g, 6.6 mM) and trifluoroacetic acid (6.0 g, 53 mM) in methylene chloride (23 mL) was stirred at room temperature for 1.5 hr. The reaction mixture was then washed with saturated aqueous sodium bicarbonate, drie (MgSO$_4$), filtered and concentrated to obtain (87%) the title compound as a yellow oil; MS(CI): 250 (M+H).

250-MHz $^1$H NMR (DMSO-d$_6$): 6.82 (s, 1H), 5.71 (s, 2H), 3.83 (s, 3H), 3.68 (s, 3H).

f. Dimethyl 5,7-dichloro-4-hydroxy-6-methoxyquinoline-2,3-dicarboxylate.

Using a procedure similar to that described in Example 3c except starting with methyl 2-amino-4,6-dichloro-5-methoxybenzoate, the title compound was obtained (61%) as a tan solid. A portion of this material was recrystallized from ethyl acetate to provide an analytical sample of the title diester as light tan crystals, mp 210°–211° C.; MS(CI): 360 (M+H).

Analysis for C$_{14}$H$_{11}$Cl$_2$NO$_6$·1.0 H$_2$O Calculated: C, 44.47; H, 3.46; N, 3.70 Found: C, 44.40; H, 3.44; N, 3.61

EXAMPLE 25

2,3-Dihydro-10-hydroxy-7,8,9-trichloropyridazino[4,5-b]quinoline-1,4-dione

Using a procedure similar to that described in Example 6 except starting with dimethyl 4-hydroxy-5,6,7-trichloroquinoline-1,4-dicarboxylate, the title compound was obtained (44%) as tan solid. Recrystallization from dimethylsulfoxide provided an analytical sample of the title compound as a yellow-brown solid, mp >390° C.; MS(CI): 332 (M+H).

Analysis for C$_{11}$H$_4$Cl$_3$N$_3$O$_3$·1.0 (CH$_3$)$_2$SO Calculated: C, 38.02; H, 2.45; N, 10.23 Found: C, 37.94; H, 2.46; N, 10.36 250-MHz $^1$H NMR (DMSO-d$_6$): 13.25 (s, 1H, exchangeable), 12.52 (s, 1H, exchangeable), 12.23 (s, 1H, exchangeable), 8.33 (s, 1H).

The starting dimethyl 4-hydroxy-5,6,7-trichloroquinoline-1,4-dicarboxylate was prepared as follows:

a. N-(tert-Butoxycarbonyl)-3,4,5-trichloroaniline.

A solution of 3,4,5-trichloroaniline (5.0 g, 25.5 mM) and di-tert-butyldicarbonate (8.35 g, 38.3 mM) in tetrahydrofuran (25 mL) was refluxed 24 hr, cooled and concentrated. The residue was chromatographed over silica gel (eluant: hexane/diethyl ether: 9.5/0.5→9.0/1.0) to provide (4.7 g, 62%) the title compound as white crystals, mp 119.5°–120.5° C.

Analysis for $C_{11}H_{12}Cl_3NO_2$ Calculated: C, 44.55; H, 4.08; N, 4.72 Found: C, 44.47; H, 4.08; N, 4.64 b. 2-(tert-Butoxycarbonylamino)-4,5,6-trichlorobenzoic acid.

To a cold (–110° C.) stirred solution of N-(tert-butoxycarbonyl)3,4,5-trichloroaniline (2.0 g, 6.7 mM) in tetrahydrofuran (20 mL) was added dropwise t-butyllithium (8.3 mL of 1.7M solution, 14.2 mM) in pentane. The temperature of the reaction mixture was maintained at –100° to –110° C. during the addition and then at –110° C. for 3.5 hr after the addition was completed. Crushed Dry Ice was then added to the cold reaction mixture which, after being allowed to warm to –75° C., was poured into water. The resulting mixture was extracted with ether and the combined extracts were dried (MgSO$_4$), filtered and concentrated. The aqueous layer was saved.

The residue obtained from the ether extracts was chromatographed over silica gel (eluant: methylene chloride/methanol; 96/4) to provide the title carboxylic acid (0.40 g) as a white solid.

The original aqueous layer was acidified with 1N hydrochloric acid and extracted with ether. The combined ether extracts were dried (MgSO$_4$), filtered and concentrated. The residue was chromatographed over silica gel (eluant: methylene chloride/methanol; 96/4) to provide a white solid. This solid was triturated with hexane (to remove pivalic acid) and filtered to separate (0.55 g, total yield=41%) the title compound as a white solid. Recrystallization of a portion of this material from diethyl ether/hexane provided an analytical sample of the title carboxylic acid as white crystals, mp 135°–137° C. (dec).

Analysis for $C_{12}H_{12}NO_4Cl_3.1.25\ H_2O$ Calculated: C, 39.69; H, 4.02; N, 3.86 Found: C, 39.48; H, 3.62; N, 3.62 c. Methyl 2-(tert-butoxycarbonylamino)-4,5,6-trichlorobenzoate.

Using a procedure similar to that described in Example 24d except starting with N-(tert-butoxycarbonyl)-3,4,5-trichloroaniline, the title compound was obtained (74%) as a white solid after chromatography over silica gel (eluant: hexanes/diethyl ether: 9/1). An analytical sample of the title carboxylic acid methyl ester was obtained by recrystallization from ether as white crystals, mp 141.5°–142.5° C.

Analysis for $C_{13}H_{14}Cl_3NO_4$ Calculated: C, 44.03; H, 3.98; N, 3.95 Found: C, 44.29; H, 4.10, N, 3.87 d. Methyl 2-amino-4,5,6-trichlorobenzoate.

Using a procedure similar to that described in Example 24e except starting with methyl 2-(tert-butoxycarbonylamino)-4,5,6-trichlorobenzoate, the title compound was obtained (98%) as a white solid. Recrystallization of a portion of this material from hexane/diethyl ether provided an analytical sample as white crystals, mp 123°–124° C.

Analysis for $C_8H_6Cl_3NO_2$ Calculated: C, 37.76; H, 2.38; N, 5.50 Found: C, 37.90; H, 2.40; N, 5.47 e. Dimethyl 4-hydroxy-5,6,7-trichloroquinoline-2,3-dicarboxylate.

Using a procedure to that described in Example 11b except starting with methyl 2-amino-4,5,6-trichlorobenzoate, the title compound was obtained (87%) as a tan solid. Recrystallization of a portion of this material from diethyl ether provided an analytical sample of the title diester as tan crystals, mp 227°–228° C.; MS(CI): 364 (M+H).

Analysis for $C_{13}H_8Cl_3NO_5$ Calculated: C, 42.83; H, 2.21; N, 3.84 Found: C, 42.60; H, 2.34; N, 3.80

EXAMPLE 26

7-Bromo-2,3-dihydro-9-ethyl-10-hydroxypyridazino [4,5-b]quinoline-1,4-dione

Using a procedure similar to that described in Example 6 except starting with dimethyl 7-bromo-5-ethyl-4-hydroxyquinholine-2,3-dicarboxylate, the title compound was obtained (60%) as tan solids, mp 380°–382° C.; MS(CI): 336 (M+H).

Analysis for $C_{13}H_{10}BrN_3O_3.1.0\ CH_3CO_2H$ Calculated: C, 45.47; H, 3.56; N, 10.61 Found: C, 45.52; H, 3.58; N, 10.77 250-MHz $^1$H NMR (DMSO-d$_6$): 13.0 (s, 1H, exchangeable), 12.8 (s, 1H, exchangeable), 12.39 (s, 1H, exchangeable), 8.23 (s, 1H), 7.48 (s, 1H), ~3.29 (obscured by water peak), 1.21 (t, J=7.2 Hz, 3H).

The starting dimethyl 7-bromo-5-ethyl-4-hydroxyquinoline-2,3-dicarboxylate was prepared as follows:

a. 3-Bromo-5-ethylaniline.

Using a procedure similar to that described in Example 24a except starting with 3-bromo-5-ethyl nitrobenzene (prepared according to the method described by P. Leeson in European Patent Application 0303387 A1, 1988), the title compound was obtained (74%) as a light yellow oil; MS(CI): 200 (M+H).

250-MHz $^1$H NMR (CDCl$_3$): 6.73 (s, 1H), 6.65 (s, 1H), 6.42 (s, 1H), 3.65 (bs, 2H, exchangeable), 2.50 (q, J=7.5 Hz, 2H), 1.18 (t, J=7.5 Hz, 3H).

b. N-(3-Bromo-5-ethylphenyl)-2-(hydroxyimino)acetamide.

Using a procedure similar to that described in Example 8a except starting with 3-bromo-5-ethylaniline, the title compound was obtained (91%) as a tan solid. Recrystallization of a portion of this material from toluene provided an analytical sample of the title compound as tan crystals, mp 176.5°–177.5° C.; MS(CI): 271 (M+H).

Analysis for $C_{10}H_{11}BrN_2O_2$ Calculated: C, 44.30; H, 4.09; N, 10.33 Found: C, 44.30; H, 4.16; N, 10.23 c. 6-Bromo-4-ethyl-1H-indole-2,3-dione.

To a stirred warm (65°–75° C.) solution of concnetrated sulfuric acid (29 mL) was added in small portions N-(3-bromo-5-ethylphenyl)-2-(hydroxyimino)acetamide (16.36 g, 60.4 mM) so that the temperature of the reaction mixture was maintained at 65°–75° C. After the additon was completed, the reaction mixture was heated at 80° C. for 10 min and then cooled and poured into ice. The resulting mixture was extracted with ethyl acetate and the combined extracts were dried (MgSO4), filtered and concentrated to leave an orange solid (15 g) which consisted of two isomeric 1H-indole-2,3-diones. The isomers were separated by chromatography (eluant: hexane, then hexane/ethyl acetate; 8/2) to provide (3.05 g, 20%) the title compound as a yellow solid. Trituration of a portion of this material with hexane/acetone provide an analytical sample of the title compound as yellow crystals, mp 229°–230.5° C.; MS(CI): 254 (M+H).

Analysis for $C_{10}H_8BrNO_2$ Calculated: C, 47.27; H, 3.17; N, 5.51 Found: C, 47.11; H, 3.27; N, 5.64

The isomeric compound, 4-bromo-6-ethyl-1H-indole-2,3-dione, was isolated (11.7 g, 76.5%) from the above chromatography as an orange solid. Recrystallization of a portion of this material from ethyl acetate provide an analytical sample as orange crystals, mp 219°–220° C.; MS(CI): 254 (M+H).

Analysis for $C_{10}H_8BrNO_2$ Calculated: C, 47.27; H, 3.17; N, 5.51 Found: C, 47.11; H, 3.27; N, 5.50 d. 7-Bromo-5-ethyl-2H-3,1-benzoxazine-2,4(1H)-dione.

A stirred solution of 6-bromo-4-ethyl-1H-indole-2,3-dione (2.64 g, 10.4 mM) and the hexahydrate magnesium salt of monoperoxyphthalic acid (80% pure, 3.54 g, 5.73 mM) in glacial acetic acid (30 mL) was stirred at 60° C. for 1 hr during which time a precipitate formed. The cooled reaction mixture was then poured into cold water and the resulting mixture was filtered to separate (2.04 g, 73%) the title compound as a tan solid. Recrystallization of a portion of this material from ethyl acetate/hexane provided an analytical sample of the title compound as off white crystals, mp 208.5°–210.5° C.; MS(CI): 270 (M+H).

Analysis for $C_{10}H_8BrNO_3$ Calculated: C, 44.49; H, 2.99; N, 5.19 Found: C, 44.32; H, 3.05; N, 5.14 e. Methyl 2-amino-4-bromo-6-ethylbenzoate.

Using a procedure similar to that described in Example 8d except starting with 7-bromo-5-ethyl-2H-3,1-benzoxazine-2,4(1H)-dione, the title compound was obtained (94%) as a light brown oil; MS(CI): 258 (M+H).

300-MHz $^1$H NMR (DMSO-$d_6$): 6.80 (d, J=1.9 Hz, 1H), 6.59 (d, J=1.9 Hz, 1H), 5.85 (s, 2H), 3.79 (s, 3H), 2.58 (q, J=7.5 Hz, 2H), 1.07 (t, J=7.5 Hz, 3H).

f. Dimethyl 7-bromo-5-ethyl-4-hydroxyquinoline-2,3-dicarboxylate.

Using a procedure similar to that described in Example 3c except starting with methyl 2-amino-4-bromo-6-ethylbenzoate, the title compound was obtained (90%) as a light green solid. A portion of this crude material was chromatographed (eluant: methylene chloride/ethyl acetate; 85/15) over silica gel and recrystallized from toluene/diethyl ether to provide an analytical sample, mp 115°–117° C.; MS(CI): 368 (M+H).

Analysis for $C_{15}H_{14}BrNO_5 \cdot 1.0\ H_2O$ Calculated: C, 46.65; H, 4.18; N, 3.63 Found: C, 46.69; H, 4.17; N, 3.64

EXAMPLE 27

7,9-Ditrifluoromethyl-2,3-dihydro-10-hydroxypyridazino[4,5-b]quinoline-1,4-dione Using a procedure similar to that described in Example 6 except starting with dimethyl 5,7-ditrifluoromethyl-4-hydroxyquinoline-2,3dicarboxylate and diluting the acetic acid solution with water to effect product precipitation, the title compound was obtained as a tan solid, mp >385° C.; MS(CI): 366 (M+H).

Analysis for $C_{13}H_5F_6N_3O_3$ Calculated: C, 42.76; H, 1.38; N, 11.51 Found: C, 42.59; H, 1.46; N, 11.28 250-MHz $^1$H NMR (DMSO-$d_6$): 13.60 (s, 1H, exchangeable), 12.59 (s, 1H, exchangeable), 12.08 (s, 1H, exchangeable), 8.88 (s, 1H), 8.11 (s, 1H).

The starting dimethyl 5,7-ditrifluoromethyl-4-hydroxyquinoline-2,3-dicarboxylate was prepared as follows:

a. N-(tert-Butoxycarbonyl)-3,5-ditrifluoromethylaniline.

A solution of 3,5-trifluoromethylaniline (10.0 g, 43.6 mM) and di-tert-butyldicarbonate (13.3 g, 61 mM) in tetrahydrofuran (40 mL) was refluxed under a nitrogen atmosphere for 4 days and then concentrated. The residue was chromatographed (eluant: hexane/di-ethyl ether/95/5→90/10) over silica gel to provide (70%) the title compound as a white solid. Recrystallization of a portion of this material from diethyl ether/hexanes provided an analytical sample of the title compound as white crystals, mp 141.5°–142.5° C.

Analysis for $C_{13}H_{13}F_6NO_2$ Calculated: C, 47.43; H, 3.98; N, 4.25 Found: C, 47.46; H, 4.00; N, 4.20 b. 2-(tert-Butoxycarbonylamino)-4,6-ditrifluoromethylbenzoic acid.

To a cold (−78° C.) stirred solution of N-(tert-butoxycarbonyl)-3,5-ditrifluoromethylaniline (5.0 g, 15 mM) in tetrahydrofuran (50 mL) under a nitrogen atmosphere was added dropwise t-butyllithium (18.75 mL of 1.7M solution, 31.88 mM) in pentane. After the additon was competed, the reaction mixture was stirred at −78° C. for 2.25 hr and then quenched by adding crushed Dry Ice. After stirring for 20 min, the reaction mixture was poured into water and the resulting mixture extracted with ethyl acetate. The combined organic extracts were dried (MgSO4), filtered and concentrated. The residue was chromatographed (eluant: methylene chloride/methanol; 8/2→8.5/1.5) over silica gel to provide (2.9 g, 51%) the title compound as a solid foam.

250-MHz $^1$H NMR (DMSO-$d_6$): 9.59 (s, 1H), 8.14 (s, 1H), 7.38 (s, 1H), 1.48 (s, 9H).

c. Methyl 2-(tert-butoxycarbonylamino)-4,6-ditrifluoromethylbenzoate.

To a cold (ice bath) stirred solution of 2-(tert-butoxycarbonyl-amino)-4,6-ditrifluoromethylbenzoic acid (2.0 g, 5.3 mM) in dimethylformamide (20 mL) under a nitrogen atmosphere was added sodium hydride (0.21 g of 60% mineral oil suspension, 5.3 mM) and then, after 5 min had elapsed, iodomethane (7.61 g, 53.5 mM). After stirring for 1 hr, the reaction mixture was poured into water and the resulting mixture extracted with ether. The combined ether extracts were dried (MgSO$_4$), filtered and concentrated. The residue was chromatographed (eluant: hexane/diethyl ether; 9/1) over silica gel to provide (0.80 g, 39%) the title compound as a clear oil.

250-MHz $^1$H NMR (DMSO-$d_6$): 9.67 (s, 1H), 8.13 (s, 1H), 7.90 (s, 1H), 3.84 (s, 3H), 1.48 (s, 9H).

d. Methyl 2-amino-4,6-ditrifluoromethylbenzoate.

Using a procedure similar to that described in Example 24e except starting with methyl 2-(tert-butoxycarbonylamino)-4,6-ditrifluoromethylbenzoate, the title compound was obtained (90%) as an amber oil; MS(CI): 288 (M+H).

250-MHz $^1$H NMR (DMSO-$d_6$): 7.38 (s, 1H), 7.11 (s, 1H), 6.29 (s, 2H), 3.86 (s, 3H).

e. Dimethyl 5,7-ditrifluoromethyl-4-hydroxyquinoline-2,3-dicarboxylate.

Using a procedure similar to that describe in Example 3c except starting with methyl 2-amino-4,6-ditrifluoromethylbenzoate, the title compound was obtained (57%) as a brown solid. A portion of this material was chromatographed (eluant: methylene chloride/methanol; 95/5) to provide an analytical sample as tan drystals, mp 105.5°–107.5° C.; MS(CI): 398 (M+H).

Analysis for $C_{15}H_9F_6NO_5 \cdot 1.0\ H_2O$ Calculated: C, 43.39; H, 2.67; N, 3.37 Found: C, 43.29; H, 2.63; N, 3.31

EXAMPLE 28

9-Chloro-2,3-dihydro-10-hydroxy-7-trifluoromethylpyridazino[4,5-b]-quinoline-1,4-dione Using a procedure similar to that described in Example 6 except starting with dimethyl 5-chloro-4-hydroxy-7-trifluoromethylquinoline-2,3-dicarboxylate, the title compound was obtained, after recrystallization from dimethylsulfoxide, as yellow-orange solids, mp 375°–380° C. (dec); MS(CI): 332 (M+H).

Analysis for $C_{12}H_5ClF_3N_3O_3 \cdot 0.3\ (CH_3)_2SO \cdot 1.0\ H_2O$ Calculated: C, 40.56; H, 2.38; N, 11.26 Found: C, 40.42; H, 2.73; N, 11.52 250-MHz $^1$H NMR (DMSO-$d_6$): 12.54 (s, 2H, exchangeable), 12.19 (s, 1H, exchangeable), 8.50 (s, 1H), 7.89 (s, 1H).

The starting dimethyl 5-chloro-4-hydroxy-7-trifluoromethylquinoline-2,3-dicarboxylate was prepared as follows:

a. 3-Chloro-5-trifluoromethylnitrobenzene.

To a stirred solution of 2-chloro-6-nitro-4-trifluoroaniline (20.0 g, 83.1 mM) in ethanol (110 mL) was added dropwise concentrated sulfuric acid (12.6 mL). The resulting stirred solution was heated to reflux and sodium nitrite (14.34 g, 207.9 mM) was added in portions, whereupon a precipitate formed. After the addition was completed, the reaction mixture was refluxed for 3 hr, cooled and poured into water. The resulting mixture was extracted with ether and the combined extracts were dried ($MgSO_4$), filtered and concentrated. The residue was chromatographed (eluant: hexane/diethyl ether; 98/2→80/20) over silica gel to provide (10.9 g, 58%) the title compound as a yellow oil: MS(CI): 226 (M+H).

300-MHz $^1$H NMR (DMSO-$d_6$): 8.62 (s, J=2.0 Hz, 1H), 8.47 (m, 2H).

b. 3-Chloro-5-trifluoromethylaniline.

Using a procedure similar to that described in Example 24a except starting with 3-chloro-5-trifluoromethylnitrobenzene, the title compound was obtained (77%) as an amber oil; MS(CI): 196 (M+H).

250-MHz $^1$H NMR (DMSO-$d_6$): 6.82 (s, 1H), 6.79 (s, 1H), 6.77 (s, 1H), 5.94 (s, 2H).

c. N-(tert-Butoxycarbonyl)-3-chloro-5-trifluoromethylaniline.

Using a procedure similar to that described in Example 27a, the title compound was obtained (60%), after chromatography (eluant: hexane, then hexane/diethyl ether; 9/1) over silical gel and recrystallization from hexane, as white crystals, mp 91°–92° C.

Analysis for $C_{12}H_{13}ClF_3NO_2$ Calculated: C, 48.74; H, 4.43; N, 4.73 Found: C, 48.74; H, 4.53; N, 4.70 d. 2-(tert-Butoxycarbonyl)-6-chloro-4-trifluoromethylbenzoic acid.

To a cold (−100° C.) stirred solution of N-(tert-butoxycarbonyl)-3-chloro-5-trifluoromethylaniline 93.4 g, 11.5 mM) in dry tetrahydrofuran (30 mL) under a nitrogen atmosphere was added dropwise t-butyllithium (14.2 mL of 1.7M solution, 24.2 mM) in pentane. The temperature of the reaction mixture was maintained at −103° to −98° C. during the addition and for 3.25 hr after the addition was completed. Crushed Dry Ice was then added to the cold reaction mixture which, after being allowed to warm to −75° C., was poured into water. The resulting mixture was extracted with ethyl acetate and the combined extracts were dried ($MgSO_4$), filtered and concentrated to leave (3.2 g, 82%) the title compound as a solid white foam.

250-MHz $^1$H NMR (DMSO-$d_6$): 9.88 (s, 1H), 8.15 (s, 1H), 7.39 (s, 1H), 1.48 (s, 9H).

e. 2-Amino-6-chloro-4-trifluoromethylbenzoic acid.

A solution of 2-(tert-butoxycarbonyl)-6-chloro-4-trifluoromethylbenzoic acid (0.75 g, 2.2 mM) and boron trifluoride etherate (1.25 g, 8.8 mL) in anhydrous methanol (20 mL) under a nitrogen atmosphere was refluxed for 2 hr. The reaction mixture was allowed to cool and then concentrated. The residue was diluted with water and the resulting mixture extracted with ethyl acetate. The combined extracts were dried ($MgSO_4$), filtered and concentrated to obtain (0.53 g, 100%) the title compound as a tan solid; MS(CI): 240 (M+H).

250-MHz $^1$H NMR (DMSO-$d_6$): 7.01 (s, 1H), 6.90 (s, 1H).

f. 5-Chloro-7-trifluoromethyl-2H-3,1-benzoxazine-2,4(1H)-dione.

To a stirred solution of 2-amino-4-chloro-6-trifluoromethylbenzoic acid (0.53 g, 2.2 mM) in dry tetrahydrofuran (6 mL) under a nitrogen atmosphere was added bis(trichloromethyl)carbonate (0.218 g, 0.734 mM). The resulting solution was stirred at room temperature for 2 hr, poured into water and the resulting mixture extracted with ethyl acetate. The combined extracts were dried (MgSO4), filtered and concentrated to leave the title compound as a tan solid; MS(CI): 266 (M+H).

250-MHz $^1$H NMR (DMSO-$d_6$): 12.08 (s, 1H), 7.71 (s, 1H), 7.33 (s, 1H).

g. Methyl 2-amino-6-chloro-4-trifluoromethylbenzoate.

To a stirred solution of sodium hydroxide (0.012 g, 0.31 mM) in anhydrous methanol (1.5 mL) under a nitrogen atmosphere was added 5-chloro-7-trifluoromethyl-2H-3,1-benzoxazine-2,4(1H)-dione (0.60 g, 2.3 mM). The resulting mixture was warmed to 60° C. for 0.5 hr, allowed to cool to room temperature and poured into diethyl ether. The ether was washed with water, dried ($MgSO_4$), filtered and concentrated to leave (0.50 g, 88%) the title compound as a yellow oil; MS(CI): 254 (M+H).

250-MHz 1H NMR (DMSO-$d_6$): 6.99 (s, 1H), 6.89 (s, 1H), 6.19 (s, 2H, exchangeable), 3.84 (s, 3H).

h. Dimethyl 5-chloro-4-hydroxy-7-trifluoromethylquinoline-2,3-dicarboxylate.

Using a prodedure similar to that described in Example 11b except starting with methyl 2-amino-6-chloro-4-trifluoromethylbenzoate, the title compound was obtained (43.4%) as a tan solid after chromatography (eluant: methylene chloride/methanol; 98/2) over silica gel; MS(CI): 364 (M+H).

300-MHz $^1$H NMR (DMSO-$d_6$): 12.54 (, 1H, exchangeable), 8.33 (s, 1H), 7.72 (s, 1H), 3.97 (s, 3H), 3.79 (s, 3H).

EXAMPLE 29

2,3-Dihydro-7-fluoro-10-hydroxypyridazino[4,5-b]quinoline-1,4-dione

Using a procedure similar to that described in Example 6 except starting with dimethyl 4-hydroxy-7-fluoroquinoline-2,3-dicarboxylate, the title compound was obtained (93%) as a tan solid, mp >390° C. MS(CI): 248 (M+H).

Analysis for $C_{11}H_6FN_3O_3 \cdot 0.19 H_2O$ Calculated: C, 52.72; H, 2.57; N, 16.77 Found: C, 52.73; H, 2.75; N, 16.95

300-MHz $^1$H NMR (DMSO-$d_6$): 12.45 (s, 1H, exchangeable), 12.37 (s, 1H, exchangeable), 8.35 (dd, J=8.8, 6.2 Hz, 1H), 7.86 (dd, J=10.2, 2.4 Hz, 1H), 7.45 (dt, J=8.8, 8.8, 2.4, 1H)

The starting dimethyl 4-hydroxy-7-fluoroquinoline-2,3-dicarboxylate was prepared as follows:

a. Methyl 2-amino-4-fluorobenzoate.

A stirred solution of 2-amino-4-fluorobenzoic acid (4.86 g, 31.3 mM) in anhydrous methanol (100 mL) was saturated with anhydrous hydrogen chloride and then refluxed for 4 days. During the reflux period, the reaction mixture was periodically resaturated with hydrogen chloride. After the reflux period, the reaction mixture was cooled and concentrated to leave a whtie solid. This material was dissolved in water and the resulting solution neutralized with aqueous sodium bicarbonate and extracted with diethyl ether. The combined extracts were dried ($MgSO_4$), filtered and concentrated to leave (4.08 g, 80.6%) of the title compound as an off white solid, mp 66°–67° C.; MS(CI): 170 (M+H).

Analysis for $C_8H_8FNO_2$ Calculated: C, 56.80; H, 4.77; N, 8.28 Found: C, 56.88; H, 4.82; N, 8.24 b. Dimethyl 4-hydroxy-7-fluoroquinoline-2,3-dicarboxylate.

Using a procedure similar to that described in Example 3c except starting with methyl 2-amino-4-fluorobenzoate, the title compound was obtained (81%) as a light brown solid, mp 227.5°–228.5° C.; MS(CI): 280 (M+H).

Analysis for $C_{13}H_{10}FNO_5 \cdot 1.1 \, H_2O$ Calculated: C, 52.22; H, 4.08; N, 4.48 Found: C, 52.21; H, 4.11; N, 4.68

EXAMPLE 30

2,3-Dihydro-10-hydroxy-8-nitropyridazino[4,5-b]quinoline-1,4-dione

Using a procedure similar to that described in Example 6 except starting with diethyl 4-hydroxy-6-nitroquinoline-2,3-dicarboxylate, the title compound was obtained (89%) as pale yellow crystals, mp >400° C.; MS(CI): 275 (M+H).

Analysis for $C_{11}H_6N_4O_5 \cdot 0.16 \, H_2O$ Calculated: C, 47.68; H, 2.30; N, 20.22 Found: C, 47.69; H, 2.39, N, 20.18 250-MHz $^1H$ NMR (DMSO-$d_6$): 13.53 (s, 1H, exchangeable), 12.56 (s, 1H, exchangeable), 11.67 (s, 1H, exchangeable), 8.95 (s, 1H), 8.66 (d, J=4.4 Hz, 1H), 8.28 (d, J=4.4 Hz, 1H).

The starting diethyl 4-hydroxy-6-nitroquinoline-2,3-dicarboxylate was prepared as follows:

a. Diethyl 4-hydroxy-6-nitroquinoline-2,3-dicarboxylate.

Using a procedure similar to that described in Example 15d except starting with 6-nitro-2H-3,1-benzoxazine-2,4(1H)-dione, the title compound was obtained (43%) as a yellow crystalline solid. Recrystallization of a portion of this material from ethanol provided an analytical sample of the title compound as pale yellow crystals, mp 264°–264.5° C.; MS(CI): 335 (M+H).

Analysis for $C_{15}H_{14}N_2O_7$ Calculated: C, 53.89; H, 4.22; N, 8.38 Found: C, 53.99; H, 4.17; N, 8.40

EXAMPLE 31

8-Amino-2,3-dihydro-10-hydroxypyridazino[4,5-b]quinoline-1,4-dione

Using a procedure similar to that described in Example 6 except starting with diethyl 6-amino-4-hydroxyquinoline-2,3-dicarboxylate, the title compound was obtained (100%) as orange crystals, mp >400° C.; MS(CI): 245 (M+H).

Analysis for $C_{11}H_8N_4O_3 \cdot 0.69 \, H_2O$ Calculated: C, 51.48; H, 3.68; N, 21.65 Found: C, 51.47; H, 3.47; N, 21.65 300-MHz $^1H$ NMR (DMSO-$d_6$): (4:6 ratio of two tautomers) 13.12 (s, 2H, exchangeable), 12.16 (s, 1H, exchangeable), 7.91 (d, J=8.8 Hz, 1H), 7.58 (d, J=8.8 Hz, 1H), 7.28 (m, 3H), 7.05 (dd, J=8.8, 2.4 Hz, 1H), 5.86 (br s, 2H, exchangeable), 4.81 (s, 2H, exchangeable).

The starting diethyl 6-amino-4-hydroxyquinoline-2,3-dicarboxylate was prepared as follows:
a. Diethyl 6-amino-4-hydroxyquinoline-2,3-dicarboxylate.

A stirred mixture of diethyl 4-hydroxy-6-nitroquinoline-2,3-dicarboxylate (4.4 g, 13 mM), powdered iron (6.6 g, 118 mM) and glacial acetic acid (18.5 g, 307 mM) in ethanol (80 mL) was refluxed for 20 hr under a nitrogen atmosphere. The reaction mixture was cooled and filtered and the filtrate was concentrated. The dark residue was chromatographed (eluant: methylene chloride/methanol; 98/2) over silical gel to provide (3.01 g, 75.3%) the title compound as light orange crystals, mp 219°–221° C.; MS(CI): 305 (M+H).

Analysis for $C_{15}H_{16}N_2O_5 \cdot 0.3 \, H_2O$ Calculated: C, 58.18; H, 5.40; N, 9.04 Found: C, 58.48; H, 5.41; N, 8.54 250-MHz $^1H$ NMR (DMSO-$d_6$): 12.11 (br s, 1H, exchangeable), 7.67 (d, J=8.8 Hz, 1H), 7.16 (d, J=2.1 Hz, 1H), 7.09 (dd, J=8.8, 2.1 Hz, 1H), 5.65 (br s, 2H, exchangeable), 4.38 (q, J=7.1 Hz, 2H), 4.20 (q, J=7.1 Hz, 2H), 1.29 (m, 6H).

EXAMPLE 32

9-Bromo-2,3-dihydro-7-ethyl-10-hydroxypyridazino[4,5-b]quinoline-1,4-dione

A stirred mixture of 2,3-bishydrazinocarbonyl-5-bromo-7-ethyl-4-hydroxyquinoline (0.40 g, 1.1mM) in glacial acetic acid (12 mL) was heated at 81° C. for 1.5 hr. After cooling to room temperature, the reaction mixture was filtered and the collected solids washed with acetic acid and air dried to provide the title compound (0.25 g, 70%) as a light brown solid, mp >400° C.; MS(CI): 336 (M+H).

Analysis for $C_{13}H_{10}BrN_3O_3 \cdot 0.13 \, CH_3CO_2H$ Calculated: C, 46.31; H, 3.08; N, 12.21 Found: C, 46.50; H, 3.32; N, 12.19 300-MHz $^1H$ NMR (DMSO-$d_6$): 13.06 (s, 1H, exchangeable), 12.64 (s, 1H, exchangeable), 12.40 (s, 1H, exchangeable), 7.99 (s, 1H), 7.66 (s, 1H), 2.64 (q, J=7.5 Hz, 2H), 1.24 (t, J=7.5 Hz, 3H).

The starting 2,3-bishydrazinocarbonyl-5-bromo-7-ethyl-4-hydroxyquinoline was prepared as follows:
a. 5-Bromo-7-ethyl-2H-3,1-benzoxazine-2,4(1H)-dione.

Using a procedure similar to that described in Example 26d except starting with 4-bromo-6-ethyl-1H-indole-2,3-dione (isolated as a coproduct as described in Example 26c), the title compound was obtained (53%) as a tan solid. Recrystallization of a portion of this material from ethyl acetate/hexane provided an analytical sample of the title compound as tan crystals, mp 236°–237° C.

Analysis for $C_{10}H_8BrNO_3$ Calculated: C, 44.49; H, 2.99; N, 5.19 Found: C, 44.40; H, 2.95; N, 5.12
b. Methyl 2-amino-6-bromo-4-ethylbenzoate.

Using a procedure similar to that described in Example 14d except starting with 5-bromo-7-ethyl-2H-3,1-benzoxazine-2,4(1H)-dione, the title compound was obtained (73%), after chromatography (eluant: hexane/diethyl ether; 9/1) over silica gel, as a light yellow oil; MS(CI): 253 (M+H).

250-MHz $^1H$ NMR (DMSO-$d_6$): 6.65 (s, 1H), 6.55 (s, 1H), 5.67 (s, exchangeable, 2H), 3.80 (s, 3H), 2.43 (q, J=7.6 Hz, 2H), 1.12 (t, J=7.6 Hz, 3H).
c. Dimethyl 5-bromo-7-ethyl-4-hydroxyquinoline-2,3-dicarboxylate.

Using a procedure similar to that described in Example 3c except starting with methyl 2-amino-6-bromo-4-ethylbenzoate, the title compound was obtained (75%) as a tan solid. Recrystallization of a portion of this material from toluene provided an analytical sample of the title compound as tan crystals, mp 207°–208° C.; MS(CI): 368 (M+H).

Analysis for $C_{15}H_{14}BrNO_5$ Calculated: C, 48.93; H, 3.83; N, 3.81 Found: C, 48.85; H, 3.82; N, 3.73
d. 2,3-Bishydrazinocarbonyl-5-bromo-7-ethyl-4-hydroxyquinoline.

To a mixture of dimethyl 5-bromo-7-ethyl-4-hydroxyquinoline-2,3-dicarboxylate (1.0 g, 2.7 mM,) in ethanol (25 mL) was added hydrazine hydrate (0.68 g, 14 mM). The resulting mixture was concentrated at 30° C. using a rotary evaporator and the residue was diluted with another portion of ethanol (25 mL) and similarly concentrated at 30° C. The residue was suspended in ethanol and filtered to separate the title compound (0.82 g, 82%) as a light yellow solid. Recrystallization of a portion of this material from dimethylsulfoxide/ethanol provided an analytical sample of the title compound as a light yellow crystalline solid, mp 335°–340° C. (dec).

Analysis for $C_{13}H_{14}BrN_5O_3 \cdot 0.35 \, H_2O$ Calculated: C, 41.70; H, 3.95; N, 18.70 Found: C, 41.99; H, 3.84; N, 18.31

EXAMPLE 33

2,3-Dihydropyridazino[4,5-b]quinoline-1,4-dione

Using a procedure similar to that described in Example 6 except starting with dimethyl quinoline-2,3-dicarboxylate, the title compound was obtained (75%) as a yellow solid, mp 345°–349° C. MS(CI): 214 (M+H).

Analysis for $C_{11}H_7N_3O_2 \cdot 0.35\ H_2O$ Calculated: C, 60.19; H, 3.54; N, 19.14 Found: C, 60.24; H, 3.47; N, 19.16 250-MHz $^1H$ NMR (DMSO-$d_6$): 11.53 (br s, 2H, exchangeable), 9.29 (s, 1H), 8.37 (d, J=7.8, 1H), 8.28 (d, J=9.0, 1H), 8.04 (t, J=7.0, 1H), 7.84 (t, J=7.0, 1H).

The starting dimethyl quinoline-2,3-dicarboxylate was prepared as follows:

a. Dimethyl 4-chloroquinoline-2,3-dicarboxylate.

Using a procedure similar to that described in Example 12a except starting with dimethyl 4-hydroxyquinoline-2,3-dicarboxylate, the title compound was obtained (100%) as a pale yellow solid; MS(CI): 280 (M+H).

250-MHz $^1H$ NMR (CDCl$_3$): 8.33 (dd, J=8.3, 1.5 HZ, 1H), 7.88 (m, 2H), 4.08 (s, 3H), 4.06 (s, 3H).

b. Dimethyl quinoline-2,3-dicarboxylate.

Using a procedure similar to that described in Example 12b except starting with dimethyl 4-chloroquinoline-2,3-dicarboxylate, the title compound was obtained (57%) as a light yellow solid; MS(CI): 246 (M+H).

250-MHz $^1H$ NMR (CDCl$_3$): 8.78 (s, 1H), 8.21 (d, J=8.8 Hz, 1H), 7.91 (m, 2H), 7.70 (t, J=7.9 Hz, 1H), 4.06 (s, 3H), 3.99 (s, 3H).

EXAMPLE 34

2,3-Dihydro-10-hydroxy-9-trifluoromethylpyridazino[4,5-b]quinoline-1,4-dione

Using a procedure similar to that described in Example 8 except starting with dimethyl 4-hydroxy-5-trifluoromethyl-2,3-dicarboxylate, the title compound was obtained (60%) as a light tan cyrstalline solid, mp >335° C.; MS(CI): 298 (M+H).

Analysis for $C_{12}H_6F_3N_3O_3 \cdot 0.13\ H_2O$ Calculated: C, 48.12; H, 2.11; N, 14.03 Found: C, 48.13; H, 2.16; N, 14.07 300-MHz $^1H$ NMR (DMSO-$d_6$): 13.42 (s, 1H, exchangeable), 12.51 (s, 1H, exchangeable), 12.48 (s, 1H, exchangeable), 8.48 (d, J=8.0 Hz, 1H), 8.03 (m, 2H).

The starting dimethyl 4-hydroxy-5-trifluoromethylquinoline-2,3-dicarboxylate was prepared as follows:

a. N-(3-Trifluoromethylphenyl)-2-(hydroxyimino) acetamide.

Using a procedure similar to that described in Example 8a except starting with 3-trifluoromethylaniline, the title compound was obtained (90%) as light tan solids. Recrystallization of a portion of this material from methylene chloride/chloroform provided an analytical sample of the title compound as white crystals, mp 139.5°–140.5° C.; MS(CI): 233 (M+H).

Analysis for $C_9H_7F_3N_2O_2$ Calculated: C, 46.56; H, 3.04; N, 12.07 Found: C, 46.75; H, 2.97; N, 12.15 b. 4-Trifluoromethyl-1H-indole-2,3-dione.

Using a procedure similar to that described in Example 8b except starting with N-(3-trifluoromethylphenyl)-2-(hydroxyimino)acetamide, the title compound, along with the isomeric 6-trifluoromethyl-1H-indole-2,3-dione, was obtained (65%) as a mixture. Stirring this mixture with anhydrous diethyl ether and filtering the undissolved solids provided (29%) the title compound as a yellow crystalline solid; MS(CI): 216 (M+H).

250-MHz $^1H$ NMR (DMSO-$d_6$): 11.30 (s, 1H, exchangeable), 7.74 (t, J=7.8 Hz, 1H), 7.36 (d, J=7.7 Hz, 1H), 7.21 (d, J=8.0 Hz, 1H).

c. 5-Trifluoromethyl-2H-3,1-benzoxazine-2,4(1H)-dione.

Using a procedure similar to that described in Example 8c except starting with 4-trifluoromethyl-1H-indole-2,3-dione, the title compound was obtained (64%) as a yellow crystalline solid, mp 232°–233° C.; MS(CI): 232 (M+H).

300-MHz $^1H$ NMR (DMSO-$d_6$): 7.88 (t, J=8.0 Hz, 1H), 7.65 (d, J=7.6 Hz, 1H), 7.45 (d, J=8.3 Hz, 1H).

d. Methyl 2-amino-6-trifluoromethylbenzoate.

Using a procedure similar to that described in Example 8d except starting with 5-trifluoromethyl-2H-3,1-benzoxazine-2,4(1H)-dione, the title compound was obtained (40%), after chromatography (eluant: diethyl ether/hexane; 3/2) over silica gel, as a light tan oil; MS(CI): 220 (M+H).

250-MHz $^1H$ NMR (DMSO-$d_6$): 7.32 (t, J=8.1 Hz, 1H), 7.01 (d, J=8.3 Hz, 1H), 6.90 (d, J=7.6 Hz, 1H), 5.81 (br s, 2H, exchangeable), 3.83 (s, 3H).

e. Dimethyl 4-hydroxy-5-trifluoromethylquinoline-2,3-dicarboxylate.

Using a procedure similar to that described in Example 8e except starting with methyl 2-amino-6-trifluoromethylbenzoate, the title compound was obtained (65%) as a brown solid. Recrystallization of a portion of this material from toluene/diethyl ether provided an analytical sample of the title compound as tan crystals, mp 180.5°–181.5° C.; MS (CI): 330 (M+H).

Analysis for $C_{14}H_{10}F_3NO_5$ Calculated: C, 51.07; H, 3.06; N, 4.25 Found: C, 51.06; H, 3.09; N, 4.17

EXAMPLE 35

2,3-Dihydro-10-hydroxy-7-trifluoromethylpyridazino[4,5-b]quinoline-1,4-dione

Using a procedure similar to that described in Example 8 except starting with dimethyl 4-hydroxy-7-trifluoromethylquinoline-2,3-dicarboxylate, the title compound was obtained (93%) as a yellow-brown crystalline solid, mp >400° C.; MS(CI): 298 (M+H).

Analysis for $C_{12}H_6F_3N_3O_3 \cdot 0.07\ H_2O$ Calculated: C, 48.29; H, 2.07; N, 14.08 Found: C, 48.10; H, 1.96; N, 14.41 300-MHz $^1H$ NMR (DMSO-$d_6$): 12.3 (s, 1H, exchangeable), 12.50 (s, 1H, exchangeable), 12.13 (s, 1H, exchangeable), 8.52 (s, 1H), 8.45 (d, J=8.5 Hz, 1H), 7.83 (d, J=8.5 Hz, 1H)

The starting dimethyl 4-hydroxy-7-trifluoromethylquinoline-2,3-dicarboxylate was prepared as follows:

a. 2-Amino-4-trifluoromethylbenzoic acid.

A mixture of 2-nitro-4-trifluorobenzoic acid (3.78 g, 16.1 mM) and 10% palladium on carbon catalyst (2.05 g) in ethanol (150 mL) was hydrogenated on a Parr apparatus for 1.5 hr at room temperature. The mixture was filtered to separate the catalyst and the filtrate was concentrated to provide the title compound (3.22 g, 98%) as a light grey crystalline solid, mp 170.5°–172.5° C.; MS(CI): 206 (M+H).

Analysis for $C_8H_6F_3NO_2$ Calculated: C, 46.84; H, 2.95; N, 6.83 Found: C, 46.90; H, 3.11; N, 6.80 b. Methyl 2-amino-4-trifluoromethylbenzoate.

Using a procedure similar to that described in Example 9c except starting with 2-amino-4-trifluoromethylbenzoic acid, the title compound was obtained (86%), after chromatography (eluant: diethyl ether/hexane: 3/7) over silica gel, as a tan crystals, mp 62.5°–63° C. MS(CI): 220 (M+H).

Analysis for $C_9H_8F_3NO_2$ Calculated: C, 49.32; H, 3.68; N, 6.39 Found: C, 49.23; H, 3.75; N, 6.34 250-MHz $^1H$ NMR (DMSO-$d_6$): 7.88 (d, J=8.4 Hz, 1H), 7.18 (s, 1H), 7.00 (br s, 2H), 6.79 (d, J=8.4 Hz, 1H), 3.84 (s, 3H).

c. Dimethyl 4-hydroxy-7-trifluoromethylquinoline-2,3-dicarboxylate.

Using a procedure similar to that described in Example 3c except starting with methyl 2-amino-4-trifluoromethylbenzoate and employing a five day reaction time to form the intermediate enamine adduct, the title compound was obtained (67%) as a tan crystalline solid, mp 210°–210.5° C.; MS(CI): 330 (M+H).

Analysis for $C_{14}H_{10}F_3NO_5$ Calculated: C, 51.07; H, 3.06; N, 4.25 Found: C, 51.16; H, 3.23; N, 4.17

EXAMPLE 36

9-Bromo-2,3-dihydro-10-hydroxypyridazino[4,5-b]quinoline-1,4-dione

Using a procedure similar to that described in Example 32 except starting with 2,3-bishydrazinocarbonyl-5-bromo-4-hydroxyquinoline, the title compound was obtained (94%) as an orange-brown solid, mp >390° C.; MS(CI): 308 (M+H).

Analysis for $C_{11}H_9BrN_3O_3$ Calculated: C, 42.88; H, 1.96; N, 13.64 Found: C, 42.81; H, 2.05; N, 13.96 250-MHz $^1$H NMR (DMSO-$d_6$): 12.55 (s, 1H, exchangeable), 12.43 (s, 1H, exchangeable), 8.14 (d, J=8.0 Hz, 1H), 7.74 (m, 2H).

The starting 2,3-bishydrazinocarbonyl-5-bromo-4-hydroxyquinoline was prepared as follows:

a. 5-Bromo-2H-3,1-benzoxazine-2,4(1H)-dione.

Using a procedure described in Example 4a except starting with 4-bromo-1H-indole-2,3-dione (as prepared in Example 15b), the title compound was obtained (82.3%) as a yellow crystalline solid, mp 280°–281° C.; MS(CI): 242 (M+H).

Analysis for $C_8H_4BrNO_3 \cdot 0.76\,H_2O$ Calculated: C, 37.57; H, 2.17; N, 5.48 Found: C, 37.32; H, 1.77; N, 5.55 b. Methyl 2-amino-6-bromobenzoate.

Using a procedure similar to that described in Example 4b except starting with 5-bromo-2H-3,1-benzoxazine-2,4(1H)-dione, the title compound was obtained (86.7%) as a yellow oil; MS(CI): 230 (M+H).

300-MHz $^1$H NMR (DMSO-$d_6$): 7.02 (t, J=8.0 Hz, 1H), 6.74 (m, 2H), 5.67 (s, 2H), 3.82 (s, 3H).

c. Dimethyl 5-bromo-4-hydroxyquinoline-2,3-dicarboxylate.

Using a procedure similar to that described in Example 4c except starting with methyl 2-amino-6-bromobenzoate, the title compound was obtained (100%) as a tan crystalline solid, mp 124.5°–125.5° C.; MS(CI): 340 (M+H).

Analysis for $C_{13}H_{10}BrNO_5 \cdot 0.8\,H_2O$ Calculated: C, 44.04; H, 3.30; N, 3.95 Found; C, 44.06; H, 3.47; N, 3.76 d. 2,3-bishydrazinocarbonyl-5-bromo-4-hydroxyquinoline.

Using a procedure similar to that described in Example 32d except starting with dimethyl 5-bromo-4-hydroxyquinoline-2,3-dicarboxylate, the title compound was obtained (87%) as a fine yellow solid.

EXAMPLE 37

7-Chloro-2,3-dihydro-10-hydroxy-9-methylpyridazino[4,5-b]quinoline-1,4-dione Using a procedure similar to that described in Example 8 except starting with dimethyl 7-chloro-4-hydroxy-5-methylquinoline-2,3-dicarboxylate, the title compound was obtained (71%) as a light orange crystalline solid, mp >398° C.; MS(CI): 278 (M+H).

Analysis for $C_{12}H_8ClN_3O_3 \cdot 0.07\,H_2O$ Calculated: C, 51.67; H, 2.94; N, 15.06 Found: C, 51.67; H, 2.70; N 15.30 400-MHz $^1$H NMR (DMSO-$d_6$): 12.68 (s, 1H, exchangeable), 12.60 (s, 1H, excahngeable), 12.34 (s, 1H, exchangeable), 7.97 (s, 1H), 7.27 (s, 1H), 2.60 (s, 1H).

The starting dimethyl 7-chloro-4-hydroxy-5-methylquinoline-2,3-dicarboxylate was prepared as follows:

a. 2-Chloro-4-methyl-6-nitroaniline.

To a stirred solution of 4-methyl-2-nitroaniline (19.69 g, 129.4 mM) in chloroform (200 mL) under a nitrogen atmosphere was added dropwise a solution of chlorine (10.15 g, 285.9 mM) in chloroform (100 mL) while maintaining the reaction mixture temperature below 30° C. The reaction mixture was stirred for 3 days and then washed with aqueous sodium bicarbonate. The organic phase was then concentrated and the residue chromatographed (eluant: hexane/diethyl ether; 9/1) over silica gel to provide (6.03 g, 25%) the title compound as an orange crystalline solid, mp 68.5°–69.5° C.; MS(CI): 187 (M+H).

Analysis for $C_7H_7ClN_2O_2 \cdot 0.12\,H_2O$ Calculated: C, 44.54; H, 3.86; N, 14.84 Found: C, 44.52; H, 3.78; N, 14.87 300-MHz $^1$H NMR (DMSO-$d_6$): 7.84 (d, J=1.7 Hz), 7.59 (d, J=1.7 Hz, 1H), 7.11 (s, 2H), 2.22 (s, 3H).

b. 3-Chloro-5-nitrotoluene.

To a stirred mixture of 2-chloro-4-methyl-6-nitroaniline (7.39 g, 39.7 mM) and concentrated sulfuric acid (6.2 mL) in absolute ethanol (50 mL) at 0°–5° C. was slowly added a solution of sodium nitrite (6.85 g, 99.3 mM) in water (6 mL). The temperature of the reaction mixture was not allowed to exceed 5° C. during the addition. After the addition was completed, the reaction mixture was stirred at room temperature for 0.5 hr and then at reflux until the evolution of gas from the reaction mixture ceased. The reaction mixture was allowed to cool and was concentrated. The residue was slurried with ether and then filtered to remove the solids. The filtrate was concentrated and the residue chromatographed (eluant: diethyl ether/hexane; 1/9) to provide (6.25 g, 92%) the title compound as a yellow crystalline solid, mp 60.5°–61° C.; MS(CI): 172 (M+H).

Analysis for $C_7H_6ClNO_2$ Calculated: C, 49.00; H, 3.52; N, 8.16 Found; C, 49.05; H, 3.53; N, 8.16 c. 3-Chloro-5-methylaniline.

Using a procedure similar to that describe in Example 24a except starting with 3-chloro-5-nitrotoluene, the title compound was obtained (85%)as a yellow solid; MS(CI): 142 (M+H). 300-MHz $^1$H NMR (DMSO-$d_6$): 6.56 (s, 1H), 6.48 (s, 1H), 6.36 (s, 1H), 3.65 (br s, 2H), 2.22 (s, 3H).

d. N-(3-Chloro-5-methylphenyl)-2-(hydroxyimino)acetamide.

Using a procedure similar to that described in Example 8a except starting with 3-chloro-5-methylaniline, the title compound was obtained (95%) as a light tan crystalline solid, mp 206°–207° C.; MS(CI): 213 (M+H).

250-MHz $^1$H NMR (DMSO-$d_6$): 12.26 (s, 1H), 10.28 (s, 1H), 7.67 (s, 1H), 7.64 (s, 1H), 7.43 (, 1H), 7.00 (s, 1H), 2.29 (s, 3H).

e. 6-Chloro-4-methyl-1H-indole-2,3-dione and 4-chloro-6-methyl-1H-indole-2,3-dione.

Using a procedure similar to that described in Example 8b except starting with N-(3-chloro-5-methylphenyl)-2-(hydroxyimino)acetamide, a mixture of the title compounds was obtained (100%) as tan solids; MS(CI): 196 (M+H).

f. 7-Chloro-5-methyl-2H-3,1-benzoxazine-2,4(1H)-dione and 5-chloro-7-methyl-2H-3,1-benzoxazine-2,4(1H)-dione.

Using a procedure similar to that described in Example 26d except starting with the above mixture of 6-chloro-4-methyl-1H-indole-2,3-dione and 4-chloro-6-methyl-1H-indole-2,3-dione, a mixture of the title compounds was obtained (75%) as tan solids; MS(CI): 212 (M+H).

250-MHz $^1$H NMR (DMSO-$d_6$): 11.78 (br s, 1H), 7.17 (s, 2H), 6.98 (s, 1H), 6.85 (s, 1H), 2.58 (s, 3H), 2.32 (s, 3H); This material is an approximate 1/1 mixture of isomers.

g. Methyl 2-amino-4-chloro-6-methylbenzoate and methyl 2-amino-6-chloro-4-methylbenzoate.

Using a procedure similar to that described in Example 8d except starting with the above mixture of 7-chloro-5-methyl-2H-3,1-benzoxazine-2,4(1H)-dione and 5-chloro-7-methyl-2H-3,1-benzoxazine-2,4(1H)-dione, a mixture (1:1) of the title compounds was obtained (75%) as tan solids. The isomeric compounds were separated by chromatography (eluant: diethyl ether/hexane; 1/9) over silica gel.

Methyl 2-amino-4-chloro-6-methylbenzoate, the isomer which eluted first was isolated (39%) as a light tan solid, mp 54°–55° C. MS (CI): 200 (M+H).

400-MHz $^1$H NMR (DMSO-$d_6$): 6.66 (s, 1H), 6.44 (s, 1H), 6.11 (s, 2H), 3.79 (s, 3H), 2.27 (s, 3H).

Methyl 2-amino-6-chloro-4-methylbenzoate, the isomer which eluted last, was isolated (36%) as a tan solid; MS(CI): 200 (M+H).

400-MHz $^1$H NMR (DMSO-$d_6$): 6.49 (s, 1H), 6.46 (s, 1H), 5.78 (s, 2H), 3.80 (s, 3H), 2.15 (s, 3H).

h. Dimethyl 7-chloro-4-hydroxy-5-methylquinoline-2,3-dicarboxylate.

Using a procedure similar to that described in Example 8e except starting with methyl 2-amino-4-chloro-6-methylbenzoate, the title compound was obtained (80%), after chromatography (eluant: diethyl ether/hexane; 4/1) over silica gel and recrystallization from diethyl ether, as white crystals, mp 117°–119° C.; MS(CI): 310 (M+H).

Analysis for $C_{14}H_{12}ClNO_5 \cdot 0.79\ H_2O$ Calculated: C, 51.91; H, 4.22; N, 4.32 Found: C, 51.91; H, 4.20; N, 4.24

EXAMPLE 38

9-Chloro-2,3-dihydro-10-hydroxy-7-methylpyridazino[4,5-b]quinoline-1,4-dione

Using a procedure similar to that described in Example 8 except starting with dimethyl 5-chloro-4-hydroxy-7-methylquinoline-2,3-dicarboxylate, the title compound was obtained (92%) as a light orange crystalline solid, mp >400° C.; MS(CI): 278 (M+H).

Analysis for $C_{12}H_8ClN_3O_3 \cdot 0.6\ CH_3CO_2HE \cdot 0.06\ H_2O$ Calculated: C, 50.37; H, 3.36; N, 13.35 Found: C, 50.36; H, 3.25; N, 13.25 300-MHz $^1$H NMR (DMSO-$d_6$): 12.67 (s, 1H, exchangeable), 12.41 (s, 1H, exchangeable), 7.87 (s, 1H), 7.40 (s, 1H), 2.44 (s, 3H).

The starting dimethyl 5-chloro-4-hydroxy-7-methylquinoline-2,3-dicarboxylate was prepared as follows:
a. Dimethyl 5-chloro-4-hydroxy-7-methylquinoline-2,3-dicarboxylate.

Using a procedure similar to that described in Example 8e except starting with methyl 2-amino-6-chloro-4-methylbenzoate (as prepared in Example 37 g, the title compound was obtained (85%) as a light grey crystalline solid, mp 197°–199° C. MS(CI): 310 (M+H)

Analysis for $C_{14}H_{12}ClNO_5 \cdot 0.48\ H_2O$ Calculated: C, 52.82; H, 4.10; N, 4.39 Found: C, 52.82; H, 3.90; N, 4.27

EXAMPLE 39

7-Chloro-2,3-dihydro-10-thiohydroxypyridazino[4,5-b]quinoline-1,4dione

To a stirred mixture of dimethyl 7-chloro-4-thiohydroxyquinoline-2,3-dicarboxylate (0.700 g, 2.25 mM) in ethanol (20 mL) was added hydrazine hydrate (3.37 g, 67.4 mM). After stirring at room temperature for 1 hr, the reaction mixture was concentrated while not allowing the temperature to exceed 30° C. The residue was diluted with additional ethanol and again concentrated at a temperature not exceeding 30° C. The residue was diluted with glacial acetic acid and the resulting mixture heated at 90°–100° C. for 1 hr. After cooling, the reaction mixture was filtered and the collected solids washed with diethyl ether and air dried to provide a red solid. Recrystallization of this material from dimethylsulfoxide provided (0.41 g, 65%) the title compound as orange crystals, mp >390° C.; MS(CI): 280 (M+H).

Analysis for $C_{11}H_6ClN_3O_2 \cdot 0.7\ (CH_3)_2SO$ Calculated: C, 44.54; H, 3.07; N, 12.57 Found: C, 44.47; H, 2.97; N, 12.66 250-MHz $^1$H NMR (DMSO-$d_6$): 13.54 (s, 1H), 12.52 (s, 1H), 9.67 (s, 1H), 8.77 (d, J=9.1 Hz, 1H), 8.29 (d, J=2.0 Hz, 1H), 7.69 (dd, J=9.1, 2.0 Hz, 1H).

The starting dimethyl 7-chloro-4-thiohydroxyquinoline-2,3-dicarboxylate was obtained as follows:
a. Dimethyl 7-chloro-4-thiohydroxyquinoline-2,3-dicarboxylate.

A mixture of dimethyl 7-chloro-4-hydroxyquinoline-2,3-dicarboxylate (1.5 g, 5.1 mM) and 2,4-bis(4-methoxyphenyl)-1,3-dithia-2,4-diphosphetane-2,4-disulfide (Lawesson's Reagent, 1.23 g, 3.04 mM) in toluene (31 mL) was heated under a nitrogen atmosphere for 1 hr. The reaction mixture was cooled and concentrated and the residue was chromatographed (eluant: hexane/diethyl ether; 1/1) over silica gel to provide (1.18 g, 75%) the title compound as a yellow-brown solid. Recrystallization of a portion of this material from toluene provided the title compound as amber crystals, mp 193°–194° C.: MS(CI): 312.

Analysis for $C_{13}H_{10}ClNO_4S$ Calculated: C, 50.09; H, 3.23; N, 4.49 Found: C, 49.89; H, 3.23; N, 4.36

EXAMPLE 40

2,3-Dihydro-10-hydroxypyridazino[4,5-b]naphthyridine-1,4-dione

Using a procedure similar to that described in Example 6 except starting with diethyl 4-hydroxynaphthyridine-2,3-dicarboxylate, the title compound was obtained (72.4%), after recrystallization from dimethylsulfoxide, as a yellow crystalline solid, mp >400° C.; MS(CI): 231 (M+H).

Analysis for $C_{10}H_6N_4O_3 \cdot 0.10\ H_2O$ Calculated: C, 51.78; H, 2.69; N, 24.15 Found: C, 51.78; H, 2.63; N, 24.23 250-MHz $^1$H NMR (DMSO-$d_6$): 13.52 (s, 1H, exchangeable), 12.44 (s, 1H, exchangeable), 12.19 (s, 1H, exchangeable), 9.01 (m, 1H), 8.65 (d, J=8.1 Hz, 1H), 7.62 (m, 1H).

The starting diethyl 4-hydroxynaphthyridine-2,3-dicarboxylate was prepared as follows:
a. 2-Aminocarbonylnicotinic acid.

Anhydrous ammonia was bubbled into a stirred solution of 2,3-pyridinedicarboxylic anhydride (37.0 g, 248 mM) in 2-butanone (500 mL) for 5 min whereupon a white precipitate formed. After stirring a room temperature for 1 hr, the mixture was filtered and the collected solids were washed with water and air dried to provide (23.53 g, 57.1%) the title compound as a white crystalline solid, mp 176.5°–177.5° C.; MS(CI): 167 (M+H).

Analysis for $C_7H_6N_2O_3$ Calculated: C, 50.61; H, 3.64; N, 16.86 Found: C, 50.51; H, 3.75; N, 16.74
b. 8-Azaisatoic anhydride.

Lead tetraacetate (5.5 g, 12.4 mM) was added in one portion to a stirred mixture of 2-carboxyamidonicotinic acid (2.0 g, 12 mM) in dimethylformamide (20 mL) under a nitrogen atmosphere. After heating (65° C.) for 1 hr, the reaction mixture was poured into ice water (20 mL) whereupon a precipitate formed. The resulting mixture was filtered to collect (1.68 g, 85.1%) the title compound as a light tan crystalline solid, mp 214.5°–215.5° C.: MS(CI): 165 (M+H).

Analysis for $C_7H_4N_2O_3$ Calculated: C, 51.23; H, 2.46; N, 17.07 Found: C, 51.05; H, 2.43; N, 17.21 c. Diethyl 4-hydroxynaphthyridine-2,3-dicarboxylate.

Using a procedure similar to that described in Example 15d except starting with 8-azaisatoic anhydride, the title compound was obtained (22.6%) as a pale yellow oil; MS(CI): 291 (M+H).

300-MHz $^1$H NMR (DMSO-$d_6$): 13.01 (s, 1H, exchangeable), 8.88 (m, 1H), 8.51 (dd, J=8.0, 1.7 Hz, 1H), 7.54 (m, 1H), 4.38 (q, J=7.1 Hz, 2H), 4.23 (q, J=7.1 Hz, 2H), 1.34 (t, J=7.1 Hz, 3H), 1.26 (t, J=7.1 Hz, 3H).

EXAMPLE 41

1-(Benzoyloxy)-7-chloro-10-hydroxypyridazino[4,5-b]quinolin-4(3H)-one

Using a procedure similar to that desribed in Example 19 except starting with benzoyl chloride, the title compound was obtained (0.57 g, 32%) as a white powder, mp 348°–353° C.; MS(CI): 368 (M+H).

Analysis for $C_{18}H_{10}ClN_3O_4 \cdot 0.25$ $H_2O$: Calculated: C, 58.1; H, 2.84; N, 11.29 Found: C, 58.3; H, 2.96; N, 11.28 300-MHz $^1$H-NMR (DMSO-$d_6$): 13.23 (s, 1H, exchangeable), 12.83 (br s, 1H, exchangeable), 8.15–8.12 (m, 3H), 8.08 (d, J=8.7 Hz, 1H), 7.82–7.77 (m, 1H), 7.67–7.62 (m, 2H), 7.46 (dd, J=2.0, 8.7 Hz, 1H).

EXAMPLE 42

1-(Isovaleryloxy)-7-chloro-10-hydroxypyridazino[4,5-b]quinolin-4(3H)-one

Using a procedure similar to that described in Example 19 except starting with isovaleryl chloride, the title compound was obtained (28%) as a yellow powder, mp >400° C.; MS(CI): 348 (M+H).

Analysis for $C_{16}H_{14}ClN_3O_4$: Calculated: C, 55.3; H, 4.06; N, 12.10 Found: C, 55.3; H, 3.93; N, 12.24 300-MHz $^1$H-NMR (DMSO-$d_6$): 13.12 (s, 1H, exchangeable), 12.75 (s, 1H, exchangeable), 8.17 (d, J=8.7 Hz, 1H), 8.11 (d, J=2.0 Hz, 1H), 7.49 (dd, J=8.7, 2.0 Hz, 1H), 2.61 (d, J=7.0 Hz, 2H), 2.16 (m, 1H), 1.04 (d, J=6.7 Hz, 6H).

EXAMPLE 43

1-(Trimethylacetyloxy)-7-chloro-10-hydroxypyridazino[4,5-b]quinolin-4(3H)-one

Using a procedure similar to that described in Example 19 except starting with trimethylacetyl chloride, the title compound was obtained (68%) as a white powder, mp 352°–357° C.; MS(CI): 348 (M+H).

Analysis for $C_{16}H_{14}ClN_3O_4 \cdot 0.25$ $H_2O$: Calculated: C, 54.5; H, 4.15; N, 11.90 Found: C, 54.7; H, 4.17; N, 11.65 300-MHz $^1$H-NMR (DMSO-$d_6$): 13.13 (s, 1H, exchangeable), 12.73 (s, 1H, exchangeable), 8.17 (d, J=8.7 Hz, 1H), 8.11 (d, J=2.0 Hz, 1H), 7.47 (dd, J=8.7, 2.0 Hz, 1H), 1.38 (s, 9H).

EXAMPLE 44

1-(Isobutyryloxy)-7-chloro-10-hydroxypyridazino[4,5-b]quinolin-4(3H)-one

Using a procedure similar to that described in Example 19 except starting with isobutyryl chloride, the title compound was obtained (69%) as a white powder, mp 328°–335° C.; MS(CI): 334 (M+H).

Analysis for $C_{15}H_{12}ClN_3O_4 \cdot 0.2$ $H_2O$: Calculated: C, 53.4; H, 3.70; N, 12.46 Found: C, 53.4; H, 3.58; N, 12.32 300-MHz $^1$H-NMR (DMSO-$d_6$): 13.13 (s, 1H, exchangeable), 12.76 (br s, 1H, exchangeable), 8.17 (d, J=8.7 Hz, 1H), 8.11 (d, J=2.0 Hz, 1H), 7.48 (dd, J=8.7, 2.0 Hz, 1H), 2.95 (septet, J=7.0 Hz, 1H), 1.32 (d, J=7.0 Hz, 6H).

EXAMPLE 45

1-(Propionyloxy)-7-chloro-10-hydroxypyridazino[4,5-b]quinolin-4(3H)-one

Using a procedure similar to that described in Example 19 except starting with propionyl chloride, the title compound was obtained (79%) as a light yellow powder, mp 275°–278° C.; MS(CI): 320 (M+H).

Analysis for $C_{14}H_{10}ClN_3O_4 \cdot 0.1H_2O$: Calculated: C, 52.3; H, 3.20; N, 13.10 Found: C, 52.3; H, 3.31; N, 13.14 300-MHz $^1$H-NMR (DMSO-$d_6$): 13.13 (s, 1H, exchangeable), 12.75 (br s, 1H, exchangeable), 8.17 (d, J=8.7 Hz, 1H), 8.12 (d, J=2.0 Hz, 1H), 7.49 (dd, J=8.7, 2.0 Hz, 1H), 2.73 (q, J=7.5 Hz, 2H), 1.19 (t, J=7.5 Hz, 3H).

EXAMPLE 46

1-(Phenylacetyloxy)-7-chloro-10-hydroxypyridazino[4,5-b]quinolin-4(3H)-one

Using a procedure similar to that described in Example 19 except starting with phenylacetyl chloride, the title compound was obtained (24%), after purification by chromatography (eluant:methanol/methylene chloride; 2/98→5/95) over silica gel, as a white powder, mp 278°–282° C.; MS(CI): 382 (M+H).

Analysis for $C_{19}H_{12}ClN_3O_4$: Calculated: C, 59.8; H, 3.17; N, 11.00 Found: C, 59.6; H, 3.13; N, 11.04 300-MHz $^1$H-NMR (DMSO-$d_6$): 13.13 (s, 1H, exchangeable), 12.80 (s, 1H, exchangeable), 8.22 (d, J=8.7 Hz, 1H), 8.12 (s, 1H), 7.51 (dd, J=1.8, 8.7 Hz, 1H), 7.45–7.30 (m, 5H), 4.12 (s, 2H).

EXAMPLE 47

7,9-Dichloro-1-(phenylpropionyloxy)-10-hydroxypyridazino[4,5-b]quinolin-4(3H)-one Using a procedure similar to that described in Example 19 except starting with 7,9-dichloro-2,3-dihydro-10-hydroxypyridazino[4,5-b]-quinoline-1,4-dione, the title compound was obtained (21%), after recrystallization from ethyl acetate, as tan crystals, mp >395° C.; MS(CI): 430 (M+H).

Analysis for $C_{20}H_{13}Cl_2N_3O_4$ Calculated: C, 55.83; H, 3.02; N, 9.77 Found: C, 55.43; H, 3.31, N, 9.72 300-MHz $^1$H NMR (DMSO-$d_6$): 13.16 (s, 1H, exchangeable), 12.71 (s, 1H, exchangeable), 8.09 (d, J=2.0, 1H), 7.57 (d, J=2.0, 1H), 7.27 (m, 5H), 3.03 (s, 4H).

EXAMPLE 48

The diacylated product obtained from the reaction of 7-chloro-2,3-dihydro-10-hydroxypryridazino[4,5-b]quinoline-1,4-dione and isovaleryl chloride in pyridine Using a procedure similar to that described in Example 18 except starting with isovaleryl chloride, the title compound was obtained (42%) as an off-white powder, mp 255°–256° C.; MS(CI): 432 (M+H).

Analysis for $C_{21}H_{22}ClN_3O_5 \cdot 0.4\ H_2O$: Calculated: C, 57.4; H, 5.23; N, 9.57 Found: C, 57.4; H, 5.02; N, 9.81 300-MHz $^1$H-NMR (DMSO-$d_6$): 12.96 (s, 1H, exchangeable), 8.16 (m, 2H), 7.51(dd, J=8.8, 2.1 Hz, 1H), 2.96 (d, J=6.8 Hz, 2H), 2.65 (d, J=7.0 Hz, 2H), 2.20–2.12 (m, 2H), 1.05 (d, J=6.7 Hz, 6H), 1.02 (d, J=6.7 Hz, 6H).

EXAMPLE 49

The diacylated product obtained from the reaction of 7-chloro-2,3-dihydro-10-hydroxypyridazino[4,5-b]quinoline-1,4-dione and propionyl chloride in pyridine Using a procedure similar to that described in Example 18 except starting with propionyl chloride, the title compound was obtained (36%) as a beige solid, mp 283°–284° C.; MS(CI): 376 (M+H).

Analysis for $C_{17}H_{14}ClN_3O_5$: Calculated: C, 54.3; H, 3.76; N, 11.20 Found: C, 54.1; H, 3.71; N, 11.17 300-MHz $^1$H-NMR (DMSO-$d_6$): 12.98 (s, 1H, exchangeable), 8.16 (m, 2H), 7.51 (dd, J=2.0, 8.7 Hz, 1H), 3.09 (q, J=7.2 Hz, 2H), 2.77 (q, J=7.47 Hz, 2H), 1.22–1.13 (m, 6H).

EXAMPLE 50

The diacylated product obtained from the reaction of 7-chloro-2,3-dihydro-10-hydroxypyridazino[4,5-b]quinoline-1,4-dione and isobutyryl chloride in pyridine Using a procedure similar to that described in Example 18 except starting with isobutyryl chloride, the title compound was obtained (18%) as a white powder, mp 257°–260° C.; MS(CI): 404 (M+H).

Analysis for $C_{19}H_{18}ClN_3O_5 \cdot 0.8\ H_2O$: Calculated: C, 54.6; H, 4.72; N, 10.05 Found: C, 54.3; H, 4.33; N, 10.01 300-MHz $^1$H-NMR (DMSO-$d_6$): 12.98 (br s, 1H, exchangeable), 8.18 (d, J=8.7 Hz, 1H), 8.15 (d, J=1.9 Hz, 1H), 7.52 (dd, J=1.9, 8.7 Hz, 1H), 3.69 (septet, J=6.9 Hz, 1H), 2.99 (septet, J=7.0 Hz, 1H), 1.33 (d, J=7.0 Hz, 6H), 1.21 (d, J=6.9 Hz, 6H).

EXAMPLE 51

The diacylated product obtained from the reaction of 7,9-dichloro-2,3-dihydro-10-hydroxypyridazino[4,5-b]quinoline-1,4-dione and acetic anhydride in pyridine Using a procedure similar to that described for Example 16 except starting with 7,9-dichloro-2,3-dihydro-10-hydroxypyridazino-[4,5-b]quinoline-1,4-dione, the title compound was obtained (67%) as a tan solid, mp 315°–320° C.; MS(CI): 382 (M+H).

Analysis for $C_{15}H_9Cl_2N_3O_5$ Calculated: C, 47.14; H, 2.37; N, 11.00 Found: C, 47.15; H, 2.36; N, 11.04 300-MHz $^1$H NMR (DMSO-$d_6$): 12.9 (s, 1H, exchangeable), 8.12 (d, J=2.0, 1H), 7.61 (d, J=2.0, 1H), 2.64 (s, 3H), 2.38 (s, 3H).

EXAMPLE 52

The diacylated product obtained from the reaction of 2,3-dihydro-9-ethyl-10-hydroxypyridazino[4,5-b]quinoline-1,4-dione and acetic anhydride in pyridine Using a procedure similar to that described for Example 16 except starting with 2,3-dihydro-9-ethyl-10-hydroxypyridazino[4,5-b]-quinoline-1,4-dione, the title compound was obtained (61%) as a yellow solid, mp 238°–239° C.; MS(CI): 342 (M+H).

Analysis for $C_{17}H_{15}N_3O_5$ Calculated: C, 59.82, H, 4.43; N, 12.31 Found: C, 59.85; H, 4.41; N, 12.41 300-MHz $^1$H NMR (DMSO-$d_6$): 12.69 (s,1H, exchangeable), 7.97 (d, J=8.5 Hz, 1H), 7.68 (t, J=7.8 Hz, 1H), 7.22 (d, J=7.3 Hz, 1H), 3.25 (q, J=7.3 Hz, 2H), 2.64 (s, 3H), 2.38 (s, 3H), 1.14 (t, J=7.3 Hz, 3H).

EXAMPLE 53

The diacylated product obtained from the reaction of 7-chloro-2,3-dihydro-10-hydroxy-9-methylpyridazino[4,5-b]quinoline-1,4-dione and acetic anhydride in pyridine Using a procedure similar to that described for Example 16 except starting with 7-chloro-2,3-dihydro-10-hydroxy-9-methylpyridazino[4,5-b]quinoline-1,4-dione, the title compound was obtained 89(%) as an off white solid, mp 313.5°–314.5° C. MS(CI): 362 (M+H).

Analysis for $C_{16}H_{12}ClN_3O_5$ Calculated: C, 53.13; H, 3.34; N, 11.62 Found: C, 52.96; H, 3.30; N, 11.61 250-MHz $^1$H NMR (DMSO-$d_6$): 12.71 (s, 1H, exchangeable), 8.00 (s, 1H), 7.30 (s, 1H), 2.77 (s, 3H), 2.66 (s, 3H), 2.39 (s, 3H).

EXAMPLE 54

The diacylated product obtained from the reaction of 9-chloro-2,3-dihydro-10-hydroxy-7-methylpyridazino[4,5-b]quinoline-1,4-dione and acetic anhydride in pyridine Using a procedure similar to that described for Example 16 except starting with 9-chloro-2,3-dihydro-10-hydroxy-7-methylpyridazino[4,5-b]quinoline-1,4-dione, the title compound was obtained (76%) as an a light tan crystalline solid, mp 337°–339° C.; MS(CI): 362 (M+H).

Analysis for $C_{16}H_{12}ClN_3O_5$ Calculated: C, 53.13; H, 3.34; N, 11.62 Found: C, 53.00; H, 3.47; N, 11.59 250-MHz H NMR (DMSO-$d_6$): 12.74 (s, 3H), 7.83 (s, 1H), 7.33 (s, 1H), 2.65 (s, 3H), 2.41 (s, 3H), 2.38 (s, 3H).

EXAMPLE 55

The diacylated product obtained from the reaction of 9-bromo-2,3-dihydro-10-hydroxypyridazino[4,5-b]quinoline-1,4-dione and acetic anhydride in pyridine Using a procedure similar to that described for Example 16 except starting with 9-bromo-2,3-dihydro-10-hydroxypyridazino[4,5-b]-quinoline-1,4-dione, the title copmpound was obtained (75%), after recrystallization from dimethylsulfoxide/methanol, as a yellow crystalline solid, mp 305° C.; MS(CI): 392 (M+H).

Analysis for $C_{15}H_{10}BrN_3O_5 \cdot 0.27\ H_2O$ Calculated: C, 45.38; H, 2.68; N, 10.58 Found: C, 45.39; H, 2.74; N, 10.53 250-MHz $^1$H NMR (DMSO-$d_6$): 12.89 (s, 1H, exchangeable), 8.12 (dd, J=8.1, 1.4 Hz, 1H), 7.67 (m, 2H), 2.66 (s, 3H), 2.40 (s, 3H).

EXAMPLE 56

7-Chloro-2,3-dihydro-10-hydrazinopyridazino[4,5-b]quinoline-1,4-dione hydrochloride A stirred mixture of dimethyl 4,7-dichloroquinoline-2,3-dicarboxylate (2.0 g, 6.4 mM) and hydrazine monohydrate (9.26 mL, 191 mM) in ethanol (40 mL) was refluxed for 3 hr. During this period, the reaction mixture became thick with an orange solid and additional ethanol (60 mL) was added to facilitate stirring. After cooling to room temperature, the reaction mixture was filtered and the collected solids were washed with ethanol and air-dried to provide an orange solid (1.89 g). The solid was suspended in methanol (300 mL) and hydrogen chloride gas was bubbled into the stirred suspension for 5 min. After refusing the resulting mixture for 2 hr, it was cooled to room temperature and filtered to separate the solids. The collected solids were washed with methanol to provide (1.85 g, 85%), after drying in vacuo at 100° C. for 20 hr, the title compound as a dark orange powder, mp >300° C.; MS(CI): 278 (M+H).

Analysis for $C_{11}H_8ClN_5O_2 \cdot 1.75$ HCl Calculated: C, 38.7; H, 2.88; N, 20.5 Found: C, 38.8; H, 3.16; N, 20.7 300-MHz $^1$H-NMR (DMSO-$d_6$): 8.32 (d, J=2.0 Hz, 1H), 8.26 (br d, J=8.5 Hz, 1H), 7.72 (br d, J=9.4 Hz, 1H).

EXAMPLE 57

10-(2-Carboxyethylamino)-7-chloro-2,3-dihydropyridazino[4,5-b]quinoline-1,4-dione A mixture of 10-(2-ethoxycarbonylethylamino)-7-chloro-2,3-dihydropyridazino[4,5-b]quinoline-1,4-dione (0.08 g, 0.22 mM) and 1N hydrochloric acid was refluxed for 1 hr and then cooled to room temperature and filtered. The collected orange solid was washed with water and air dried to provide (0.07 g, 97%) the title compound as an orange powder, mp 356°–359° C.; MS(CI): 335 (M+H).

Analysis for $C_{14}H_{11}ClN_4O_4 \cdot 0.3$ $H_2O$: Calculated: C, 49.4; H, 3.44; N, 16.47 Found: C, 49.3; H, 3.23; N, 16.25 300-MHz $^1$H-NMR (DMSO-$d_6$): 13.50 (br s, 0.25 H, exchangeable), 12.65–12.30 (br m, 1.5 H, exchangeable), 9.66 (br s, 0.25 H exchangeable), 8.41 (d, J=8.7 Hz, 0.5H), 8.30 (s, 0.5H), 8.14 (m, 1H), 7.88 (d, J=8.4 Hz, 0.5H), 7.59 (d, J=7.8 Hz, 0.5H), 3.66–3.64 (br m, 2H), 2.69–2.60 (br m, 2H).

The starting 10-(2-ethoxycarbonylethylamino)-7-chloro-2,3-dihydropyridazino[4,5-b]quinoline-1,4-dione was prepared as follows:

a. 10-(2-Ethoxycarbonylethylamino)-7-chloro-2,3-dihydropyridazino-[4,5-b]quinoline-1,4-dione.

A mixture of 7-chloro-2,3-dihydro-10-hydrazinopyridazino[4,5-b]-quinoline-1,4-dione hydrochloride (1.0 g, 2.9 mM, as prepared in Example 56) and beta alanine ethyl ester hydrochloride (49.0 g, 320 mM) in pyridine (52 mL) was refluxed for 23 hr. After cooling, the vigorously stirred reaction mixture was diluted slowly with water (100 mL) and then filtered to separate a fine red solid. The collected solids were washed with water and chromatographed (eluant: methanol/methylene chloride; 5/95) over silica gel to provide the title ester (0.13 g, 13%) as a red powder, mp 258°–260° C.; MS(CI): 363 (M+H).

Analysis for $C_{16}H_{15}ClN_4O_4 \cdot 0.1H_2O$ Calculated: C, 52.7; H, 4.20; N, 15.4 Found: C, 52.6; H, 4.26; N, 15.7 300-MHz $^1$H-NMR (DMSO-$d_6$): 13.50 (br s, 0.3 H, exchangeable), 12.60–12.10 (br m, 1.7H, exchangeable), 9.60 (br m, 0.3 H, exchangeable), 8.40–8.30 (br m, 1H), 8.16–8.12 (br m, 1H), 7.85 (br m, 0.3 H), 7.55 (br m, 0.7 H), 4.08 (q, J=7.1 Hz, 2H), 3.69 (m, 2H), 2.71 (m, 2H), 1.19 (t, J=7.1 Hz, 3H).

EXAMPLE 58

The triacylated product obtained from the reaction of 7-chloro-2,3-dihydro-10-hydroxypyridazino[4,5-b]quinoline-1,4-dione with trimethylacetyl chloride in pyridine A mixture of 7-chloro-2,3-dihydro-10-hydroxypyridazino[4,5-b]quinoline-1,4-dione (1.00 g, 3.8 mM) and trimethylacetyl chloride (4.68 mL, 38 mM) in pyridine (15 mL) was stirred for 7 days at room temperature. The cooled (methanol/ice bath) mixture was diluted with ice/methanol (25 mL) with vigorous stirring to give a white suspension. This suspension was stirred vigorously for another 5 minutes and collected. The white solids were washed well with ice/methanol and sucked dry. The solids were suspended in methanol (1200 mL) and refiltered. The solid was sucked dry on the filter under a stream of nitrogen to give (1.35 g, 69%), after drying in vacuo at 100° C. for 20 hrs., the title compound as a white powder, mp 296°–297° C.

Analysis for $C_{26}H_{30}ClN_3O_6$: Calculated: C, 60.5; H, 5.86; N, 8.14 Found: C, 60.3; H, 5.80; N, 8.19 300-MHz $^1$H NMR (CDCl$_3$): 8.13 (d, J=2.0 Hz, 1H), 8.09–8.06 (d, J=9.0 Hz, 1H), 7.69–7.65 (dd, J=2.0 Hz, J=9.0 Hz, 1H), 1.55 (s, 9H), 1.54 (s, 9H), 1.42 (s, 9H).

EXAMPLE 59

10-Amino-7-chloro-2,3-dihydropyridazino[4,5-b]quinoline-1,4-dione hydrochloride

A mixture of 4-amino-7-chloroquinoline-2,3-dicarboximide (1.3 g, 5.3 mM) and hydrazine monohydrate (7.64 mL, 158 mM) in ethanol (56 mL) was stirred at reflux for 3 hr and the resulting thick mixture then cooled to room temperature. The mixture was filtered to separate the yellow solids which were washed with ethanol and air dried to give (1.32 g) of a gold colored solid. A portion of this material (0.90 g) was refluxed in 2N hydrochloric acid for 2 hr, cooled and filtered. The collected solids were washed with water and dried to provide (0.71 g, 65%) the title compound as a yellow powder, mp >400° C.; MS (CI): 263 (M+H).

Analysis for $C_{11}H_7ClN_4O_2 \cdot HCl \cdot 0.5$ $H_2O$: Calculated: C, 42.9; H, 2.94; N, 18.20 Found: C, 43.0; H, 2.92; N, 18.18 300-MHz $^1$H-NMR (DMSO-$d_6$): 12.53 (br s, 1H, exchangeable), 11.26 (s, 1H, exchangeable), 10.90 (s, 1H, exchangeable), 8.86 (d, J=9.0 Hz, 1H), 8.31 (d, J=2.0 Hz, 1H), 7.83 (dd, J=2.0, 9.0 Hz, 1H).

The starting 4-amino-7-chloroquinoline-2,3-dicarboximide was prepared in the following manner:

a. 4-Amino-7-chloroquinoline-2,3-dicarboximide.

Ammonia gas was bubbled through a cold (ice bath) stirred solution of dimethyl 4,7-dichloroquinoline-2,3-dicarboxylate (1.90 g, 6.05 mM) in methanol (200 mL) for 10 min. The resluting solution was then heated (260° C.) in a stainless steel pressure vessel for 1 hr and then cooled to room temperature. The resulting mixture was filtered and the collected solids were washed with methanol and dried in vacuo at 100° C. for 6 hr to provide (1.53 g, 100%) the title compound as a green solid, mp >300° C.; MS(CI): 248 (M+H).

Analysis for $C_{11}H_6ClN_3O_2$: Calculated: C, 53.3; H, 2.44; N, 16.97 Found: C, 53.3; H, 2.62; N, 16.91 300-MHz $^1$H-NMR (DMSO-$d_6$): 11.35 (br s, 1H, exchangeable), 8.53 (d, J =8.9 Hz, 1H), 8.05 (d, J=2.2 Hz, 1H), 7.69 (dd, J=8.9, 2.2 Hz, 1H).

EXAMPLE 60

The diacylated product obtained from the reaction of 10-amino-7-chloro-2,3-dihydropyridazino[4,5-b]quinoline-1,4-dione hydrochloride with acetic anhydride in pyridine A mixture of 10-amino-7-chloro-2,3-dihydropyridazino [4,5-b]-quinoline-1,4-dione hydrochloride (1.00 g, 3.3 mM) in acetic anhydride (16 mL) and pyridine (16 mL) was stirred at room temperature for 24 hr. The resulting mixture was filtered and the collected solids were washed with acetic anhydride and dried to give a tan powder. This material was stirred with methanol (65 mL) for 2 hr at room temperature and the resulting suspension filtered. The collected solids were washed with methanol and dried in vacuo at 100° C. for 65 hr to provide (0.66 g, 58%) the title compound as a tan solid, mp 221°–223° C.; MS(CI): 347 (M+H).

Analysis for $C_{15}H_{11}ClN_4O_4$: Calculated: C, 52.0; H, 3.20; N, 16.20 Found: C, 51.6; H, 3.34; N, 16.14 300-MHz $^1$H-NMR (DMSO-$d_6$): 9.67 (br s, 1H, exchangeable), 9.21 (br s, 1H, exchangeable), 8.57 (d, J=9.1 Hz, 1H), 7.95 (d, J=2.2 Hz, 1H), 7.69 (dd, J=2.2, 9.1 Hz, 1H), 2.63 (s, 3H), 2.48 (s, 3H).

EXAMPLE 61

7-Chloro-2,3-dihydro-10-hydroxypyridazino[4,5-b]quinoline-1,4-dione choline salt To a stirred suspension of 7-chloro-2,3-dihydro-10-hydroxypyridazino-[4,5-b]quinoline-1,4-dione (1.00 g, 3.8 mM) in water (40 mL) was added choline hydroxide (0.86 mL, 3.8 mM, 50 weight per cent, aqueous solution). Toluene (250 mL) was added to the resulting solution and the mixture was concentrated using a rotary evaporator. The residue was diluted with toluene (250 mL) and the resulting mixture concentrated again to provide a yellow residue. This residue was stirred for 60 hr with methanol (25 mL) and the resulting suspension was filtered to separate the solids which were washed with methanol (3 mL) and then dried under a stream of nitrogen for 1 hr. Further drying of the solids in vacuo at 100° C. for 20 hr provided (0.76 g, 55%) of the title compound as a yellow powder, mp 267°–269° C.

Analysis for $C_{11}H_5ClN_3O_3 \cdot C_5H_{14}NO$ Calculated: C, 52.4; H, 5.22; N, 15.30 Found: C, 52.2; H, 5.22; N, 15.03 300-MHz $^1$H-NMR (DMSO-$d_6$): 14.72 (s, 1H, exchangeable), 11.16 (br s, 1H, exchangeable), 8.20 (d, J=8.67 Hz, 1H), 7.79 (t, J=2.16 Hz, 1H), 7.33–7.29 (dt, J=2.13 Hz, J=8.76 Hz, 1H), 5.40 (br m, 0.7 H, exchangable), 3.87–3.82 (m, 2H), 3.42–3.38 (m, 2H), 3.11 (s, 9H).

EXAMPLE 62

7-Chloro-2,3-dihydro-10-hydroxypyridazino[4,5-b]quinoline-1,4-dione dicholine salt Using a procedure similar to that described in Example 61 except employing 2.1 mole equivalents of choline hydroxide, the title compound was obtained (80%) as a hygroscopic yellow solid, mp 175°–178° C.

Analysis for $C_{11}H_4ClN_3O_3 \cdot 2C_5H_{14}NO \cdot H_2O$: Calculated: C, 51.7; H, 7.02; N, 14.35 Found: C, 51.4; H, 6.86; N, 14.30 300-MHz $^1$H-NMR (DMSO-$d_6$): 8.06 (d, J=8.7 Hz, 1H), 7.53 (br m, 1H), 6.96 (br m, 1H), 3.91 (m, 4H), 3.46 (m, 4H), 3.15 (s, 18H).

EXAMPLE 63

2,3-Dihydro-9-ethyl-10-hydroxypyridazino[4,5-b]quinoline-1,4-dione choline salt

Using a procedure similar to that described in Example 61 except starting with 2,3-dihydro-9-ethyl-10-hydroxypyridazino[4,5-b]quinoline-1,4-dione, the title compound was obtained (100%) as a dull yellow powder, mp 227°–229° C.

Analysis for $C_{13}H_{10}N_3O_3 \cdot C_5H_{14}NO \cdot 0.5\ H_2O$: Calculated: C, 58.5; H, 6.82; N, 15.1 Found: C, 58.9; H, 6.95; N, 14.7 300-MHz $^1$H-NMR (DMSO-$d_6$): 10.98 (br s, 1H, exchangeable), 7.62 (d, J=7.7 Hz, 1H), 7.47 (t, J=7.1 Hz, 1H), 7.01 (d, J=6.9 Hz, 1H), 3.84 (m, 2H), 3.51–3.34 (m, 4H), 3.10 (s, 9H), 1.22 (t, J=7.3 Hz, 3H).

EXAMPLE 64

7-Chloro-2,3-dihydro-10-hydroxypyridazino[4,5-b]quinoline-1,4-dione tetrabutylammonium salt Using a procedure similar to that described for Example 61 except using tetrabutylammonium hydroxide as the base, the title compound was obtained (47%) as a yellow powder, mp 187°–189° C.

Analysis for $C_{11}H_5ClN_3O_3 \cdot 0.9(C_4H_9)_4N \cdot 0.5\ H_2O$: Calculated: C, 62.3; H, 7.90; N, 11.15 Found: C, 62.2; H, 7.64; N, 10.74 300-MHz $^1$H-NMR (DMSO-$d_6$): 14.71 (s, 1H, exchangeable), 11.14 (br s, 1H, exchangeable), 8.19 (d, J=8.7 Hz, 1H), 7.78 (t, J=2.0 Hz, 1H), 7.30( dt, J=2.0, 8.7 Hz, 1H), 3.15 (m, 8H), 1.61–1.51 (br m, 8H), 1.36–1.24 (m, 8H), 0.93 (t, J=7.2 Hz, 12H).

EXAMPLE 65

7,9-Dichloro-2,3-dihydro-10-hydroxypyridazino[4,5-b]quinoline-1,4dione choline salt Using a procedure similar to that described for Example 61 except starting with 7,9-dichloro-2,3-dihydro-10-hydroxypyridazino-[4,5-b]quinoline-1,4-dione, the title compound was obtained (30%), after recrystallization from ethanol/diethyl ether, as a yellow solid, mp 220°–222° C. (dec).

Analysis for $C_{11}H_4Cl_2N_3O_3 \cdot C_5H_{14}NO \cdot 0.4\ H_2O$ Calculated: C, 47.05; H, 4.64; N, 13.72 Found: C, 47.08; H, 4.70; N, 13.54 250-MHz $^1$H NMR (DMSO-$d_6$): 14.83 (s, 1H, exchangeable), 11.24 (s, 1H, exchangeable), 7.72 (d, J=2.0, 1H), 7.30 (d, J=2.0, 1H), 3.82 (t, J=5.0, 1H), 3.38 (t, J=5.0, 2H), 3.11 (s, 9H).

EXAMPLE 66

7-Bromo-2,3-dihydro-10-hydroxypyridazino[4,5-b]quinoline-1,4-dione choline salt

To a suspension of 7-bromo-2,3-dihydro-10-hydroxypyridazino-[4,5-b]quinoline-1,4-dione (0.600 g, 1.95 mM) in methanol (20 mL) was added choline hydroxide (0.24 g, 1.98 mM, 45% solution in methanol). The resulting solution was concentrated and the solid yellow residue was recrystallized from ethanol to provide (0.62 g, 78%) the title compound as yellow crystals, mp 227.5°–228.5° C.

Analysis for $C_{11}H_5BrN_3O_3 \cdot C_5H_{14}NO \cdot 0.6\ C_5H_5OH \cdot 0.2\ H_2O$ Calculated: C, 46.69; H, 5.241 N, 12.66 Found: C, 46.731 H, 5.33; N, 12.31 250-MHz $^1$H NMR (DMSO-$d_6$): 14.71 (s, 1H, exchangeable), 11.16 (s, 1H, exchangeable), 8.12 (d, J=8.8 Hz, 1H), 7.96 (d, J=1.8 Hz, 1H), 7.42 (dd, J=8.8 Hz, 1H), 5.3 (br s, 1H, exchangeable), 4.35 (br s, 6H, exchangeable, OH of ethanol), 3.84 (s, 2H), 3.42 (m, 3.5H, includes $CH_2$ of ethanol), 3.11 (s, 9H), 1.05 (t, J=7.0 Hz, 2H, $CH_3$ of ethanol).

EXAMPLE 67

7-Chloro-2,3-dihydro-10-thiohydroxypyridazino[4,5-b]quinoline-1,4-dione choline salt Using a procedure similar to that described in Example 66 except starting with 7-chloro-2,3-dihydro-10- thiohydroxypyridazino[4,5-b]-quinoline-1,4-dione, the title compound was obtained (52%) as orange crystals, mp 237°–238.5° C. (dec).

Analysis for $C_{16}H_{19}ClN_4O_3S$ Calculated: C, 50.19; H, 5.00; N, 14.63 Found: C, 50.23; H, 4.98; N, 14.72 250-MHz $^1H$ NMR (DMSO-$d_6$): 14.82 (s, 1H, exchangeable); 11.43 (s, 1H, exchangeable), 8.85 (dd, J=9.3, 2.3 Hz, 1H), 7.92 (d, J=2.0 Hz, 1H), 7.51 (dd, J=9.3, 2.0 Hz, 1H), 5.30 (br s, 1H, exchangeable), 3.83 (m, 2H), 3.40 (m, 2H), 3.11 (s, 9H).

EXAMPLE 68

7-Bromo-2,3-dihydro-9-ethyl-10-hydroxypyridazino [4,5-b]quinoline-1,4-dione choline salt Using a procedure similar to that described in Example 66 except starting with 7-bromo-2,3-dihydro-9-ethyl-10-hydroxypyridazino[4,5-b]-quinoline-1,4-dione, the title compound was obtained (64%) as yellow crystals, mp 197°–199° C.

Analysis for $C_{13}H_9BrN_3O_3.C_5H_{14}NO.H_2O$ Calculated: C, 47.27; H, 5.51; N, 12.25 Found: C, 47.30; H, 5.19; N, 12.16 250-MHz $^1H$ NMR (DMSO-$d_6$): 15.43 (s, 1H, exchangeable), 7.78 (d, J=2.0 Hz, 1H), 7.13 (d, J=2.0 Hz, 1H), 5.36 (br s, 1H, exchangeable), 3.83 (m, 2H), 3.36 (m, 4H), 3.11(s, 9H), 1.21 (t, J=7.2 Hz, 3H).

EXAMPLE 69

7-Chloro-2,3-dihydro-9-methyl-10-hydroxypyridazino[4,5-b]quinoline-1,4-dione choline salt Using a procedure similar to that described in Example 66 except starting with 7-chloro-2,3-dihydro-9-methyl-10-hydroxypyridazino[4,5-b]quinoline-1,4-dione, the title compound was obtained (96%) as yellow crystals, mp 210.5°–212.5° C.

Analysis for $C_{12}H_7ClN_3O_3.C_5H_{14}NO.0.25\ H_2O$ Calculated: C, 52.99; H, 5.62; N, 14.53 Found: C, 53.07; H, 5.57; N, 14.25 300-MHz $^1H$ NMR (DMSO-$d_6$): 15.35 (s, 1H, exchangeable), 11.10 (s, 1H, exchangeable), 7.59 (d, J=1.6 Hz, 1H), 7.01 (d, J=1.6 Hz, 1H), 5.36 (br s, exchangeable, 1H), 3.84 (m, 2H), 3.40 (m, 2H), 3.11 (s, 9H), 2.89 (s, 3H).

EXAMPLE 70

9-Chloro-2,3-dihydro-7-methyl-10-hydroxypyridazino[4,5-b]quinoline-1,4-dione choline salt Using a procedure similar to that described in Example 66 except starting with 9-chloro-2,3-dihydro-7-methyl-10-hydroxypyridazino[4,5-b]quino-line-1,4-dione, the title compound was obtained (92%) as yellow crystals, mp 190°–192° C.

Analysis for $C_{12}H_7ClN_3O_3.C_5H_{14}NO.0.26\ H_2O$ Calculated: C, 52.96; H, 5.63; N, 14.53 Found: C, 52.96; H, 5.67; N, 14.34 300-MHz $^1H$ NMR (DMSO-$d_6$): 15.28 (s, 1H, exchangeable), 11.08 (s, 1H, exchangeable), 7.50 (s, 1H), 7.11 (s, 1H), 5.31 (br s, 1H, exchangeable), 3.83 (br s, 2H), 3.39 (m, 2H), 3.10 (s, 9H), 2.39 (s, 3H).

EXAMPLE 71

2,3-Dihydro-10-hydroxy-7-iodopyridazino[4,5-b] quinoline-1,4-dione choline salt

Using a procedure similar to that described in Example 66 except starting with 2,3-dihydro-10-hydroxy-7-iodopyridazino[4,5b]quinoline-1,4-dione, the title compound was obtained (75%) as yellow crystals, mp 219°–220° C.

Analysis for $C_{11}H_5IN_3O_3.C_5H_{14}NO$ Calculated: C, 41.94; H, 4.18; N, 12.23 Found: C, 41.84; H, 4.23; N, 12.10 250-MHz $^1H$ NMR (DMSO-$d_6$): 14.71 (s, 1H, exchangeable), 11.13 (s, 1H, exchangeable), 8.19 (d, J=1.4 Hz, 1H), 7.93 (d, J=8.6 Hz, 1H), 7.57 (dd, J=8.6, 1.4 Hz, 1H), 5.30 (br s, 1H, exchangeable), 3.83 (m, 2H), 3.39 (m, 2H), 3.10 (s, 9H).

EXAMPLE 72

The following illustrate representative pharmaceutical dosage forms containing a compound of formula I, or a pharmaceutically acceptable sal thereof, for example as illustrated in any of the previous Examples, (hereafter referred to as "compound X"), for thereapeutic or prophylactic use in humans:

(a) Tablet

|  | mg/tablet |
|---|---|
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |

(b) Capsule

|  |  |
|---|---|
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

EXAMPLE 73

This is an example of a formulation suitable for parenteral use made with the compound of Example 2:

| Parenteral Formulation: | mg/mL |
|---|---|
| Compound | 10.0 |
| Meglumine | 19.5 |
| Dextrose, anhydrous | 39.5 |
| Sterile Water for Injection | qs ad 1 mL |

The solution was prepared by conventional measures well known in the pharmaceutical field.

General formulations for this class of compounds and their salts, other than for acylated compounds, may be prepared by solubilizing the active compound in an aqueous meglumine (N-methyl-glucamine) solution containing an equimolar, or if solubilization is difficult, a molar excess of meglumine relative to Compound. Choline salts are preferred for use in making formulations. Excipients such has dextrose may be added to adjust the osmolality of the formulation. Water for Injection is added to bring the solution to final volume. Alternately, other amine bases such as tromethamine or l-arginine may be used to solubilize the active compound.

EXAMPLE 74
A formulation is made as in Example 73, except that the choline salt of Compound X is used in place of the compound of Example 2.
EXAMPLE 75
A formulation is made comprising a 5% aqueous solution of dextrose made to 10 mg/mL in the choline salt of Compound X.
FORMULAE
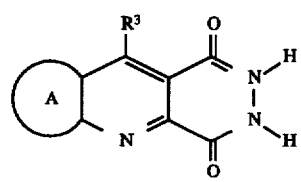   I
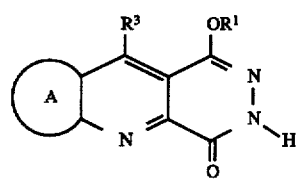   I'
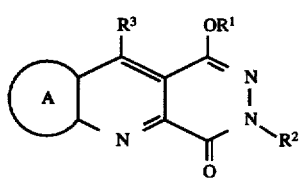   I''
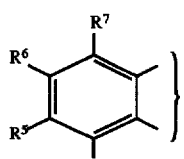   Ia
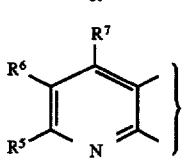   Ib
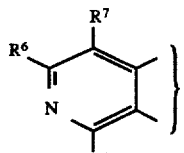   Ic
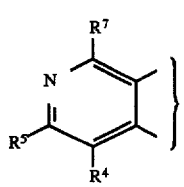   Id
-continued
FORMULAE
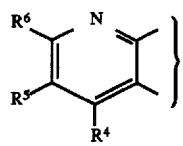   Ie
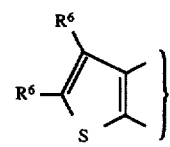   If
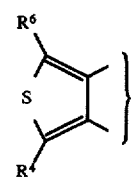   Ig
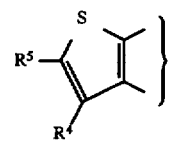   Ih
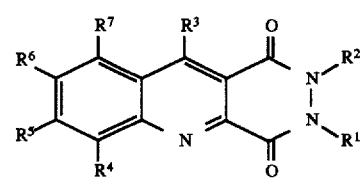   IIa
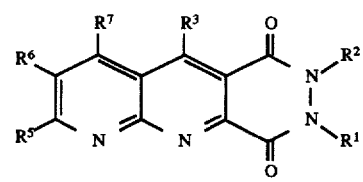   IIb
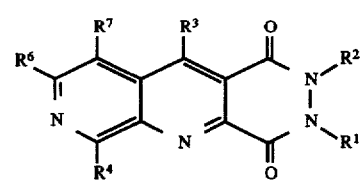   IIc
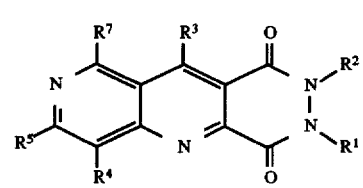   IId
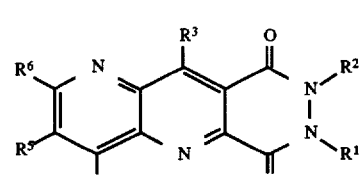   IIe -continued
FORMULAE
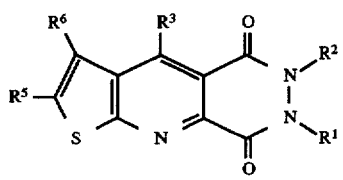 IIf
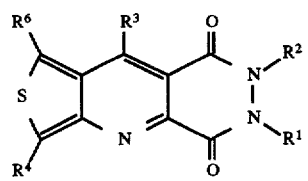 IIg
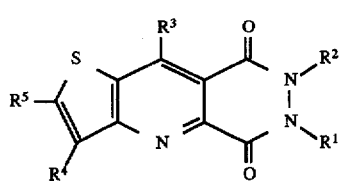 IIh
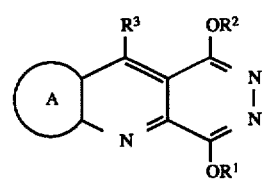 III
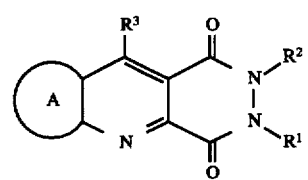 IIIa
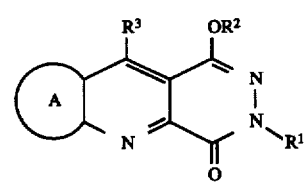 IIIb
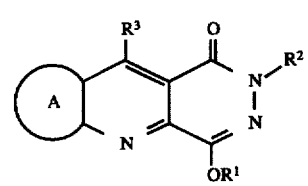 IIIc
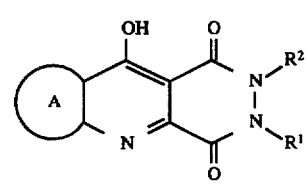 IIId
-continued
FORMULAE
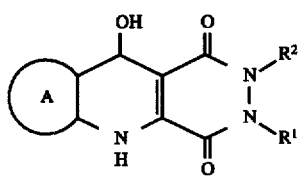 IIIe
 IV
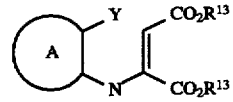 V
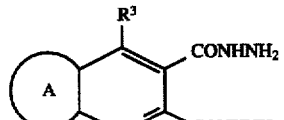 IVa
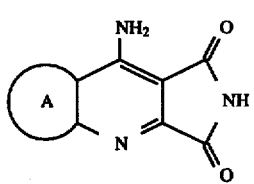 IVb
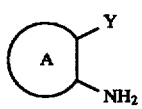 VI
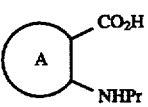 VIa
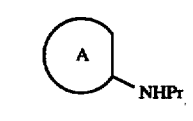 VIb
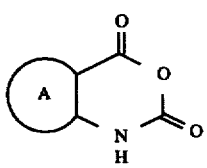 VIc
VII -continued
FORMULAE

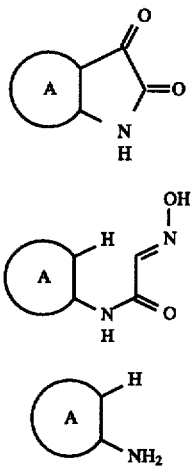

What is claimed is:

1. A method for the treatment of stroke, hypoglycemia, ischemic attack, anoxia, and epilepsy comprising administering to a mammal in need of such treatment an effective amount of compound obtained by mono-, di-, or tri-acylating at a ring amino, hydrazino, hydroxy, thiohydroxy, or oxo-oxygen substituent or a ring nitrogen a compound of formula I with an acylating agent having the formula $R^8COX'$, or a pharmaceutically acceptable salt thereof, wherein X' is a conventional leaving group and wherein $R^8$ is selected from (1) hydrogen, (2) (1–12C)alkyl which may contain a double or triple bond, and which may bear a group selected from (a) CN, $OR^e$, and $CO_2R^e$, wherein $R^e$ is selected from hydrogen, (1–4C)alkyl, and phenyl and phenyl (1–4C)alkyl the phenyl rings of which can be substituted with from 0–3 substituents selected from halo, amino, hydroxy, cyano, nitro, (1–4C)alkyl, and (1–4C)alkoxy;

(b) $NR^f_2$ and $CONR^f_2$ wherein each $R^f$ is independently selected from (1) from $R^h$, $COR^h$, and $COOR^h$ when said group is $NR^f2$ and (2) from the values of $R^h$ when the said group is $CONR^f_2$, wherein $R^h$ can have any of the values stated above for $R^e$, or wherein, for either of the said groups, the two $R^f$ values, together with the nitrogen to which they are attached, form with carbon a saturated 4- to 7-membered ring selected from piperidinyl, pyrrolidinyl and azetidinyl, (3) $NR^g_2$ wherein each $R^g$ can independently have any of the values stated above for $R^e$, or wherein the two $R^g$ groups together with the nitrogen to which they are attached form with carbon a saturated 4- to 7-membered ring selected from piperidinyl, pyrrolidinyl and azetidinyl, (4) pyridyl, pyridyl(1–12C)alkyl, (5) phenyl, and phenyl(1–4C)alkyl wherein the phenyl rings can be substituted with from 0–3 substituents selected from halo, amino, hydroxy, cyano, nitro, (1–4C)alkyl, and (1–4C)alkoxy;

or a product obtained by mono-, di-, or tri-alkylating at a ring amino, hydrazino, hydroxy, thiohydroxy, or oxo-oxygen substituent or a ring nitrogen a compound of formula I with an alkylating agent having the formula $R^{12}X$, or a pharmaceutically acceptable salt thereof, wherein X is a conventional leaving group and wherein $R^{12}$ is selected from (1–4C)alkyl which may contain a double or triple bond provided that, if a double or triple bond is present on a C3 or C4 carbon chain, a methylene group intervenes between said double or triple bond and the leaving group X to which said alkyl is attached, phenyl(1–4C)alkyl wherein the phenyl ring can be substituted with from 0–3 substituents selected from halo, amino, hydroxy, cyano, nitro, (1–4C)alkyl, and (1–4C)alkoxy, and $(CH_2)_mCOOR^a$ wherein $R^a$ is hydrogen or (1–4C)alkyl and m is 1–6; wherein, Formula I is:

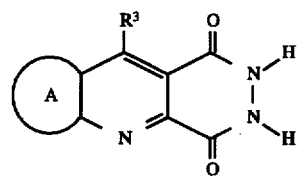

or a pharmaceutically acceptable salt thereof, wherein:

$R^3$ is selected from hydrogen, amino, hydrazino, hydroxy and thiohydroxy; ring A is of the formula Ia

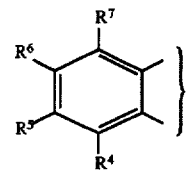

wherein $R^4$, $R^5$, $R^6$, and $R^7$ are independently selected from the group consisting of hydrogen, halo, (1–4C)alkyl which may contain a double or triple bond if said (1–4C)alkyl is a (2–4C)alkyl, (1–3C) perfluoroalkyl, (1–3C)alkyl substituted with trifluoromethyl, nitro, $OR^d$, $CO_2R^d$, CN, $NR^d_2$ and cyclopropyl, wherein each $R^d$ is independently selected from hydrogen and (1–4C) alkyl; but excluding compounds wherein:

a) said compound is of formula I, ring A has formula Ia, and $R^3$–$R^7$ are each hydrogen;

b) said compound is a product made by monoacetylating, diacetylating, or diethylating a compound of formula I wherein ring A has formula Ia and $R^3$–$R^7$ are each hydrogen; and c) said compound is of formula I, ring A has formula Ia, $R^4$ and $R^5$ are each $OCH_3$, $R^3$ is hydrogen and $R^6$–$R^7$ are hydrogen.

2. A method according to claim 1 wherein the compound is of formula I' or I",

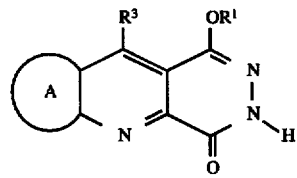

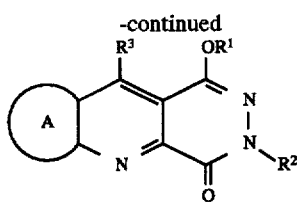

or a pharmaceutically acceptable salt thereof, wherein:
$R^1$ and $R^2$ are independently selected from:
hydrogen,
(1–4C)alkyl which may contain a double or triple bond provided that, if a double or triple bond is present, a methylene group intervenes between said double or triple bond and the atom to which said alkyl is attached, and
$COR^8$ wherein $R^8$ is selected from
(1) (1–12C)alkyl which may contain a double or triple bond, or which may bear a group selected from
(a) CN, $OR^e$, and $CO_2R^e$, wherein $R^e$ is selected from hydrogen, (1–4C)alkyl, and phenyl and phenyl(1–4C)alkyl the phenyl rings of which can be substituted with from 0–3 substituents selected from halo, amino, hydroxy, cyano, nitro, (1–4C)alkyl, and (1–4C)alkoxy;
(b) $NR^f_2$ and $CONR^f_2$ wherein each $R^f$ is independently selected (1) from $R^h$, $COR^h$, and $COOR^h$ when the said group is $NR^f2$ and (2) from the values of $R^h$ when the said group is $CONR^f2$, wherein $R^h$ can have any of the values stated above for $R^e$, or wherein, for either of the said groups, the two $R^f$ values, together with the nitrogen to which they are attached, form with carbon a saturated 4- to 7-membered ring selected from piperidinyl, pyrrolidinyl and azetidinyl,
(2) $NR^g_2$ wherein each $R^g$ can independently have any of the values stated above for $R^e$, or wherein the two $R^g$ groups together with the nitrogen to which they are attached form with carbon a saturated 4- to 7-membered ring selected from piperidinyl, pyrrolidinyl and azetidinyl,
(3) pyridyl, pyridyl(1–12C)alkyl,
(4) phenyl, and phenyl(1–4C)alkyl wherein the phenyl rings can be substituted with from 0–3 substituents selected from halo, amino, hydroxy, cyano, nitro, (1–4C)alkyl, and (1–4C)alkoxy;
$R^3$ is selected from hydrogen, hydrazino, $OR^9$, $NHR^{10}$, and $SR^9$, wherein
$R^9$ is selected from
(i) hydrogen,
(ii) (1–4C)alkyl which may contain a double or triple bond, provided that, if a double or triple bond is present, a methylene group intervenes between said double or triple bond and the oxygen, nitrogen, or sulfur to which said alkyl is attached and
(iii) $(CH_2)_pCOOR^c$ wherein $R^c$ is hydrogen or (1–4C)alkyl and p is 1–6; and
$R^{10}$ is selected from hydrogen and $(CH_2)_nCOOR^b$ wherein $R^b$ is hydrogen or (1–4C)alkyl and n is 1–6.

3. A method according to claim 2, wherein $R^1$ and $R^2$ are each independently selected from hydrogen and any of the values for $COR^8$.

4. A method for the treatment of stroke, hypoglycemia, ischemic attack, anoxia, and epilepsy comprising administering to a mammal in need of such treatment an effective amount of compound obtained by mono or diacylating at a ring amino, hydrazino, hydroxy, thiohydroxy, or oxo-oxygen substituent or a ring nitrogen a compound of formula I

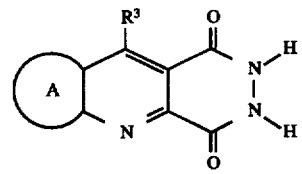

or a pharmaceutically acceptable salt thereof, wherein:
$R^3$ is selected from hydrogen, amino, hydrazino, hydroxy and thiohydroxy; and ring A is of the formula Ia

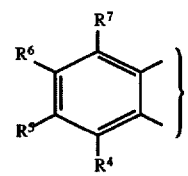

wherein $R^4$, $R^5$, $R^6$, $R^7$ are independently selected from the group consisting of hydrogen, halo, (1–4C)alkyl which may contain a double or triple bond, (1–3C) perfluoroalkyl, (1–3C)alkyl substituted with trifluoromethyl, nitro, $OR^d$, $CO_2R^d$, $CONR^d_2$, CN, $NR^d2$, and cyclopropyl, wherein each $R^d$ is independently selected from hydrogen and (1–4C)alkyl but excluding those compounds which are products made by monoacetylation or diacetylation a compound of formula I wherein ring A has formula Ia and $R^3$–$R^7$ are each hydrogen, and wherein the acylating agent is chosen from a compound of the formula $R^8COX'$ wherein X' is a conventional leaving group and wherein $R^8$ is selected from
(1) hydrogen,
(2) (1–12C)alkyl which may contain a double or triple bond, and which may bear a group selected from
(a) CN, $OR^e$, and $CO_2R^e$, wherein $R^e$ is selected from hydrogen, (1–4C)alkyl, and phenyl and phenyl(1–4C)alkyl the phenyl rings of which can be substituted with from 0–3 substituents selected from halo, amino, hydroxy, cyano, nitro, (1 –4C) alkyl, and (1–4C)alkoxy;
(b) $NR^f_2$ and $CONR^f_2$ wherein each $R^f$ is independently selected from (1) from $R^h$, $COR^h$, and $COOR^h$ when said group is $NR^f_2$ and (2) from the values of $R^h$ when the said group is $CONR^f_2$, wherein $R^h$ can have any of the values stated above for $R^e$, or wherein, for either of the said groups, the two $R^f$ values, together with the nitrogen to which they are attached, form with carbon a saturated 4- to 7-membered ring selected from piperidinyl, pyrrolidinyl and azetidinyl,
(3) $NR^g_2$ wherein each $R^g$ can independently have any of the values stated above for $R^e$, or wherein the two $R^g$ groups together with the nitrogen to which they are attached form with carbon a saturated 4- to 7-membered ring selected from piperidinyl, pyrrolidinyl and azetidinyl,
(4) pyridyl, pyridyl(1–12C)alkyl, (5) phenyl, and phenyl(1–4C)alkyl wherein the phenyl rings can be substituted with from 0–3 substituents selected from halo, amino, hydroxy, cyano, nitro, (1–4C)alkyl, and (1–4C)alkoxy or a pharmaceutically acceptable salt thereof.

5. A method according to claim 4 wherein the compound is selected from:

(a) 3-acetyl-1-(acetyloxy)-7-chloro-10-hydroxypyridazino-[4,5-b]quinoline-1,4-dione, (b) 7-chloro-10-hydroxy-1-(3-phenylpropionyloxy) pyridazino[4,5-b]quinoline-4(3H)one, (c) 3-acetyl-1-(acetyloxy)-7,9-dichloro-10-hydroxypyridazino[4,5-b]quinoline-4(3H)one, (d) 7-chloro-2,3-dihydro-10-hydroxy-2-methylpyridazino [4,5-b]quinoline-1,4-dione, or (e) 7-chloro-2,3-dihydro-10-hydroxy-3-methylpyridazino [4,5-b]quinoline-1,4-dione.

6. A method as claimed in claim 1, wherein said neurological disorder is stroke.

* * * * *